United States Patent
Ni et al.

(10) Patent No.: US 7,446,169 B1
(45) Date of Patent: Nov. 4, 2008

(54) HUMAN TUMOR NECROSIS FACTOR RECEPTOR-LIKE 2

(75) Inventors: Jian Ni, Rockville, MD (US); Craig A. Rosen, Laytonsville, MD (US); Reiner L. Gentz, Silver Spring, MD (US); Sally Doreen Patricia Lyn, West Chester, PA (US); Mark Robert Hurle, Norristown, PA (US)

(73) Assignees: Human Genome Sciences, Inc., Rockville, MD (US); SmithKline Beecham Corporation, Philadelphia, PA (US)

( * ) Notice: Subject to any disclaimer, the term of this patent is extended or adjusted under 35 U.S.C. 154(b) by 324 days.

(21) Appl. No.: 09/340,690

(22) Filed: Jun. 29, 1999

Related U.S. Application Data

(60) Division of application No. 08/741,095, filed on Oct. 30, 1996, which is a continuation-in-part of application No. 08/464,595, filed on Jun. 5, 1995, now abandoned, and a continuation-in-part of application No. 08/462,962, filed on Jun. 5, 1995, now abandoned, and a continuation-in-part of application No. 08/462,315, filed on Jun. 5, 1995, now abandoned, which is a continuation-in-part of application No. PCT/US95/05058, filed on Apr. 27, 1995, application No. 08/464,595, which is a continuation-in-part of application No. PCT/US95/05058, application No. 08/462,962, which is a continuation-in-part of application No. PCT/US95/05058.

(51) Int. Cl.
| | |
|---|---|
| A61K 38/16 | (2006.01) |
| A61K 38/17 | (2006.01) |
| C07K 14/435 | (2006.01) |
| C07K 14/47 | (2006.01) |
| C07K 14/705 | (2006.01) |
| C07K 14/71 | (2006.01) |

(52) U.S. Cl. .......................................... 530/350; 514/2
(58) Field of Classification Search .................. 530/350, 530/351, 402, 388.2; 514/2, 8, 12
See application file for complete search history.

(56) References Cited

U.S. PATENT DOCUMENTS

| | | | |
|---|---|---|---|
| 5,194,596 A * | 3/1993 | Tischer et al. | |
| 5,310,662 A | 5/1994 | Evans et al. | 435/62 |
| 5,350,836 A * | 9/1994 | Kopchick et al. | |
| 5,359,039 A | 10/1994 | Smith et al. | 530/350 |
| 5,395,760 A | 3/1995 | Smith et al. | 435/240.1 |
| 5,447,851 A | 9/1995 | Beutler et al. | 435/69.7 |
| 5,464,938 A | 11/1995 | Smith et al. | 530/350 |
| 5,605,690 A | 2/1997 | Jacobs et al. | 424/134.1 |
| 6,303,336 B1 | 10/2001 | Spear et al. | 435/69.1 |

FOREIGN PATENT DOCUMENTS

| | | |
|---|---|---|
| CA | 2045869 | 12/1991 |
| EP | 0 393 438 A2 | 10/1990 |
| EP | 0 555 880 | 8/1993 |
| EP | 0 585 939 A2 | 3/1994 |
| EP | 0 822 984 A | 2/1998 |
| WO | WO 91/02078 | 2/1991 |
| WO | WO 91/09045 | 6/1991 |
| WO | WO 93/20219 | 10/1993 |
| WO | WO 94/09137 | 4/1994 |
| WO | WO 94/13808 | 6/1994 |
| WO | WO 97/04658 | 2/1997 |
| WO | WO 97/06251 | 2/1997 |
| WO | WO 98/25967 | 6/1998 |
| WO | WO 98/51346 | 11/1998 |

OTHER PUBLICATIONS

Murdoch et al., 2000, Blood 95:3032-3043.*
Benjamin et al., 1998, Development 125:1591-1598.*
Vukicevic et al., 1996, PNAS USA 93:9021-9026.*
Massague, 1987, Cell 49:437-438.*
Pilbeam et al., 1993, Bone 14:717-720.*
Skolnick et al., 2000, Trends in Biotech. 18:34-39.*
Bork, 2000, Genome Research 10:398-400.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork, 1998, Trends in Genetics 12:425-427.*
Adams, M.D., et al., "Complementary DNA Sequencing: Expressed Sequence Tags and Human Genome Project," *Science* 252:1651-1656 (1991).
Adams, M.D., et al., "Sequence identification of 2,375 human brain genes," *Nature* 355:632-634 (1992).
Aggarwal, B.B., and Natarajan, K., "Tumor necrosis factors: Developments during the last decade," *Eur. Cytokine Netw.* 7:93-124 (May 1996).

(Continued)

*Primary Examiner*—Elizabeth C. Kemmerer

(57) ABSTRACT

The present invention relates to novel members of the Tumor Necrosis Factor family of receptors. The invention provides isolated nucleic acid molecules encoding a human TR2 receptor and two splice variants thereof. TR2 polypeptides are also provided as are vectors, host cells and recombinant methods for producing the same. The invention further relates to screening methods for identifying agonists and antagonists of TR2 receptor activity. Also provided are diagnostic methods for detecting disease states related to the aberrant expression of TR2 receptors. Further provided are therapeutic methods for treating disease states related to aberrant proliferation and differentiation of cells which express the TR2 receptors.

52 Claims, 31 Drawing Sheets

OTHER PUBLICATIONS

Altschul, S.F., et al., "Basic Local Alignment Search Tool," *J. Mol. Biol.* 215:403-410 (1990).
Armitage, R.J., "Tumor necrosis factor receptor superfamily members and their ligand," *Curr. Opin. Immunol.* 6:407-413 (Jun. 1994).
Ashkenazi, A., et al., "Protection against endotoxic shock by a tumor necrosis factor receptor immunoadhesin," *Proc. Natl. Acad. Sci. USA* 88:10535-10539 (1991).
Baens, M., et al., "Construction and Evaluation of a hncDNA Library of Human 12p Transcribed Sequences Derived from a Somatic Cell Hybrid," *Genomics* 16:214-218 (1993).
Banchereau, J., et al., "Long-Term Human B Cell Lines Dependent on Interleukin-4 and Antibody to CD40," *Science* 251:70-72 (1991).
Banner, D.W., et al., "Crystal Structure of the Soluble Human 55 kd Receptor-Human TNFB Complex: Implications for the TNF Receptor Activation," *Cell* 73: 431-445 (1993).
Baum, P.R., et al., Molecular characterization of murine and human OX40/OX40 ligand systems: identification of a human OX40 ligand as the HTLV-1-regulated protein gp34, *EMBO J.* 13:3992-4001 (Sep. 1994).
Baker, E., et al., "Chromosomal location of the human tumor necrosis factor receptor genes," *Cytogenet. Cell Genet.* 57: 117-118 (1991).
Birkeland, M.L., et al., "Gene structure and chromosomal localization of the mouse homologue of rat OX40 protein," *Eur. J. Immunol.* 25:926-930 (Apr. 1995).
Camerini, D., et al., "The T Cell Activation Antigen CD27 Is a Member of the Nerve Growth Factor/Tumor Necrosis Factor Receptor Gene Family," *J. Immunol.* 147:3165-3169 (1991).
Chang, et al., "Identification of a new member of the steroid receptor superfamily by cloning and sequence analysis," *Biochem. Biophys. Res. Comm.* 155:971-977 (1988).
Chinnaiyan, A.M., et al., "Signal Transduction by DR3, a Death Domain-Containing Receptor Related to TNFR-1 and CD95," *Science* 274:990-992 (1996).
Dürkop, H., et al., "Molecular Cloning and Expression of a New Member of the Nerve Growth Factor Receptor Family That is Characteristic for Hodgkin's Disease," *Cell* 68:421-427 (1992).
Engelman, H., et al., "Two Tumor Necrosis Factor-binding Proteins Purified from Human Urine," *J. Biol. Chem.* 265:1531-1536 (1990).
Feinstein, E., et al., "The death domain: a module shared by proteins with diverse cellular functions," *TIBS* 20:342-344 (Sep. 1995).
Gillette-Ferguson, I., and Sidman, C.L., "A specific intercellular pathway of apoptotic cell death is defective in the mature peripheral T cells of autoimmune *lpr* and *gld* mice," *Eur. J. Immunol.* 24:1181-1185 (May 1994).
Goodwin, R.G., et al., "Molecular cloning of a ligand for the inducible T cell gene 4-1BB: a member of an emerging family of cytokines with homology to tumor necrosis factor," *Eur. J. Immunol.* 23:2631-2641 (1993).
Gruss, H.-J., et al., "Pleiotropic Effects of the CD30 Ligand on CD30-Expressing Cells and Lymphoma Cell Lines," *Blood* 83:2045-2056 (Apr. 1994).
Himmler, A., et al., "Molecular Cloning and Expression of Human and Rat Tumor Necrosis Factor Receptor Chain (p60) and Its Soluble Derivative, Tumor Necrosis Factor-Binding Protein," *DNA and Cell Biol.* 9:705-715 (1990).
Hohmann, H.-P., et al., "Two Different Cell Types Have Different Major Receptors for Human Tumor Necrosis Factor (TNF$\alpha$)," *J. Biol. Chem.* 264:14927-14934 (1989).
Howard, S.T., et al., "Vaccinia Virus Homologues of the Shope Fibroma Virus Inverted Terminal Repeat Proteins and a Discontinuous ORF Related to the Tumor Necrosis Factor Receptor Family," *Virol.* 180:633-647 (1991).
Hsu, K.C., and Chao, M.V., "Differential Expression and Ligand Binding Properties of Tumor Necrosis Factor Chimeric Mutants," *J. Biol. Chem.* 268:16430-16436 (1993).
Hu, F.-Q., et al., "Cowpox Virus Contains Two Copies of an Early Gene Encoding a Soluble Secreted Form of the Type II TNF Receptor," *Virol.* 204:343-356 (Oct. 1994).
Inui, S., et al., "Identification of the intracytoplasmic region essential for signal transduction through a B cell activation molecule, CD40," *Eur. J. Immunol.* 20:1747-1753 (1990).

Itoh, N., et al., "The Polypeptide Encoded by the cDNA for Human Cell Surface Antigen Fas Can Mediate Apoptosis," *Cell* 66:233-243 (1991).
Johnson, D., et al., "Expression and Structure of the Human NGF Receptor," *Cell* 47:545-554 (1986).
Kramer, P.H., et al., "Regulation of apoptosis in the immune system," *Curr. Opin. Immunol.* 6:279-289 (Apr. 1994).
Kwon, B.S., and Weissman, S.M., "cDNA sequences of two inducible T-cell genes," *Proc. Natl. Acad. Sci. USA* 86:1963-1967 (1989).
Kwon, B.S., et al., "Genomic Organization and Chromosomal Localization of the T-Cell Agntigen 4-1BB," *J. Immunol.* 152:2256-2262 (Mar. 1994).
Lewis, M., et al., "Cloning and expression of cDNAs for two distinct murine tumor necrosis factor receptors demonstrate one receptor is species specific," *Proc. Natl. Acad. Sci. USA* 88:2830-2834 (1991).
Loetscher, H., et al., "Molecular Cloning and Expression of the Human 55 kd Tumor Necrosis Factor Receptor," *Cell* 61:351-359 (1990).
Mallett, S., et al., "Characterization of the MRC OX40 antigen of activated CD4 positive T lymphocytes—a molecule related to nerve growth factor receptor," *EMBO J.* 9:1063-1068 (1990).
Mallett, S., and Barclay, A.N., "A new superfamily of cell surface proteins related to the nerve growth factor receptor," *Immunol. Today* 12:220-223 (1991).
Montgomery, R.I., et al., "A New Member of the TNG/NGF Receptor Family Can Mediate Herpes Simplex Virus 1 Entry Into Cells," *Cytokine Netw.* 7:159, Abstract No. L7 (1996).
Muzio, M., et al., FLICE, A Novel FADD-Homologous ICD/CED-3-like Protease, Is Recruited to the CD95 (Fas/APO-1) Death-Inducing Signaling Complex, *Cell* 85:817-827 (Jun. 1996).
Nophar, Y., et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *EMBO J.* 9:3269-3278 (1990).
Pfeffer, K., et al., "Mice Deficient for the 55 kd Tumor Necrosis Factor Receptor Are Resistant to Endotoxic Shock, yet Succumb to L. monocytogenes Infection," *Cell* 73:457-467 (1993).
Piguet, P.F., et al., "Evolution of collagen arthritis in mice is arrested by treatment with anti-tumor necrosis factor (TNF) antibody or a recombinant soluble TNF receptor," *Immunol.* 77:510-514 (1992).
Pollock, K.E., et al., "Inductible T Cell Antigen 4-1BB," *J. Immunol.* 150:771-781 (1993).
Radeke, M.J., et al., "Gene transfer and molecular cloning of the rat nerve growth factor receptor," *Nature* 325:593-597 (1987).
Rossol-Voth, R., et al., "In vivo protective effect of tumor necrosis factor αagainst experimental infection with herpes simplex virus type 1," *J. Gen. Virol.* 72:143-147 (1991).
Rothe, M., et al., "A Novel Family of Putative Signal Transducers Associated with the Cytoplasmic Domain of the 75 kDa Tumor Necrosis Factor Receptor," *Cell* 78:681-692 (Aug. 1994).
Schall, T.J., et al., "Molecular Cloning and Expression of a Receptor for Human Tumor Necrosis Factor," *Cell* 61:361-370 (1990).
Smith, C.A., et al., "A Receptor for Tumor Necrosis Factor Defines an Unusual Family of Cellular and Viral Proteins," *Science* 248:1019-1023 (1990).
Smith, C.A., et al., "T2 Open Reading Frame from the Shope Fibroma Virus Encodes a Soluble Form of the TNF Receptor," *Biochem. Biophys. Res. Comm.* 176:335-342 (1991).
Smith, C.A., et al., "CD30 Antigen, a Marker for Hodgkin's Lymphoma, Is a Receptor Whose Ligand Defines an Emerging Family of Cytokines with Homology to TNF," *Cell* 73:1349-1360 (1993).
Smith, G.L., "Vaccinia virus glycoproteins and immune evasion," *J. Gen. Virol.* 74:1725-1740 (1993).
Stamenkovic, I., et al., "A B-lymphocyte activation molecule related to the nerve growth factor receptor and induced by cytokines in carcinomas," *EMBO J.* 8:1403-1410 (1989).
Tartaglia, L.A., et al., "The two different receptors for tumor necrosis factor mediate distinct cellular responses," *Proc. Natl. Acad. Sci. USA* 88:9292-9296 (1991).
Tartaglia, L.A., and Goeddel, D.V., "Tumor Necrosis Factor Receptor Signaling," *J. Biol. Chem.* 267:4304-4307 (1992).
Tartaglia, L.A., et al., "A Novel Domain within the 55 kd TNF Receptor Signals Cell Death," *Cell* 74:845-853 (1993).

Torcia, M., et al., "Nerve Growth Factor Is an Autocrine Survival Factor for Memory B Lymphocytes," *Cell* 85:345-356 (1996).

Van Lier, R.A.W., et al., "Tissue Distribution and Biochemical and Functional Properties of Tp55 (CD27), a Novel T Cell Differentiation Antigen," *J. Immunol.* 139:1589-1596 (1987).

Van Ostade, X., et al., "Human tumor necrosis factor mutants with preferential binding to and activity on either the R55 or R75 receptor," *Eur. J. Biochem.* 220:771-779 (Mar. 1994).

Vandenabeele, P., et al., "Two Tumor necrosis factor receptors: structure and function," *Trends Cell. Biol.* 5:392-399 (Oct. 1995).

Database Embl-new3 on MASPAR, Acc. No. L23876, Glascow, E., and Schechter, N., "Nucleotide sequence of a GFAP-like Intermediate Filament cDNA from Goldfish retina," (Sep. 1993).

Database EST-STS on MASPAR, Acc. No. H14106, Hillier, L., et al., "WashU-Merck EST Project," (Jul. 1995).

Database EMBL/GenBank/DDJB on MASPAR, Genetique Moleculaire (sic) et Biologie du developpement (Villejuif Cedex, France), Acc. No. Z38433, GeneExpress, Direct Submission (Oct. 1994).

Database EST-STS on MASPAR, Whitehead Institute/MIT Center for Genome Research, Acc. No. G11923, Hudson, T., "Whitehead Institute/MIT Center for Genome Research; Physically Mapped STSs" (Oct. 1995).

Database EMBL-new3 on MASPAR, Acc. No. X60370, X60371, X60550, Zauner, W., et al., "Identification of Two Distinct microtubule Binding Domains on Recombinant Rat MAP 1B," (Oct. 1992).

Database EMBL-new3 on MASPAR, Acc. No. X75491, Aslanidis, C., et al., "Genomic Organization of the Human Lysosomal Acid Lipase Gene (LIPA)" (Mar. 1994).

Database A-Geneseq24 on MASPAR, Acc. No. R38859, Aruffo, A.A., et al., "CD4OCR Receptor and its' (sic) Ligands used to Inhibit B-Cell Activation in Allergy and Auto-immune Disease," Submitted Feb. 7, 1994, EP, A, 555880 (Aug. 1993).

International Search Report from PCT/US96/15003.

International Search Report from PCT/US96/18540.

International Search Report from PCT/US96/16849.

NCBI Entrez, GenBank Report, Accession No. Z38440, from Auffray, C., et al. (Oct. 1994).

NCBI Entrez, GenBank Report, Accession No. Z42185, from Auffray, C., et al. (Nov. 1994).

NCBI Entrez, GenBank Report, Accession No. H51006, from Hillier, L., et al. (Sep. 1995).

NCBI Entrez, GenBank Report, Accession No. W32997, from Hillier, L., et al. (Oct. 1996).

NCBI Entrez, GenBank Report, Accession No. W35383, from Hillier, L., et al. (Oct. 1996).

NCBI Entrez, GenBank Report, Accession No. AA088190, Hillier, L., et al. (Oct. 1996).

NCBI Entrez, GenBank Report, Accession No. AA088363, Hillier, L., et al. (Oct. 1996).

NCBI Entrez, GenBank Report, Accession No. AA015734, Hillier, L., et al. (Nov. 1996).

NCBI Entrez, GenBank Report, Accession No. AA015831, Hillier, L., et al. (Nov. 1996).

NCBI Entrez, GenBank Report, Accession No. AA018179, Hillier, L., et al. (Nov. 1996).

NCBI Entrez, GenBank Report, Accession No. AA020824, Hillier, L., et al. (Jan. 1997).

NCBI Entrez, GenBank Report, Accession No. AA020847, Hillier, L., et al. (Jan. 1997).

NCBI Entrez, GenBank Report, Accession No. AA021564, Hillier, L., et al. (Jan. 1997).

NCBI Entrez, GenBank Report, Accession No. AA021617, Hillier, L., et al. (Jan. 1997).

NCBI Entrez, GenBank Report, Accession No. AA297974, Adams, M.D., et al. (Apr. 1997).

NCBI Entrez, GenBank Report, Accession No. AA433981, Hillier, L., et al. (May 1997).

NCBI Entrez, GenBank Report, Accession No. AA293583, Hillier, L., et al. (Aug. 1997).

NCBI Entrez, GenBank Report, Accession No. AA481843, Hillier, L., et al. (Aug. 1997).

NCBI Entrez, GenBank Report, Accession No. AA481990, Hillier, L., et al. (Aug. 1997).

NCBI Entrez, GenBank Report, Accession No. AA261917, NCI-CGAP (Aug. 1997).

NCBI Entrez, GenBank Report, Accession No. AA262421, NCI-CGAP (Aug. 1997).

NCBI Entrez, GenBank Report, Accession No. AA573503, NCI-CGAP (Aug. 1997).

NCBI Entrez, GenBank Report, Accession No. AA573487, NCI-CGAP (Sep. 1997).

NCBI Entrez, GenBank Report, Accession No. AA577277, NCI-CGAP (Sep. 1997).

NCBI Entrez, GenBank Report, Accession No. AA418865, Hillier, L., et al. (Oct. 1997).

NCBI Entrez, GenBank Report, Accession No. AA418866, Hillier, L., et al. (Oct. 1997).

NCBI Entrez, GenBank Report, Accession No. AA426526, Hillier, L., et al. (Oct. 1997).

NCBI Entrez, GenBank Report, Accession No. AA430530, Hillier, L., et al. (Oct. 1997).

NCBI Entrez, GenBank Report, Accession No. AA613360, NCI-CGAP (Oct. 1997).

NCBI Entrez, GenBank Report, Accession No. AA683532, Hillier, L., et al. (Dec. 1997).

NCBI Entrez, GenBank Report, Accession No. AA722732, Hillier, L., et al. (Jan. 1998).

NCBI Entrez, GenBank Report, Accession No. AA761384, NCI-CGAP (Feb. 1998).

NCBI Entrez, GenBank Report, Accession No. AA768114, NCI-CGAP (Feb. 1998).

NCBI Entrez, GenBank Report, Accession No. AA831386, NCI-CGAP (Apr. 1998).

NCBI Entrez, GenBank Report, Accession No. AA902924, NCI-CGAP (Apr. 1998).

NCBI Entrez, GenBank Report, Accession No. AA864866, NCI-CGAP (May 1998).

NCBI Entrez, GenBank Report, Accession No. AA844171, NCI-CGAP (Dec. 1998).

NCBI Entrez, GenBank Report, Accession No. AA890591, NCI-CGAP (Jan. 1999).

Sequence cited and provided to applicants by Examiner in U.S. Appl. No. 08/741,095 in correspondence dated Mar. 23, 1998: Derwent Genseq. Database, Accession No. R42248, from Leonard, W.J., et al. (May 1995).

Sequence cited and provided to Applicants by Examiner in U.S. Appl. No. 08/741,095 in correspondence dated Mar. 23, 1998: Derwent Genseq. Databse, Accession I54182, from Baens, M., et al. (May 1996).

Kwon, B.S. et al., "A Newly Identified Member of the Tumor Necrosis Factor Receptor Superfamily with a Wide Tissue Distribution and Involvement in Lymphocyte Activation," *J. Biol. Chem.* 272:14272-14276 (May 1997).

Supplementary Partial European Search Report, Issued in European Patent Application No. EP 959117662 on Mar. 16, 2000.

Førre, Ø. et al., "New treatment possibilities in rheumatoid arthritis," *Scand. J. Rheumatol.* 29:73-84, Scandinavian University Press (2000).

Keystone, E.C., "The Role of Tumor Necrosis Factor Antagonism in Clinical Practice," *J. Rheumatol.* 26(*Suppl. 57*):22-28, The Journal of Rheumatology Publishing Company Ltd. (May 1999).

Wallace, C.A., et al., "Predicting Remission in Juvenile Rheumatoid Arthritis with Methotrexate Treatment," *J. Rheumatol.* 20:118-122, The Journal of Rheumatology Publishing Company Ltd. (1993).

European Supplementary Partial European Search Report, Application No. EP 96 94 2776, dated Mar. 3, 2003.

European Supplementary Partial European Search Report, Application No. EP 96 94 2776, dated Jun. 2, 2003.

US 5,843,791, 12/1998, Hauptmann et al. (withdrawn)

\* cited by examiner

```
              10                  30                  50
    GCACGAGCTGCCTCCCGCAGGCGCCACCTGTGTCCCCAGCGCCGCTCCACCCAGCAGGC
              70                  90                 110
    CTGAGCCCCTCTCTGCTGCCAGACACCCCCTGCTGCCCACTCTCCTGCTGCTCGGGTTCT
             130                 150                 170
    GAGGCACAGCTTGTCACACCGAGGCGGATTCTCTTTCTCTTTCTCTTTCTCTTCTGGCCC
             190                 210                 230
    ACAGCCGCAGCAATGGCGCTGAGTTCCTCTGCTGGAGTTCATCCTGCTAGCTGGGTTCCC
             250                 270                 290
    GAGCTGCCGGTCTGAGCCTGAGGCATGGAGCCTCCTGGAGACTGGGGGCCTCCTCCCTGG
                                 M  E  P  P  G  D  W  G  P  P  W
             310                 330                 350
    AGATCCACCCCCAAAACCGACGTCTTGAGGCTGGTGCTGTATCTCACCTTCCTGGGAGCC
     R  S  T  P  K  T  D  V  L  R  L  V  L  Y  L  T  F  L  G  A
             370                 390                 410
    CCCTGCTACGCCCCAGCTCTGCCGTCCTGCAAGGAGGACGAGTACCCAGTGGGCTCCGAG
     P  C  Y  A  P  A  L  P  S  C  K  E  D  E  Y  P  V  G  S  E
             430                 450                 470
    TGCTGCCCCAAGTGCAGTCCAGGTTATCGTGTGAAGGAGGCCTGCGGGGAGCTGACGGGC
     C  C  P  K  C  S  P  G  Y  R  V  K  E  A  C  G  E  L  T  G
             490                 510                 530
    ACAGTGTGTGAACCCTGCCCTCCAGGCACCTACATTGCCCACCTCAATGGCCTAAGCAAG
     T  V  C  E  P  C  P  P  G  T  Y  I  A  H  L  N  G  L  S  K
             550                 570                 590
    TGTCTGCAGTGCCAAATGTGTGACCCAGCCATGGGCCTGCGCGCGAGCCGGAACTGCTCC
     C  L  Q  C  Q  M  C  D  P  A  M  G  L  R  A  S  R  N  C  S
             610                 630                 650
    AGGACAGAGAACGCCGTGTGTGGTTGCAGCCCCAGGCCACTTCTGCATCGTCCAGGACGGG
     R  T  E  N  A  V  C  G  C  S  P  G  H  F  C  I  V  Q  D  G
             670                 690                 710
    GACCACTGCGCCGCGTGCCGCGCTTACGCCACCTCCAGCCCGGGCCAGAGGGTGCAGAAG
     D  H  C  A  A  C  R  A  Y  A  T  S  S  P  G  Q  R  V  Q  K
             730                 750                 770
    GGAGGCACCGAGAGTCAGGACACCCTGTGTCAGAACTGCCCCCCGGGGACCTTCTCTCCC
     G  G  T  E  S  Q  D  T  L  C  Q  N  C  P  P  G  T  F  S  P
             790                 810                 830
    AATGGGACCCTGGAGGAATGTCAGCACCAGACCAAGTGCAGCTGGCTGGTGACGAAGGCC
     N  G  T  L  E  E  C  Q  H  Q  T  K  C  S  W  L  V  T  K  A
             850                 870                 890
    GGAGCTGGGACCAGCAGCTCCCACTGGGTATGGTGGTTTCTCTCAGGGAGCCTCGTCATC
     G  A  G  T  S  S  S  H  W  V  W  W  F  L  S  G  S  L  V  I
```

FIG.1A

```
                910                  930                 950
GTCATTGTTTGCTCCACAGTTGGCCTAATCATATGTGTGAAAAGAAGAAAGCCAAGGGGT
 V  I  V  C  S  T  V  G  L  I  I  C  V  K  R  R  K  P  R  G
                970                  990                 1010
GATGTAGTCAAGGTGATCGTCTCCGTCCAGCGGAAAAGACAGGAGGCAGAAGGTGAGGCC
 D  V  V  K  V  I  V  S  V  Q  R  K  R  Q  E  A  E  G  E  A
               1030                 1050                 1070
ACAGTCATTGAGGCCCTGCAGGCCCCTCCGGACGTCACCACGGTGGCCGTGGAGGAGACA
 T  V  I  E  A  L  Q  A  P  P  D  V  T  T  V  A  V  E  E  T
               1090                 1110                 1130
ATACCCTCATTCACGGGGAGGAGCCCAAACCACTGACCCACAGACTCTGCACCCCGACGC
 I  P  S  F  T  G  R  S  P  N  H  *
               1150                 1170                 1190
CAGAGATACCTGGAGCGACGGCTGAATGAAAGAGGCTGTCCACCTGGCGGAACCACCGGA
               1210                 1230                 1250
GCCCGGAGGCTTGGGGGCTCCACCCTGGACTGGCTTCCGTCTCCTCCAGTGGAGGGAGAG
               1270                 1290                 1310
GTGGCGCCCCTGCTGGGGTAGAGCTGGGGACGCCACGTGCCATTCCCATGGGCCAGTGAG
               1330                 1350                 1370
GGCCTGGGGCCTCTGTTCTGCTGTGGCCTGAGCTCCCCAGAGTCCTGAGGAGGAGCGCCA
               1390                 1410                 1430
GTTGCCCCTCGCTCACAGACCACACACCCAGCCCTCCTGGGCCAACCCAGAGGGCCTTCA
               1450                 1470                 1490
GACCCCAGCTGTGTGCGCGTCTGACTCTTGTGGCCTCAGCAGGACAGGCCCCGGGCACTG
               1510                 1530                 1550
CCTCACAGCCAAGGCTGGACTGGGTTGGCTGCAGTGTGGTGTTTAGTGGATACCACATCG
               1570                 1590                 1610
GAAGTGATTTTCTAAATTGGATTTGAATTCGGCTCCTGTTTTCTATTTGTCATGAAACAG
               1630                 1650                 1670
TGTATTTGGGGAGATGCTGTGGGAGGATGTAAATATCTTGTTTCTCCTCAAAAAAAAAAA
               1690
AAAAAAAAAAAAAAAAAAAAAAAA
```

FIG.1B

```
  1  MEPPGDWGPPPWRSTPKTDVLRLVLYLTFLGAPCYAPALPSCKEDEYPVG   50
         ...: ||. .:. |  .:..   ..|.:.:|  :
  1  ................MVSLPRLCALWGCLLTAVHLGQCVTCSDKQYLHD   34

51  SECCPKCSPGYRVKEACGELTGTVCEPCPPGTYIAHLNGLSKCLQCQMCD  100
     ::||. | || |:.. |..|. | |.||..|.: |::|   :| |.. |:
 35  GQCCDLCQPGSRLTSHCTALEKTQCHPCDSGEFSAQWNREIRCHQHRHCE   84

101  PAMGLRASRNCSRTENAVCGCSPGHFCIVQDGDHCAACRAYATSSPGQRV  150
     |. |||..:: ..   .:.||.|..|: |. .|  |.|| ....: || |
 85  PNQGLRVKKEGTAESDTVCTCKEGQHCTSKD...CEACAQHTPCIPGFGV  131

151  QKGGTESQDTLCQNCPPGTFSPNGTL.EECQHQTKC.SWLVTKAGAGTSS  198
      .:||. ||:|: ||.| ||  .:.| |.|  .|.|  .. :.  .|||
132  MEMATETTDTVCHPCPCGFFSNQSSLFEKCYPNTSCEDKNLEVLQKGTSQ  181

199  SH.......WVWWFLSGSLVIVIVCSTVGLIICVKR..RKPRGDVVKVIV  239
      .:       ::: :|  .:|:.|:.....|:::::|:  :||:::  ..
182  TNVICGLKSRMRALLVIPVVMGILITIFGVFLYIKKVVKKPKDNEMLPPA  231

240  SVQRKRQEAEG......EATVIEALQAPPDVTTVAVEETIPSFTGRSPNH  283
     . ....|| |:       .|.| |.|:..||  ...|. |. :| ...
232  ARRQDPQEMEDYPGHNTAAPVQETLHGCQPVTQEDGKESRISVQERQVTD  281
```

FIG.2

```
              10                    30                    50
CCCCCTTCTACAGGAAACCCGGAGTGGACTGGAACGGTGCAGGGGGAGAACTCGCCCCTC
              70                    90                   110
CCATCGGGCGCCTCCTTCATACCGGCCCTTCCCCTCGGCTTTGCCTGGACAGCTCCTGCC
             130                   150                   170
TCAGGCAGCGCCACCTGTGTCGCCCAGCGCCGCTCCACCCAGCAGGCCTGAGCCCCTCTC
             190                   210                   230
TGCTGCCAGACACCCCCTGCTGCCCACTACTCCTGCTGCTCGGGTTCTGAGGCACAGCTT
             250                   270                   290
GTCACACCGAGGCGGATTCTCTTTCTCTTTCTCTTTCTCTTCTGGCCCACAGCCGCAGCA
             310                   330                   350
ATGGCGCTGAGTTCCTCTGCTGGAGTTCATCCTGCTAGCTGGGTTCCCGAGCTGCCGGTC
             370                   390                   410
TGAGCCTGAGTCATGGAGCCTCCTGGAGACTGGGGGCCTCCTCCCTGGAGATCCACCCCC
                 M  E  P  P  G  D  W  G  P  P  P  W  R  S  T  P
             430                   450                   470
AGAACCGACGTCTTGAGGCTGGTGCTGTATCTCACCTTCCTGGGAGCCCCCTGCTACGCC
 R  T  D  V  L  R  L  V  L  Y  L  T  F  L  G  A  P  C  Y  A
             490                   510                   530
CCAGCTCTGCCGTCCTGCAAGGAGGACGAGTACCCAGTGGGCTCCGAGTGCTGCCCCAAG
 P  A  L  P  S  C  K  E  D  E  Y  P  V  G  S  E  C  C  P  K
             550                   570                   590
TGCAGTCCAGGTTATCGTGTGAAGGAGGCCTGCGGGGAGCTGACGGGCACAGTGTGTGAA
 C  S  P  G  Y  R  V  K  E  A  C  G  E  L  T  G  T  V  C  E
             610                   630                   650
CCCTGCCCTCCAGGCACCTACATTGCCCACCTCAATGGCCTAAGCAAGTGTCTGCAGTGC
 P  C  P  P  G  T  Y  I  A  H  L  N  G  L  S  K  C  L  Q  C
             670                   690                   710
CAAATGTGTGACCCAGATATTGGTTCCCCCTGTGACCTCAGGGGAAGAGGTCACCTGGAG
 Q  M  C  D  P  D  I  G  S  P  C  D  L  R  G  R  G  H  L  E
             730                   750                   770
GCTGGTGCCCACCTGAGTCCAGGCAGACAGAAAGGGGAACCAGACCCAGAGGTGGCCTTT
 A  G  A  H  L  S  P  G  R  Q  K  G  E  P  D  P  E  V  A  F
             790                   810                   830
GAGTCACTGAGCGCAGAGCCTGTCCATGCGGCCAACGGCTCTGTCCCCTTGGAGCCTCAT
 E  S  L  S  A  E  P  V  H  A  A  N  G  S  V  P  L  E  P  H
             850                   870                   890
GCCAGGCTCAGCATGGCCAGTGCTCCCTGCGGCCAGGCAGGACTGCACCTGCGGGACAGG
 A  R  L  S  M  A  S  A  P  C  G  Q  A  G  L  H  L  R  D  R
             910                   930                   950
GCTGACGGCACACCTGGGGGCAGGGCCTGAGCCTACAGGGAGGCACAGGGCAGGTGGGCT
 A  D  G  T  P  G  G  R  A  *
```

FIG.4A

```
                970                  990                 1010
        AGCCATGAACAGAAGAGGAAGCTGGAGTGCTTTGGGGGTTCATGCATGTAGGCTGGGATT
               1030                 1050                 1070
        TGGGGCTCACACCTCAACCTGCATGCCCAGTTCCATGCCCCTCCCCTCTTGTGAAAGCAC
               1090                 1110                 1130
        CTGTCTACTTGGGCTGAGGATGTGGGGGCACAGGTGGCAGGTGAGGCTGCCCTCAGGAGG
               1150                 1170                 1190
        GGCCCAGGCCCAGCTTGTACCCCACCTCCACCAGTACCTGAAGAAGTGGGGCTCTCACCC
               1210                 1230                 1250
        TACCTGCCTCTGCCATTGGAATGGCCTGGTTTGCACAGATGGGAAACCCGTTTGAGGGGT
               1270                 1290                 1310
        GGGTGTCTGGGTGGGCACGTGGGGCGAGGACCTGCCTGAGGGACCCTGCCCTGGAACTGA
               1330                 1350                 1370
        CAGTGCAAGCTCGGCGTCCTGCCCATCTGGGCAGAAGGCTGGTTTCTCCCATCAACGAAG
               1390                 1410                 1430
        CCCTCCCAGGACCTTCCTGCAAGCCCTCGTCCCACACGCAGCTCTGCCGTCCCTTGGTGT
               1450                 1470                 1490
        CCCTCCCGGCCTCAGGTCCTCCATGCTGGGTACCTCTGGGCACCTCGTTTGGCTGAGCCA
               1510                 1530                 1550
        GGGGTTCAGCCTGGCAGGGCGCCCTGGCAGCAGTCCTTGGCCTGTGGATGCTGTCCTGGC
               1570                 1590                 1610
        CTGTGGATGGTGTCCCGCCCTCCACGTACCCCTCTCACCCCCTCCTCTTGGACTCCAGCC
               1630                 1650                 1670
        ATGGGCCTGCGCGCGAGCCGGAACTGCTCCAGGACAGAGAACGCCGTGTGTGGCTGCAGC
               1690                 1710                 1730
        CCAGGCCACTTCTGCATCGTCCAGGACGGGGACCACTGCGCCGCGTGCCGCGCTTACGCC
               1750                 1770                 1790
        ACCTCCAGCCCGGGCCAGAGGGTGCAGAAGGGAGGCACCGAGAGTCAGGACACCCTGTGT
               1810                 1830                 1850
        CAGAACTGCCCCCCGGGGACCTTCTCTCCCAATGGGACCCTGGAGGAATGTCAGCACCAG
               1870                 1890                 1910
        ACCAATTGGCCTAATCATATGTGTGAAAAGAAGAAAGCCAAGGGGTGAGCACACGGTGGC
               1930                 1950                 1970
        CCCATCAGGGTTCATGTCCCCAGCCGTCACCTCTTGGAGCTCTGTCACCCCAAGCCTGGG
               1990                 2010                 2030
        AGGTGGCCCCAGAGCTTTTCCAGGATCCGCGGCTCCTCCCAGGGCAGCCACTGCAGGCTG
               2050                 2070                 2090
        GGGCAGGTGTATGTAGTCAAGGTGATCGTCTCCGTCCAGCGGTAAAAGACAGGAGGCAGA
               2110                 2130                 2150
        AGGTGAGGCCACAGTCATTGAGCCCTGCAGGCCCCTCCGGACGTCACCACGGTGGCCGTG
               2170                 2190                 2210
        GAGGAGACAATACCCTCATTCACGGGGAGGAGCCCAAACCACTGACCCACAGACTCTGCA
```

FIG.4B

```
            2230                  2250                  2270
CCCCGACGCCAGAGATACCTGGAGAGACGGCTGCTGATAGAGGCTGTCCACCTGGCGAAA
            2290                  2310                  2330
CCACCGGAGCCCGGAGGCTTGGGGGCTCCGCCCTGGGCTGGTTTCCGTCTCCTCCAGTGG
            2350                  2370                  2390
AGGGAGAGGTGGTGCCCCTGCTGGTGGTAGAGCTGGGGACGCCACGTGCCATTCCCATGG
            2410                  2430                  2450
TTCAGTGAGGGGCTGGTGGCCTCTGTTCTGCTGTGGCCTGAGCTCCCCAGAGTCCTGAGG
            2470                  2490                  2510
AGGAGCCCCAGTTGCCCCTCGCTCACAGACCACACACCCAGCCCTCCTGGGCCAACCCAG
            2530                  2550                  2570
AGGCCCCTTCAGACCCCAGCTGTCTGCGCGTCTGACTCTTGTGGCCTCAGCAGGACAGGC
            2590                  2610                  2630
CCCGGGCACTGCCTCACAGCCAAGGCTGGAATGGGTTGGCTGCAGTGTGGTGTTTAGTGG
            2650                  2670                  2690
ATACCACATCGGAAGTGATTTTCTAAAAATTGGATTTGAATTCGGAAAAAAA
```

FIG.4C

```
1    MEPPGDWGPPPWRSTPRTDVLRLVLYLTFLGAPCYAPALPSCKEDEY..P    48
     |.|.: |:: :     . :... |.  :.|  .|: :.: ..|:  ||  .
1    MAPVAVWAALAVGLELWAAAHALPAQVAF..TPYAPEPGSTCRLREYYDQ    48

49   VGSECCPKCSPGYRVKEACGELTGTVCEPCPPGTYIAHLNGLSKCLQCQM    98
     .:  ||.|||||  :.|   |.. .:|||:.|..:||.. :| :..|| |.
49   TAQMCCSKCSPGQHAKVFCTKTSDTVCDSCEDSTYTQLWNWVPECLSCGS    98

99   ..CDPDIGSPCDLRGRGHL.............EAGAHLSPGRQKGEPDPE   133
     :........  |:...::           :.|..|::. .|. |: :
99   RCSSDQVETQACTREQNRICTCRPGWYCALSKQEGCRLCAPLRKCRPGFG   148

134  VA.............................FESLSAEPVHAANGS      150
     ||                              : .: | |.:|. :.
149  VARPGTETSDVVCKPCAPGTFSNTTSSTDICRPHQICNVVAIPGNASMDA   198

151  VPLEPHARLSMASAPC..GQAGLHLRDRADGTPGGRA.............   185
     |. .. :  |||.:::  .|:.    .:.:..||:...
199  VCTSTSPTRSMAPGAVHLPQPVSTRSQHTQPTPEPSTAPSTSFLLPMGPS   248
```

FIG.5

```
                    10                          30                          50
        AAAGCTCGGGCTCCACCGGGGACGACCGCTCCTAGAAACTGAGTGGTATCCCCCGGGCCT
                    70                          90                         110
        GCAGGAATTCCAACCTGCCTGAAGGGACCCTGCCCTGGAACTGACAGTGCAAGCTCGGCG
                   130                         150                         170
        TCCTGCCCATCTGGGAAGAAGGCTGGTTTCTCCCATCAACGAAGCCCTCCCAGGACCTTC
                   190                         210                         230
        CTGCAAGCCCTCGTCCCACACGCAGCTCTGCCGTCCCTTGGTGTCCCTCCCGGCCTCAGG
                   250                         270                         290
        TCCTCCATGCTGGGTACCTCTGGGCACCTCGTTTGGCTGAGCCAGGGGTTCAGCCTGGCA
              M  L  G  T  S  G  H  L  V  W  L  S  Q  G  F  S  L  A
                   310                         330                         350
        GGGCGCCCTGGCAGCAGTCCTTGGCCTGTGGATGCTGTCCTGGCCTGTGGATGGTGTCCC
           G  R  P  G  S  S  P  W  P  V  D  A  V  L  A  C  G  W  C  P
                   370                         390                         410
        GGCCTCCACGTACCCCCTCTCAGCCCCTCCTCTTGGACTCCAGCCATGGGCCTGCGCGCG
           G  L  H  V  P  P  L  S  P  S  S  W  T  P  A  M  G  L  R  A
                   430                         450                         470
        AGCCGGAACTGCTCCAGGACAGAGAACGCCGTGTGTGGCTGCAGCCCAGGCCACTTCTGC
           S  R  N  C  S  R  T  E  N  A  V  C  G  C  S  P  G  H  F  C
                   490                         510                         530
        ATCGTCCAGGACGGGGACCACTGCGCCGCGTGCCGCGCTTACGCCACCTCCAGCCCGGGC
           I  V  Q  D  G  D  H  C  A  A  C  R  A  Y  A  T  S  S  P  G
                   550                         570                         590
        CAGAGGGTGCAGAAGGGAGGCACCGAGAGTCAGGACACCCTGTGTCAGAACTGCCCCCGG
           Q  R  V  Q  K  G  G  T  E  S  Q  D  T  L  C  Q  N  C  P  R
                   610                         630                         650
        GGACCTTCTCTCCCAATGGGACCCTGGAGGAATGTCAGCACCAGACCAAGTAAGTGAACC
           G  P  S  L  P  M  G  P  W  R  N  V  S  T  R  P  S  K  *
                   670                         690                         710
        CGGGGGAGGCCAGCTCTGTGCCCTGGGGAGGGGGCTCCACGTTGCTTCCCTGGGAGATGA
                   730                         750                         770
        CCGTCTTCTCCAGCAGAAAGGTTGAAGGTCCCACCCTGAGCGGCACCCTGGTCACATGCC
                   790                         810                         830
        TGCGTCCAGGAGAGCTGCAGGGTGAAGCCTGTGTGCCCCAGATAACCCCTTCCATGGGCC
                   850                         870                         890
        CAGACAAAGCCTCATCAGATCTGAGCTTCCTGGAGGCTCAGGATGGGCCTTCCCAGAAGC
                   910                         930                         950
        AGGCCCAGAGGGAGGCTGCCTCCAGATCCCCTGTCCCCTGGGGCTGTGGGTGTCCCTGAA
                   970                         990                        1010
        TGTCAGGGCCATGGGAGGGCCCCTGGGCTTCAGGGGTTGGGGAAAAGTGAACACTCTGCTC
```

FIG.7A

```
         1030              1050              1070
   TTTGTCCACCTTCGGGAGGACAACCTTCAAATGCTGACCCTGGGCCCCTAACTGACCTGA
         1090              1110              1130
   GACTTCAGAGCTTCTTGGGAGGAGCTGGGGTCCCCAGCGGAGCCTGGGATGGAGCAGGG
         1150              1170              1190
   ATGGCTGCCCCAGGGAGGGGGCGGTGGGGCCTTCCATCCTGCTCTGCCCTCCTCGTCCTC
         1210              1230              1250
   TGGCCCCAGCTCAGTCCTGTCCATCTCCAGCTCTAACCATTTGTGGCCCGACACTGGCTC
         1270              1290              1310
   TCCCTCTACCTTCTGTCCTTGTCTGACACTGGTCTCCCGTGCTCTGGGGTCTCTGCACTG
         1330              1350              1370
   ATGGCTGCCTCCCGCTTCTCTCCCCTCTCCCTCTGCCGTCCTGTCTCCTGTGGCCAGTCT
         1390              1410              1430
   CTCCTTGTTTCTCTTCTCCTCCTTCCTTCTCTCCACCTCCCCATAGCCGAGCTTGGAAAA
         1450              1470              1490
   GTCAGACAGACCTCTGAGGTCTCATCCTGGAGCTGCCACCAGCCCAGCCTCCCTGGGACC
         1510              1530              1550
   TGTCTTCACTGCCTGGGGCCCTGGGAGCCAGGGAGGCTCCCTGAGGCTGAGTGAACACTG
         1570              1590              1610
   GGCGCTGCACCTGCCTCTCCCACGTCCTCGGCCCCACTCCCGCAGGTGCAGCTGGCTGGT
         1630              1650              1670
   GACGAAGCCCGGAGCTGGGACCAGCAGCTCCCACTGGGTATGGTGGTTTCTCTCAGGGAG
         1690              1710              1730
   CCTCGTCATCGTCATTGTTTGCTCCACAGTTGGCCTAATCATATGTGTGAAAAGAAGAAA
         1750              1770              1790
   GCCAAGGGGTGATGTAGTCAAGGTGATCGTCTCCGTCCAGGTATTGATCCTCCTCCCCCT
         1810              1830              1850
   CTCCCTCCCCCCTCCACCTTCCCACCTCCCCTCTCCCCGCTGGGGCTGGTGTTTCTGGTG
         1870              1890              1910
   TACATGGTGGGGGCTCCCAGTTCTCTGAGGGTCCTGAGTCTTTCAAGTACAGCCACGGTA
         1930              1950              1970
   GCTCAGGAAAGAACCCACCCCCTCAAACTGAAAGCAGTAAAATGAACCCGAGAACCTGGA
         1990              2010              2030
   GTCCCAGGGGGGCCTGAGCAGGCAGGGTCTCCACGATTCGTGTGCTCACAGCGGGAAAAG
         2050              2070              2090
   ACAGGAGGCAGAAGGTGAGGCCACAGTCATTGAGGCCCTGCAGGCCCCTCCGGACGTCAC
         2110              2130              2150
   CACGGTGGCCGTGGAGGAGACAATACCCTCATTCACGGGGGAGGAGCCCAAACCACTGAC
         2170              2190              2210
   CCACAGACTCTGCACCCCGACGCCAGAGATACCTGGAGCGACGGCTGCTGAAAGAGGCTG
         2230              2250              2270
   TCCACCTGGCGAAACCACCGGAGCCCGGAGGTTTGGGGGCTCCGCCCTGGGCTGGTTTCC
```

FIG.7B

```
           2290                2310                2330
GTCTCCTCCAGTGGAGGGAGAGGTGGGGCCCCTGCTGGGGTAGAGCTGGGGACGCCACGT
           2350                2370                2390
GCCATTCCCATGGGCCAGTGAGGGCCTGGGGCCTCTGTTCTGCTGTGGCCTGAGCTCCCC
           2410                2430                2450
AGAGTCCTGAGGAGGAGCGCCAGTTGCCCCTCGCTCACAGACCACACACCCAGCCCTCCT
           2470                2490                2510
GGGTCCAGCCCAGAGGGCCCTTCAGACCCCAGCTGTCTGCGCGTCTGACTCTTGTGGCCT
           2530                2550                2570
CAGCAGGACAGGCCCCGGGCACTGCCTTCAAGCCAAGGCTGGACTGGGTTGGCTGCAGTG
           2590                2610                2630
TGGTGTTTAGTGGATACCACATCGGAAGTGATTTTCTAAATTGGATTTGAAAAAAAA
```

FIG.7C

```
  1  MLGTSGHLVWLSQGFSL................AGRPGSSPWPVD.....  29
      ::. : :. |. |:.|                 |. |||..: :
  1  .MAPVAVWAALAVGLELWAAAHALPAQVAFTPYAPEPGSTCRLREYYDQT  49

30  AVLACGWC.PGLHV..........................PPLSPSSW  50
     | :.|:.| || |.                            ..||.:|:
 50  AQMCCSKCSPGQHAKVFCTKTSDTVCDSCEDSTYTQLWNWVPECLSCGSR  99

51  TPAMGLRASRNCSRTENAVCGCSPGHFCIVQDGDHCAACRAYATSSPGQR 100
     ... .: ....|.|.:| :|.|.|| :| : ..: |  | :. .:.||
100  CSSDQV.ETQACTREQNRICTCRPGWYCALSKQEGCRLCAPLRKCRPGFG 148

101  VQKGGTESQDTLCQNCPRGPSLPMGPWRNVSTRPSK.............. 136
     |.:.|||. |.:|. |:.|.         ... ::: ..
149  VARPGTETSDVVCKPCAPGTFSNTTSSTDICRPHQICNVVAIPGNASMDA 198
```

FIG.8

```
  1  MEPPGDWGPPPWRSTPKTDVLRLVLYLTFLGAPCYAPALPSCKEDEYPVG   50
     ||||||||||||||||:|||||||||||||||||||||||||||||||||
  1  MEPPGDWGPPPWRSTPRTDVLRLVLYLTFLGAPCYAPALPSCKEDEYPVG   50

51  SECCPKCSPGYRVKEACGELTGTVCEPCPPGTYIAHLNGLSKCLQCQMCD  100

101  PAMGLRAS.RNCSRTENAVCGCSPGHFCIVQDGDHCAACRAYATSSPGQR  149
     |.:|  ... |. :: |.:      :|:: ...:  :....:  |:... |::.
101  PDIGSPCDLRGRGHLEAG......AHLSPGRQKGEPDPEVAFESLSAEPV  144

150  VQKGGTESQDTLCQNCPPGTFSPNGTLEECQHQTKCSWLVTKAGAGTSSS  199
     ..|. . .. : ::. :...:|.    |  .:|::..::.
145  HAANGSVPLEPHARLSMASAPCGQAGLH.........LRDRADGTPGGR  184

200  HWVWWFLSGSLVIVIVCSTVGLIICVKRRKPRGDVVKVIVSVQRKRQEAE  249
```

FIG.10

```
  1  MEPPGDWGPPPWRSTPKTDVLRLVLYLTFLGAPCYAPALPSCKEDEYPVG   50
         .......:::| :..: | |. .|          :||:
  1  ..........MLGTSGHLVWLSQGFSLAGRPGSSP.........WPVD   29

51  SECCPKCSPGYRVKEACGELTGTVCEPCPPGTYIAHLNGLSKCLQCQMCD  100
     .  .. :||.:|          .|  .|:.:
 30  AVLACGWCPGLHV............PPLSPSSW...............T   51

101  PAMGLRASRNCSRTENAVCGCSPGHFCIVQDGDHCAACRAYATSSPGQRV  150
     ||||||||||||||||||||||||||||||||||||||||||||||||||
 52  PAMGLRASRNCSRTENAVCGCSPGHFCIVQDGDHCAACRAYATSSPGQRV  101

151  QKGGTESQDTLCQNCPPGTFSPNGTLEECQHQTKCSWLVTKAGAGTSSSH  200
     ||||||||||||||.|. | |.: :.   |:.|
102  QKGGTESQDTLCQNCPRGPSLPMGPWRNV...STRPSK...........  136
```

FIG.11

```
  1  MEPPGDWGPPPWRSTPRTDVLRLVLYLTFLGAPCYAP.......ALPSCK    43
            .........:::|   :.: | |. .|       | ..|.
  1  ...........MLGTSGHLVWLSQGFSLAGRPGSSPWPVDAVLACGWCP    38

44  EDEYPVGSECCPKCSPGYRVKEACGELTGTVCEPCPPGTYIAHLNGLSKC    93
      : . |. |..::  ... |.|.. .|:   ...||:..|.  :|  :.: ..|
 39  GLHVPPLSPSSWTPAMGLRASRNCSRTENAVCGCSPGHFCI...VQDGDHC   86

94  LQCQMCDPDIGSPCDLRGRGHLEAGAHLSPGRQKGEPDPEVAFESLSAEP   143
      .|. :...  :||.:  .:|  |... |:.. .:|.. |  .:: .:|. |
 87  AACRAYAT...SSPGQRVQKGGTESQDTLCQNCPRGPSLPMGPWRNVSTRP  134

144  VHAAGNSVPLEPHARLSMASAPCGQAGLHLRDRADGTPGGRA.   185
       .                                        |
135  SK.........................................   136
```

FIG.12

```
  1   .........GCACGAGCTGCCTCCCGCAGGCGCCACCTGTGTCCCCCAGCG   42
            ||   |||||||  |||  ||||||||||||||| |||||||
101   TTGCCTGGACAGCTCCTGCCTCAGGCA.GCGCCACCTGTGTCGCCCAGCG  149

43   CCGCTCCACCCAGCAGGCCTGAGCCCCTCTCTGCTGCCAGACACCCCTG   92
      |||||||||||||||||||||||||||||||||||||||||||||||||
150   CCGCTCCACCCAGCAGGCCTGAGCCCCTCTCTGCTGCCAGACACCCCTG  199

93   CTGCCCACT.CTCCTGCTGCTCGGGTTCTGAGGCACAGCTTGTCACACCG  141
      ||||||||| |||||||||||||||||||||||||||||||||||||||
200   CTGCCCACTACTCCTGCTGCTCGGGTTCTGAGGCACAGCTTGTCACACCG  249

142   AGGCGGATTCTCTTTCTCTTTCTCTTTCTCTTCTGGCCCACAGCCGCAGC  191
      ||||||||||||||||||||||||||||||||||||||||||||||||||
250   AGGCGGATTCTCTTTCTCTTTCTCTTTCTCTTCTGGCCCACAGCCGCAGC  299

192   AATGGCGCTGAGTTCCTCTGCTGGAGTTCATCCTGCTAGCTGGGTTCCCG  241
      ||||||||||||||||||||||||||||||||||||||||||||||||||
300   AATGGCGCTGAGTTCCTCTGCTGGAGTTCATCCTGCTAGCTGGGTTCCCG  349

242   AGCTGCCGGTCTGAGCCTGAGGCATGGAGCCTCCTGGAGACTGGGGGCCT  291
      |||||||||||||||||||||| |||||||||||||||||||||||||||
350   AGCTGCCGGTCTGAGCCTGAGTCATGGAGCCTCCTGGAGACTGGGGGCCT  399

292   CCTCCCTGGAGATCCACCCCCAAAACCGACGTCTTGAGGCTGGTGCTGTA  341
      |||||||||||||||||||||| |||||||||||||||||||||||||||
400   CCTCCCTGGAGATCCACCCCCAGAACCGACGTCTTGAGGCTGGTGCTGTA  449

342   TCTCACCTTCCTGGGAGCCCCCTGCTACGCCCCAGCTCTGCCGTCCTGCA  391
      ||||||||||||||||||||||||||||||||||||||||||||||||||
450   TCTCACCTTCCTGGGAGCCCCCTGCTACGCCCCAGCTCTGCCGTCCTGCA  499

392   AGGAGGACGAGTACCCAGTGGGCTCCGAGTGCTGCCCCAAGTGCAGTCCA  441
      ||||||||||||||||||||||||||||||||||||||||||||||||||
500   AGGAGGACGAGTACCCAGTGGGCTCCGAGTGCTGCCCCAAGTGCAGTCCA  549

442   GGTTATCGTGTGAAGGAGGCCTGCGGGGAGCTGACGGGCACAGTGTGTGA  491
      ||||||||||||||||||||||||||||||||||||||||||||||||||
550   GGTTATCGTGTGAAGGAGGCCTGCGGGGAGCTGACGGGCACAGTGTGTGA  599
```

FIG.13A

```
492   ACCCTGCCCTCCAGGCACCTACATTGCCCACCTCAATGGCCTAAGCAAGT   541
      ||||||||||||||||||||||||||||||||||||||||||||||||||
600   ACCCTGCCCTCCAGGCACCTACATTGCCCACCTCAATGGCCTAAGCAAGT   649

542   GTCTGCAGTGCCAAATGTGTGAC...........................   564
      |||||||||||||||||||||||
650   GTCTGCAGTGCCAAATGTGTGACCCAGATATTGGTTCCCCCTGTGACCTC   699

565   ...............CCAGCCATGGGCCTGCGCGCGAGCCGGAACTGCTC   599
                     |||||||||||||||||||||||||||||||||||
1600  CCCTCCTCTTGGACTCCAGCCATGGGCCTGCGCGCGAGCCGGAACTGCTC   1649

600   CAGGACAGAGAACGCCGTGTGTGGTTGCAGCCCAGGCCACTTCTGCATCG   649
      |||||||||||||||||||||||||| |||||||||||||||||||||||
1650  CAGGACAGAGAACGCCGTGTGTGGCTGCAGCCCAGGCCACTTCTGCATCG   1699

650   TCCAGGACGGGGACCACTGCGCCGCGTGCCGCGCTTACGCCACCTCCAGC   699
      ||||||||||||||||||||||||||||||||||||||||||||||||||
1700  TCCAGGACGGGGACCACTGCGCCGCGTGCCGCGCTTACGCCACCTCCAGC   1749

700   CCGGGCCAGAGGGTGCAGAAGGGAGGCACCGAGAGTCAGGACACCCTGTG   749
      ||||||||||||||||||||||||||||||||||||||||||||||||||
1750  CCGGGCCAGAGGGTGCAGAAGGGAGGCACCGAGAGTCAGGACACCCTGTG   1799

750   TCAGAACTGCCCCCCGGGGACCTTCTCTCCCAATGGGACCCTGGAGGAAT   799
      ||||||||||||||||||||||||||||||||||||||||||||||||||
1800  TCAGAACTGCCCCCCGGGGACCTTCTCTCCCAATGGGACCCTGGAGGAAT   1849

800   GTCAGCACCAGACCAAGTG...............................   818
      ||||||||||||||||| ||
1850  GTCAGCACCAGACCAATTGGCCTAATCATATGTGTGAAAAGAAGAAAGCC   1899

819   CAGCTGGCTGGTGACGAAGGCCGGAGCTGGG.........ACCAGCAGCTC   860
      || |   |   |||  ||||  ||  |||           ||||| |
1900  AAGGGGTGAGCACACGGTGGCCCCATCAGGGTTCATGTCCCCAGCCGTCA   1949

861   CCACTGGGTATGGTGGTTTCTCTCAGGGAGCCTCGTCATCGTCATTGTTT   910
      ||  ||  ||     ||    ||    |      |       |   |||
1950  CCTCTTGGAGCTCTGTCACCCCAAGCCTGGGAGGTGGCCCCAGAGCTTTT   1999
```

FIG.13B

```
911   GCTCCACAGTTGGCCTAATCATATGTGTGAAAAGAAGAAAGCCAAGGGGT   960
       |  |   |||    |    |     |  ||   |       ||
2000  CCAGGATCCGCGGCTCCTCCCAGGGCAGCCACTGCAGGCTGGGGCAGGTG   2049

961   GATGTAGTCAAGGTGATCGTCTCCGTCCAGCGG.AAAAGACAGGAGGCAG   1009
      |||||||||||||||||||||||||||||||||| |||||||||||||||
2050  TATGTAGTCAAGGTGATCGTCTCCGTCCAGCGGTAAAAGACAGGAGGCAG   2099

1010  AAGGTGAGGCCACAGTCATTGAGGCCCTGCAGGCCCCTCCGGACGTCACC   1059
      |||||||||||||||||||||| |||||||||||||||||||||||||||
2100  AAGGTGAGGCCACAGTCATTGA.GCCCTGCAGGCCCCTCCGGACGTCACC   2148

1060  ACGGTGGCCGTGGAGGAGACAATACCCTCATTCACGGGGAGGAGCCCAAA   1109
      ||||||||||||||||||||||||||||||||||||||||||||||||||
2149  ACGGTGGCCGTGGAGGAGACAATACCCTCATTCACGGGGAGGAGCCCAAA   2198

1110  CCACTGACCCACAGACTCTGCACCCCGACGCCAGAGATACCTGGAGCGAC   1159
      |||||||||||||||||||||||||||||||||||||||||||||| |||
2199  CCACTGACCCACAGACTCTGCACCCCGACGCCAGAGATACCTGGAGAGAC   2248

1160  GGCTGAATGAAAGAGGCTGTCCACCTGGCGGAACCACCGGAGCCCGGAGG   1209
      |||||  |||  ||||||||||||||||||| ||||||||||||||||||
2249  GGCTG.CTGATAGAGGCTGTCCACCTGGCGAAACCACCGGAGCCCGGAGG   2297

1210  CTTGGGGGCTCCACCCTGGACTGGCTTCCGTCTCCTCCAGTGGAGGGAGA   1259
      |||||||||||| ||||||| |||| ||||||||||||||||||||||||
2298  CTTGGGGGCTCCGCCCTGGGCTGGTTTCCGTCTCCTCCAGTGGAGGGAGA   2347

1260  GGTGGCGCCCCTGCTGG.GGTAGAGCTGGGGACGCCACGTGCCATTCCCA   1308
      ||||| |||||||||||| |||||||||||||||||||||||||||||||
2348  GGTGGTGCCCCTGCTGGTGGTAGAGCTGGGGACGCCACGTGCCATTCCCA   2397

1309  TGGGCCAGTGAGGGCCTGG.GGCCTCTGTTCTGCTGTGGCCTGAGCTCCC   1357
      |||  ||||||||| |||| ||||||||||||||||||||||||||||||
2398  TGGTTCAGTGAGGGGCTGGTGGCCTCTGTTCTGCTGTGGCCTGAGCTCCC   2447

1358  CAGAGTCCTGAGGAGGAGCGCCAGTTGCCCCTCGCTCACAGACCACACAC   1407
      |||||||||||||||||||| |||||||||||||||||||||||||||||
2448  CAGAGTCCTGAGGAGGAGCCCCAGTTGCCCCTCGCTCACAGACCACACAC   2497
```

FIG.13C

```
1408  CCAGCCCTCCTGGGCCAACCCAGAGG.GCCTTCAGACCCCAGCTGTGTGC  1456
      |||||||||||||||||||||||||| ||||||||||||||||||| |||
2498  CCAGCCCTCCTGGGCCAACCCAGAGGCCCCTTCAGACCCCAGCTGTCTGC  2547

1457  GCGTCTGACTCTTGTGGCCTCAGCAGGACAGGCCCCGGGCACTGCCTCAC  1506
      ||||||||||||||||||||||||||||||||||||||||||||||||||
2548  GCGTCTGACTCTTGTGGCCTCAGCAGGACAGGCCCCGGGCACTGCCTCAC  2597

1507  AGCCAAGGCTGGACTGGGTTGGCTGCAGTGTGGTGTTTAGTGGATACCAC  1556
      |||||||||||| |||||||||||||||||||||||||||||||||||||
2598  AGCCAAGGCTGGAATGGGTTGGCTGCAGTGTGGTGTTTAGTGGATACCAC  2647

1557  ATCGGAAGTGATTTTCT...AAATTGGATTTGAATTCGGCTCCTGTTTTCT  1604
      |||||||||||||||||   |||||||||||||||||||||
2648  ATCGGAAGTGATTTTCTAAAAATTGGATTTGAATTCGGAAAAAAA.....  2692
```

FIG.13D

```
   1 ........................GCACGAGCTGCCTCCCGCAGGCGC   24
                             | | ||| |         | | |
 701 GTTGCTTCCCTGGGAGATGACCGTCTTCTCCAGCAGAAAGGTTGAAGGTC  750

25 CACCTGTGTCCCCCAGCGCCGCTCCACCCAGCAGGCCTGAGCCCCTCTCT   74
     | |  || |  ||  |   |  || |   | || |      ||
 751 CCACCCTGAGCGGCACCCTGGTCACATGCCTGCGTCCAGGAGAGCTGCAG  800

75 GCTGCCAGACACCCCCTGCTGCCCACTCTCCTGCTGCTCGGGTTCTGAGG  124
     | ||         |  |  ||       || |      |  ||
 801 GGTGAAGCCTGTGTGCCCCAGATAACCCCTTCCATGGGCCCAGACAAAGC  850

125 CACAGCTTGTCACACCGAGGCGGATTCTCTTTCTCTTTCTCTTTCTCTTC  174
     | ||  |   ||  |   |||  |||      |   ||           |
 851 CTCATCAGATCTGAGCTTCCTGGAGGCTCAGGATGGGCCTTCCCAGAAGC  900

175 TGGCCCACA.....GCCGCAGCAATGGCGCTGAGTTCCTCTGCTGGAGTT  219
     ||||||  |       || ||  || |  | |        |||   | |
 901 AGGCCCAGAGGGAGGCTGCCTCCAGATCCCCTGTCCCCTGGGGCTGTGGG  950

220 CATCCTGCTAGCTGGGTTCCCGAGCTGCCGGTCTGAGCCTGAGGCATGGA  269
     |||      |   |  ||  | |         |||  || | |||  | |
 951 TGTCCCTGAATGTCAGGGCCATGGGAGGGCCCCTGGGCTTCAGGGGTTGG 1000

270 GCCTCCTGGAGACTGGGGGGCCTCCTCC......CTGGAGATCCACCCCCAA 314
     |    || | |||  |  |  |||           |  ||||  | ||| |||
1001 GGAAAGTGAACACTCTGCTCTTTGTCCACCTTCGGGAGGACAACCTTCAA 1050

315 A.......ACCGACGTCTTGAGGCTGGTGCTGTATCTCACCTTCCTGGGA  357
     |         |     |   ||   ||    ||  |||||  |||||
1051 ATGCTGACCCTGGGCCCCTAACTGACCTGAGACTTCAGAGCTTCTTGGGA 1100

358 GCCCCCTGCTACGCCCCAGCTCTGCCGTCCTGCAAGGAGGACGAGTACCC  407
     |    | |  |||         | ||   ||    ||| |  |  |||
1101 GGAGCTGGGGTCCCCCAGCGGAGCCTGGGATGGAGCAGGGATGGCTGCCC 1150

408 AGTGGGCTCCGAGTGCTGCCCCAAGTGCAGTCCAGGTTATCGTGTGAAGG  457
     ||    |   |  |     |  |  |    |    |  || |
1151 CAGGGAGGGGGCGGTGGGGCCTTCCATCCTGCTCTGCCCTCCTCGTCCTC 1200
```

FIG.14A

```
458   AGG...CCTGCGGGGAGCTGACGGGCACAGTGTGTGAACCCTGCCCTCCAG    505
      ||  || ||    |  ||| |  ||    | | |     |       ||  |
1201  TGGCCCCAGCTCAGTCCTGTCCATCTCCAGCTCTAACCATTTGTGGCCCG   1250

506   GCACCTACATTGCCCACCTCAATGGCCTAAGCAAGTGTCTGCAGTGCC...   553
      |||   |  |||       |     ||    | |   |    |||   | ||
1251  ACACTGGCTCTCCCTCTACCTTCTGTCCTTGTCTGACACTGGTCTCCCGT   1300

554   AAATGTGTGACCCAGCCATGGGCCTGCGCGCGAGCCGGAACTGCTCCAG     602
      || |    |      |      | ||||    |         |  |||
1301  GCTCTGGGGTCTCTGCACTGATGGCTGCCTCCCGCTTCTCTCCCCTCTCC   1350

603   GACAGAGAACGCCGTGTGTGGTTGCAGCCCAGGCCACTTCTGCATCGTCC    652
      | |   |      ||   ||| |  |   |    |  ||    | ||  |
1351  CTCTGCCGTCCTGTCTCCTGTGGCCAGTCTCTCCTTGTTTCTCTTCTCCT   1400

653   AGGACGGGGACCACTGCGCCGCGTGCCGCGCTTACGCCACCTCCAGCCCG    702
      |      |    |  | | |||   |  |    | |  |  |  ||  |
1401  CCTTCCTTCTCTCCACCTCCCCATAGCCGAGCTTGGAAAAGTCAGACAGA   1450

703   GGCCAGAGGGTGCAGAAGGGAGGCACCGAGAGTCAGGACACCCTGTGTCA    752
      |  ||||   ||    ||||  || ||  |  | | || |||||| | |
1451  CCTCTGAGGTCTCATCCTGGAGCTGCCACCAGCCCAGCCTCCCTGGGACC   1500

753   GAACTGCCC...CCCGGGGGACCTTCTCTCCCAATGGGACCCTGGAGG....   796
      ||  |  || |  || |||| |||   ||    ||  ||   |   ||||
1501  TGTCTTCACTGCCTGGGGCCCTGGGAGCCAGGGAGGCTCCCTGAGGCTGA   1550

797   ..............................AATGTCAGCACCAG         810
                                    |  |  |||
1551  GTGAACACTGGGCGCTGCACCTGCCTCTCCCACGTCCTCGGCCCCACTCC   1600

811   ACCAAGTGCAGCTGGCTGGTGACGAAGGCCGGAGCTGGGACCAGCAGCTC    860
      || |||||||||||||||||||||||| ||||||||||||||||||||||
1601  CGCAGGTGCAGCTGGCTGGTGACGAAGCCCGGAGCTGGGACCAGCAGCTC   1650

861   CCACTGGGTATGGTGGTTTCTCTCAGGGAGCCTCGTCATCGTCATTGTTT    910
      ||||||||||||||||||||||||||||||||||||||||||||||||||
1651  CCACTGGGTATGGTGGTTTCTCTCAGGGAGCCTCGTCATCGTCATTGTTT   1700
```

FIG. 14B

```
911   GCTCCACAGTTGGCCTAATCATATGTGTGAAAAGAAGAAAGCCAAGGGGT  960
      ||||||||||||||||||||||||||||||||||||||||||||||||||
1701  GCTCCACAGTTGGCCTAATCATATGTGTGAAAAGAAGAAAGCCAAGGGGT  1750

961   GATGTAGTCAAGGTGATCGTCTCCGTCCAG....................  990
      ||||||||||||||||||||||||||||||
1751  GATGTAGTCAAGGTGATCGTCTCCGTCCAGGTATTGATCCTCCTCCCCCT  1800

991   ...........................CGGAAAAGACAGGAGGCA  1008
                                 |||||||||||||||||||
2001  GGCAGGGTCTCCACGATTCGTGTGCTCACAGCGGGAAAAGACAGGAGGCA  2050

1009  GAAGGTGAGGCCACAGTCATTGAGGCCCTGCAGGCCCCTCCGGACGTCAC  1058
      ||||||||||||||||||||||||||||||||||||||||||||||||||
2051  GAAGGTGAGGCCACAGTCATTGAGGCCCTGCAGGCCCCTCCGGACGTCAC  2100

1059  CACGGTGGCCGTGGAGGAGACAATACCCTCATTCAC.GGGGAGGAGCCCA  1107
      |||||||||||||||||||||||||||||||||||| |||||||||||||
2101  CACGGTGGCCGTGGAGGAGACAATACCCTCATTCACGGGGGAGGAGCCCA  2150

1108  AACCACTGACCCACAGACTCTGCACCCCGACGCCAGAGATACCTGGAGCG  1157
      ||||||||||||||||||||||||||||||||||||||||||||||||||
2151  AACCACTGACCCACAGACTCTGCACCCCGACGCCAGAGATACCTGGAGCG  2200

1158  ACGGCTGAATGAAAGAGGCTGTCCACCTGGCGGAACCACCGGAGCCCGGA  1207
      ||||||| ||||||||||||||||||||||||| ||||||||||||||||
2201  ACGGCTG.CTGAAAGAGGCTGTCCACCTGGCGAAACCACCGGAGCCCGGA  2249

1208  GGCTTGGGGGCTCCACCCTGGACTGGCTTCCGTCTCCTCCAGTGGAGGGA  1257
      || |||||||||| |||||| |||| ||||||||||||||||||||||||
2250  GGTTTGGGGGCTCCGCCCTGGGCTGGTTTCCGTCTCCTCCAGTGGAGGGA  2299

1258  GAGGTGGCGCCCCTGCTGGGGTAGAGCTGGGGACGCCACGTGCCATTCCC  1307
      ||||||| ||||||||||||||||||||||||||||||||||||||||||
2300  GAGGTGGGGCCCCTGCTGGGGTAGAGCTGGGGACGCCACGTGCCATTCCC  2349

1308  ATGGGCCAGTGAGGGCCTGGGGCCTCTGTTCTGCTGTGGCCTGAGCTCCC  1357
      ||||||||||||||||||||||||||||||||||||||||||||||||||
2350  ATGGGCCAGTGAGGGCCTGGGGCCTCTGTTCTGCTGTGGCCTGAGCTCCC  2399
```

FIG.14C

```
1358  CAGAGTCCTGAGGAGGAGCGCCAGTTGCCCCTCGCTCACAGACCACACAC  1407
      ||||||||||||||||||||||||||||||||||||||||||||||||||
2400  CAGAGTCCTGAGGAGGAGCGCCAGTTGCCCCTCGCTCACAGACCACACAC  2449

1408  CCAGCCCTCCTGGG.CCAACCCAGAGGG.CCTTCAGACCCCAGCTGTGTG  1455
      |||||||||||||  |||  |||||||||  ||||||||||||||||| ||
2450  CCAGCCCTCCTGGGTCCAGCCCAGAGGGCCCTTCAGACCCCAGCTGTCTG  2499

1456  CGCGTCTGACTCTTGTGGCCTCAGCAGGACAGGCCCCGGGCACTGCCTCA  1505
      ||||||||||||||||||||||||||||||||||||||||||||||||||
2500  CGCGTCTGACTCTTGTGGCCTCAGCAGGACAGGCCCCGGGCACTGCCTTC  2549

1506  CAGCCAAGGCTGGACTGGGTTGGCTGCAGTGTGGTGTTTAGTGGATACCA  1555
      ||||||||||||||||||||||||||||||||||||||||||||||||||
2550  AAGCCAAGGCTGGACTGGGTTGGCTGCAGTGTGGTGTTTAGTGGATACCA  2599

1556  CATCGGAAGTGATTTTCTAAATTGGATTTGAATTCGGCTCCTGTTTTCTA  1605
      |||||||||||||||||||||||||||||||
2600  CATCGGAAGTGATTTTCTAAATTGGATTTGAAAAAAAA............  2637
```

FIG.14D

```
  1  CCCCCTTCTACAGGAAACCCGGAGTGGACTGGAACGGTGCAGGGGGAGAA   50
        ||   |    ||||  |   |||  |    |       |   | | |
  1  ...AAAGCTCGGGCTCCACCGGGGACGACCGCTCCTAGAAACTGAGTGGT   47

51  CTCGCCCCTCCCATCGGGCGCCTCCTTCATACCGGCCCTTCCCCTCGGCT  100
     || |||   ||  |  ||    |||  |  ||| |   | ||     ||||   ||
 48  ATCCCCCGGGCCTGCAGG.AATTCCAACCTGCCTGAAGGGACCCTGCCCT   96

101  TTGCCTGGACAGCTCCTGCCTCAGGCAGCGCCACCTGTGTCGCCCAGCGC  150
      |||          | |     |||  |         | | | ||        ||
 97  GGAACTG..ACAGTGCAAGCTCGGCGTCCTGCCCATCTGGGAAGAAGGCT  144

151  CGCTCCACCCAGCAGGCCTGAGCCCCTCTCTGCTGCCAGACACCCCCTGC  200
     | | | ||||  ||    |  | ||      || || |  | |||    |
145  GGTTTCTCCCATCAACGAAGCCCTCCCAGGACCTTCCTGCAAGCCCTCGT  194

201  TGCCCACTACTCCTGCTGCTCGGGTTCTGAGGCACAGCTTGTCACACCGA  250
      |  |||      |     ||   |   |  ||   |      |||   |
195  CCCACACGCAGCTCTGCCGTCCCTTGGTGTCCCTCCCGGCCTCA...GGT  241

251  GGCGGATTCTCTTTCTCTTTCTCTTTCTCTTCTGGCCCA.CAGCCGCAGC  299
      ||  ||    |   |||     |||| ||||   | |     |    |
242  CCTCCATGCTGGGTACCTCTGGGCACCTCGTTTGGCTGAGCCAGGGGTTC  291

300  AATGGCGCTGAGTTCCTCTGCTGGAGTTCATCCTGCTAGCTGGGTTCCCG  349
      |    || | | ||   ||  || | |||| |   |          | | ||
292  AGCCTGGCAGGGCGCCCTGGCAGCAGTCCTTGGCCTGTGGATGCTGTCCT  341

350  AGCTGCCGGTCTGAGCCTGAGTCATGGAGCCTCCTGGAGACTGGGGGCCT  399
      ||   ||   |||      |  | || |     ||     |||
342  GGCCTGTGGATGGTGTC.....CCGGCCTCCACGTACCCCCTCTCAGCCC  386

400  CCTCCCTGGAGATCCACCCCCAGAACGACGTCTTGAGGCTGGTGCTGTA   449
      | ||| |     |||| ||  |  |            |   |    ||||    |
387  CTCCTCTTGGACTCCAGCCATGGGCCTGCGCGCGAGCCGGAACTGCTCCA  436

450  TCTCACCTTCCTGGGAGCCCCCTGCTACGCCCCAGCTCTGCCG.TCCTGC  498
      ||    |    | |     | ||        | ||  | | | |  | |
437  GGACAGAGAACGCCGTGTGTGGCTGCAGCCCAGGCCACTTCTGCATCGTC  486
```

FIG.15A

```
499  AAGGAGGACGAGTACCCAGTGGGCTCCGAGTGCTGCCCCAAGTGCAGTCC  548
     ||||  | ||  ||   |    |  ||     |  |||  |  ||| ||
487  CAGGACGGGGACCACTGCGCCGCGTGCCGCGCTTACGCCACCTCCAGCCC  536

549  AGGTTATCGTGTGAAGGAGGCCTGCGGGGAGCTGACGGGCACAGTGTGTG  598
     ||  |  |  |||  || |||   ||   |||    || |||  |||||
537  GGGCCAGAGGGTGCAGAAGGGAGGCACCGAGAGTCAGGACACCCTGTGTC  586

599  AACCCTGCCCTCCAGGCACCTACATTGCCCACCTCAATGGCCTAAGCAAG  648
     |   ||||||  | ||   |   ||||   |        |   | | |
587  AGAACTGCCCCCGGGGACCTT...CTCTCCCAATGGGACCCTGGAGGAATG  634

649  TGTCTGCAGTGCCAAATGTGTGACCCAGATATTGGTTCCCCCTGTGACCT  698
     |     |  ||||   ||||  ||  |     ||     |  ||||| |||
635  TCAGCACCAGACCAAGTAAGTGAACCCGGGGGAGGCCAGCTCTGTGCCCT  684

699  CAGGGGAAGAGGTCACCTGGAGGCTGGTGCCCACCTGAGTCCAGGCAGAC  748
     ||  |     ||| ||   |   |    |     |   |||    |   |
685  GGGGAGGGGGCTCCACGTTGCTTCCCTGGGAGATGACCGTCTTCTCCAGC  734

749  AGAAAGG.....GGAACCAGACCCAGAGGTGGCCTTTGAGTCACTGAGCG  793
     |||||||        || |||  | ||  |||                |||
735  AGAAAGGTTGAAGGTCCCACCCTGAGCGGCACCCTGGTCACATGCCTGCG  784

794  CAGAGCCTGTCCATGCGGCCAACGGCTCTGTCCCCTTGGAGCCTCATGCC  843
     ||    |  ||   ||       ||||    | ||  |  |
785  TCCAGGAGAGCTGCAGGGTGAAGCCTGTGTGCCCCAGATAACCCCTTCCA  834

844  AGGCTCAGCATGGCCAGTGCTCCCTGCGGCCAGGCAGGACTGCACCTGCG  893
     ||   |      |  ||  ||     |   |   ||  |
835  TGGGCCCAGACAAAGCCTCATCAGATCTGAGCTTCCTGGAGGCTCAGGAT  884

894  GGACAGGGCTGACGGCACACCTGGGGGCAGGGCCTGAGCCTACAGGGAGG  943
     ||  |    |||   ||  | |||  |   | |
885  GGGCCTTCCCAGAAGCAGGCCCAGAGGGAGGCTGCCTCCAGATCCCCTGT  934

944  CACAGGGCAGGTGGGCTAGCCATGAACAGAAGAGGAAGCTGGAGTGCTTT  993
     |  |  |      ||   ||  ||.||||   ||| |    |    |  |
935  CCCCTGGGGCTGTGGGTGTCCCTGAATGTCAGGGCCATGGGAGGGCCCCT  984
```

FIG.15B

```
994   GGGGGTTCATGCATGTAGGCTGGGATTTGGGGCTCACACCTCAACCTGCA  1043
      |||  |    |  || |  ||              || |||| |
985   GGGCTTCAGGGGTTGGGGAAAGTGAACACTCTGCTCTTTGTCCACCTTCG  1034

1044  TGCCCAGTTCCATGCCCCTCCCCTCTTGTGAAAGCACCTGTCTACTTGGG  1093
      |  |  ||  |       |   ||| |     |  |
1035  GGAGGACAACCTTCAAATGCTGACCCTGGGCCCCTAACT.........GA  1075

1094  CTGAGGATGTGGGGGCACAGGTGGCAGGTGAGGCTGCCCTCAGGAGGGGC  1143
      |   || |  | ||        || |      ||   ||| |||  | |
1076  CCTGAGACTTCAGAGCTTCTTGGGAGGAGCTGGGGTCCCCAGCGGAGCC  1125

1144  CCAGGCCCAGCTTGTACCCCACCTCCACCAGTACCTGAAGAAGTGGGGCT  1193
       |  |||  | |   |  |||        ||| | ||
1126  TGGGATGGAGCAGGGATGGCTGCCCCA........GGGAGGGGGCGGTGG  1167

1194  CTCACCCTACCTGCCTCTGCCATTGGAATGGCCTGGTTTGCACAGATGGG  1243
      |   |||  ||||||| |    |   ||||    | |
1168  GGCCTTCCATCCTGCTCTGCCCTCCTCGTCCTCTGGCCCCAGCTCAGTCC  1217

1244  AAACCCGTTTGAGGGGTGGGTGTCTGGGTGGGCACGTGGGGCGAGGACCT  1293
      ||  |  ||  |    | ||   ||   ||   ||           ||
1218  TGTCCATCTCCAGCTCTAACCATTTGTGGCCCGACACTGGCTCTCCCTCT  1267

1294  GCCTGAGGGACCCTGCCCTGGAACTGACAGTGCAAGCTCGGCGTCCTGCC  1343
      |||   |   |                  |    || ||    ||||
1268  ACCTTCTGTCCTTGTCTGACACTGGTCTCCCGTGCTCTGGGGTCTCTGCA  1317

1344  CATCTGGGCAGAAGGCTGGTTTCTCCCATCAACGAAGCCCTCCCAGGACC  1393
       |   |||            |  | |||||| ||   ||  || |    |
1318  CTGATGGCTGCCTCCCGCTTCTCTCCCCTCTCCCTCTGCCGTCCTGTCTC  1367

1394  TTCCTGCAAGCCCTCGTCCCACACGCAGCTCTGCCGTCCCTTGGTGTCCC  1443
       |  || ||   |            | |  ||| || |||  |      ||
1368  CTGTGGCCAGTCTCTCCTTGTTTCTCTTCTCCTCCTTCCTTCTCTCCACC  1417

1444  TCCCGGCCTCAGGTCCTCCA....TGCTGGGTACCTCTGGGCACCTCGTT  1489
      ||||    |  | |    |     |       |||||||| |  |
1418  TCCCCATAGCCGAGCTTGGAAAAGTCAGACAGACCTCTGAGGTCTCATCC  1467
```

FIG. 15C

```
1490  TGGCTGAGCCAGGGGTTCAGCCTGGCAGGGCGCCCTGGCAGCAGTCCTTG  1539
      |||  ||||   |  ||||||| | |||  |  |        |||    |
1468  TGGAGCTGCCACCAGCCCAGCCTCCCTGGGACCTGTCTTCACTGCCTGGG  1517

1540  GCCTGTGGATGCTGTCCTGGCCTGTG.GATGGTGTCCCGCCCTCCACGTA  1588
      |||   |||  |  ||        | | || |   ||| |          |
1518  GCCCTGGGAGCCAGGGAGGCTCCCTGAGGCTGAGTGAACACTGGGCGCTG  1567

1589  CCCCTCTCACCCCCTCCTCTTGGACTCCAGCCATGGGCCTGCGCGCGAGC  1638
      | |||  | | ||| || | | |||                    |  ||
1568  CACCTGCCTCTCCCACGTCCTCGGCCCCA..............CTCCCGC  1603

1639  CGGAACTGCTCCAGGACAGAGAACGCCGTGTGTGGCTGCAGCCCAGGCCA  1688
      ||  | |||    |    |||  |||   |||   ||||       |||
1604  AGGTGCAGCTGGCTGGTGACGAAGCCCGGAGCTGGGACCAGCAGCTCCCA  1653

1689  CTTCTGCATCGTCCAGGACGGGGACCACTGCGCCGCGTGCCGCGCTTACG  1738
      ||             |   |   | |||   |   | ||  |
1654  CTGGGTATGGTGGTTTCTCTCAGGGAGCCTCGTCATCGTCATTGTTTGCT  1703

1689  CCACCTCCAGCCCGGGGCCAGAGGGTGCAGAAGGGAGGCACCGAGAGTCAG  1788
      ||||    |||           | ||||| |  ||     |    | |||
1704  CCACAGTTGGCCTAATCATATGTGTGAAAAGAAGAAAGCCAAGGGGTGAT  1753

1789  GACACCCTGTGTCAGAACTGCCCCCCGG...GGACCTTCTCTCCCAATGG  1835
      |   |   |     || | ||     || || |  |||
1754  GTAGTCAAGGTGATCGTCTCCGTCCAGGTATTGATCCTCCTCCCCCTCTC  1803

1836  GACCCTGGAGGAATGTCAGCACCAGACCAATTGGCCTAATCATATGTGTG  1885
      ||       |  |   ||||  ||   |           ||||
1804  CCTCCCCCCTCCACCTTCCCACCTCCCCTCTCCCCGCTGGGGCTGGTGTT  1853

1886  AAAAGAAGAAAGCCAAGGGG...TGAGCACACGGTGGCCCCATCAGGGTT  1932
           | |    ||||   || | | ||  ||        ||
1854  TCTGGTGTACATGGTGGGGGCTCCCAGTTCTCTGAGGGTCCTGAGTCTTT  1903

1933  CATGTCCCCAGCCGTCACCTCTTGGAGCTCTGTCACCCCAAGCCTGGGAG  1982
      || || |    ||   |||  ||     |  | | | |||| ||    |
1904  CAAGTACAGCCACGGTAGCTCAGGAA......AGAACCCACCCCCTCAAA  1947
```

FIG.15D

```
1983  GTGGCCCCAGAGCTTTTCCAGGATCCGCGGCTCCTCCCAGGGCAGCCACT  2032
      ||  |||   |          |        ||||||||  |||
1948  CTGAAAGCAGTAAAATGAACCCGAGAACCTGGAGTCCCAGGGGGGCCTGA  1997

2033  GCAGGCTGGGGCAGGTGTATGTAGTCAAGGTGATCGTCTCCGTCCAGCGG  2082
      ||||||  ||| |         ||          ||||  | |  |||||
1998  GCAGGCAGGGTCTCCACGAT............TCGTGTGCTCACAGCGG  2034

2083  TAAAAGACAGGAGGCAGAAGGTGAGGCCACAGTCATTGA.GCCCTGCAGG  2131
      ||||||||||||||||||||||||||||||||||||||| |||||||||
2035  GAAAAGACAGGAGGCAGAAGGTGAGGCCACAGTCATTGAGGCCCTGCAGG  2084

2132  CCCCTCCGGACGTCACCACGGTGGCCGTGGAGGAGACAATACCCTCATTC  2181
      |||||||||||||||||||||||||||||||||||||||||||||||||
2085  CCCCTCCGGACGTCACCACGGTGGCCGTGGAGGAGACAATACCCTCATTC  2134

2182  AC.GGGGAGGAGCCCAAACCACTGACCCACAGACTCTGCACCCCGACGCC  2230
      || |||||||||||||||||||||||||||||||||||||||||||||||
2135  ACGGGGGAGGAGCCCAAACCACTGACCCACAGACTCTGCACCCCGACGCC  2184

2231  AGAGATACCTGGAGAGACGGCTGCTGATAGAGGCTGTCCACCTGGCGAAA  2280
      ||||||||||||  ||||||||||||  |||||||||||||||||||||
2185  AGAGATACCTGGAGCGACGGCTGCTGAAAGAGGCTGTCCACCTGGCGAAA  2234

2281  CCACCGGAGCCCGGAGGCTTGGGGGCTCCGCCCTGGGCTGGTTTCCGTCT  2330
      ||||||||||||||||||| |||||||||||||||||||||||||||||
2235  CCACCGGAGCCCGGAGGTTTGGGGGCTCCGCCCTGGGCTGGTTTCCGTCT  2284

2331  CCTCCAGTGGAGGGAGAGGTGGTGCCCCTGCTGGTGGTAGAGCTGGGGAC  2380
      ||||||||||||||||||||| |||||||||||| |||||||||||||||
2285  CCTCCAGTGGAGGGAGAGGTGGGGCCCCTGCTGG.GGTAGAGCTGGGGAC  2333

2381  GCCACGTGCCATTCCCATGGTTCAGTGAGGGGCTGGTGGCCTCTGTTCTG  2430
      |||||||||||||||||||   |||||||| ||||  |||||||||||||
2334  GCCACGTGCCATTCCCATGGGCCAGTGAGGGCCTGG.GGCCTCTGTTCTG  2382

2431  CTGTGGCCTGAGCTCCCCAGAGTCCTGAGGAGGAGCCCCAGTTGCCCCTC  2480
      |||||||||||||||||||||||||||||||||||| |||||||||||||
2383  CTGTGGCCTGAGCTCCCCAGAGTCCTGAGGAGGAGCGCCAGTTGCCCCTC  2432
```

FIG.15E

```
2481  GCTCACAGACCACACACCCAGCCCTCCTGGG.CCAACCCAGAGGCCCCTT  2529
      ||||||||||||||||||||||||||||||| ||| |||||||| |||||
2433  GCTCACAGACCACACACCCAGCCCTCCTGGGTCCAGCCCAGAGGGCCCTT  2482

2530  CAGACCCCAGCTGTCTGCGCGTCTGACTCTTGTGGCCTCAGCAGGACAGG  2579
      ||||||||||||||||||||||||||||||||||||||||||||||||||
2483  CAGACCCCAGCTGTCTGCGCGTCTGACTCTTGTGGCCTCAGCAGGACAGG  2532

2580  CCCCGGGCACTGCCTCACAGCCAAGGCTGGAATGGGTTGGCTGCAGTGTG  2629
      ||||||||||||||   ||||||||||| |||||||||||||||||||||
2533  CCCCGGGCACTGCCTTCAAGCCAAGGCTGGACTGGGTTGGCTGCAGTGTG  2582

2630  GTGTTTAGTGGATACCACATCGGAAGTGATTTTCTAAAAATTGGATTTGA  2679
      |||||||||||||||||||||||||||||||||||||        |||
2583  GTGTTTAGTGGATACCACATCGGAAGTGATTTTCTAAA........TTGG  2624

2680  ATTCGGAAAAAAAA  2692
      ||| | ||||||||
2625  ATTTGAAAAAAAA   2637
```

FIG.15F

| | | | | | |
|---|---|---|---|---|---|
| TNFR-I | V | C | PQGKYIHPQNNSI | C | TK |
| TNFR-II | T | C | RLREYYDQTAQM | C | SK |
| CD40 | A | C | REKQYLINSQ | C | SL |
| 4-1BB | | | — | | CSN |
| TR-2 | S | C | KEDEYPVGSE | C | PK |

| | | | | |
|---|---|---|---|---|
| TNFR-I | C | HKGTYLYND | C | PGPGQDTD C R |
| TNFR-II | C | SPGQHAKVF | C | TKTSDTV C D |
| CD40 | C | QPGQKLVSD | C | TEPTETE C L |
| 4-1BB | C | PAGTF | C | DNNRNQI C S |
| TR-2 | C | SPGYRVKEA | C | GELTGTV C E |

| | | | | |
|---|---|---|---|---|
| TNFR-I | E C | ESGSFTASENHLRH | LS C SK | C | TVDRDTV C G |
| TNFR-II | S C | EDSTYTQLWNWPE | LS C GSR | C | TREQNRI C T |
| CD40 | P C | GESEFLDTWNRETH | HQ H KY | G | TSETDTI C T |
| 4-1BB | P C | PPNSFSSAGGQRT | DI C RQ | C | SSTSNAE C D |
| TR-2 | P C | PPGTYTAHLNGLSK | LQ C QM | C | SRTENAV C G |

| | | | | | |
|---|---|---|---|---|---|
| TNFR-I | C | RKNQYRHYWSENLFQ | C FN C SL | C | LNGTVHLS C | QEKQNTV C T |
| TNFR-II | C | RPGWY C ALSKQEG | C RL C APLRK | C | RPGFGVARP | G TETSDVV C K |
| CD40 | C | EEGWH C TSEA | C ES C VLHRS | C | SPGFGVKQIAT | G VSDTI C E |
| 4-1BB | C | TPGFH C LGAG | C SM C EQD | C | KQGQELTKKG | C KD C — |
| TR-2 | C | SPGHF C IVQDGDH | AA C RAYAT | S | SPGQRVQKG | G TESQDTL C Q |

| | | | | |
|---|---|---|---|---|
| TNFR-I | — C | HAGFFLRENE | VS C SN | C KKSLE | C TKL |
| TNFR-II | P C | APGTFSNTTSSTDI | RP H QI | C NVVAIP | G NASMDAV C T |
| CD40 | P C | PVGFFSNVSSAFEK | HP W TS | C ETKDLVQQA | G TNKTDVV C G |
| 4-1BB | — C | F-GTFNKQKRGI | RP W TN | C SLDGKSVLVN | G TKERDVV C G |
| TR-2 | N C | PPGTFSPNGTLEE | QH Q TK | C SWLVTKA | G AGTSSSH W V |

FIG.16

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1704 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 265..1113

(ix) FEATURE:
      (A) NAME/KEY: sig_peptide
      (B) LOCATION: 265..372

(ix) FEATURE:
      (A) NAME/KEY: mat_peptide
      (B) LOCATION: 373..1113

(xi) SEQUENCE DESCRIPTION: SEQ ID NO:1:

```
GCACGAGCTG CCTCCCGCAG GCGCCACCTG TGTCCCCCAG CGCCGCTCCA CCCAGCAGGC       60

CTGAGCCCCT CTCTGCTGCC AGACACCCCC TGCTGCCCAC TCTCCTGCTG CTCGGGTTCT      120

GAGGCACAGC TTGTCACACC GAGGCGGATT CTCTTTCTCT TTCTCTTTCT CTTCTGGCCC      180

ACAGCCGCAG CAATGGCGCT GAGTTCCTCT GCTGGAGTTC ATCCTGCTAG CTGGGTTCCC      240

GAGCTGCCGG TCTGAGCCTG AGGC ATG GAG CCT CCT GGA GAC TGG GGG CCT         291
                           Met Glu Pro Pro Gly Asp Trp Gly Pro
                           -36 -35                 -30

CCT CCC TGG AGA TCC ACC CCC AAA ACC GAC GTC TTG AGG CTG GTG CTG        339
Pro Pro Trp Arg Ser Thr Pro Lys Thr Asp Val Leu Arg Leu Val Leu
        -25                 -20                 -15

TAT CTC ACC TTC CTG GGA GCC CCC TGC TAC GCC CCA GCT CTG CCG TCC        387
Tyr Leu Thr Phe Leu Gly Ala Pro Cys Tyr Ala Pro Ala Leu Pro Ser
    -10                 -5                   1                 5

TGC AAG GAG GAC GAG TAC CCA GTG GGC TCC GAG TGC TGC CCC AAG TGC        435
Cys Lys Glu Asp Glu Tyr Pro Val Gly Ser Glu Cys Cys Pro Lys Cys
                 10                  15                  20

AGT CCA GGT TAT CGT GTG AAG GAG GCC TGC GGG GAG CTG ACG GGC ACA        483
Ser Pro Gly Tyr Arg Val Lys Glu Ala Cys Gly Glu Leu Thr Gly Thr
            25                  30                  35

GTG TGT GAA CCC TGC CCT CCA GGC ACC TAC ATT GCC CAC CTC AAT GGC        531
Val Cys Glu Pro Cys Pro Pro Gly Thr Tyr Ile Ala His Leu Asn Gly
        40                  45                  50

CTA AGC AAG TGT CTG CAG TGC CAA ATG TGT GAC CCA GCC ATG GGC CTG        579
Leu Ser Lys Cys Leu Gln Cys Gln Met Cys Asp Pro Ala Met Gly Leu
    55                  60                  65

CGC GCG AGC CGG AAC TGC TCC AGG ACA GAG AAC GCC GTG TGT GGT TGC        627
Arg Ala Ser Arg Asn Cys Ser Arg Thr Glu Asn Ala Val Cys Gly Cys
 70                  75                  80                  85

AGC CCA GGC CAC TTC TGC ATC GTC CAG GAC GGG GAC CAC TGC GCC GCG        675
Ser Pro Gly His Phe Cys Ile Val Gln Asp Gly Asp His Cys Ala Ala
                90                  95                 100

TGC CGC GCT TAC GCC ACC TCC AGC CCG GGC CAG AGG GTG CAG AAG GGA        723
Cys Arg Ala Tyr Ala Thr Ser Ser Pro Gly Gln Arg Val Gln Lys Gly
            105                 110                 115
```

-continued

```
GGC ACC GAG AGT CAG GAC ACC CTG TGT CAG AAC TGC CCC CCG GGG ACC        771
Gly Thr Glu Ser Gln Asp Thr Leu Cys Gln Asn Cys Pro Pro Gly Thr
        120                 125                 130

TTC TCT CCC AAT GGG ACC CTG GAG GAA TGT CAG CAC CAG ACC AAG TGC        819
Phe Ser Pro Asn Gly Thr Leu Glu Glu Cys Gln His Gln Thr Lys Cys
    135                 140                 145

AGC TGG CTG GTG ACG AAG GCC GGA GCT GGG ACC AGC AGC TCC CAC TGG        867
Ser Trp Leu Val Thr Lys Ala Gly Ala Gly Thr Ser Ser Ser His Trp
150                 155                 160                 165

GTA TGG TGG TTT CTC TCA GGG AGC CTC GTC ATC GTC ATT GTT TGC TCC        915
Val Trp Trp Phe Leu Ser Gly Ser Leu Val Ile Val Ile Val Cys Ser
                170                 175                 180

ACA GTT GGC CTA ATC ATA TGT GTG AAA AGA AGA AAG CCA AGG GGT GAT        963
Thr Val Gly Leu Ile Ile Cys Val Lys Arg Arg Lys Pro Arg Gly Asp
            185                 190                 195

GTA GTC AAG GTG ATC GTC TCC GTC CAG CGG AAA AGA CAG GAG GCA GAA       1011
Val Val Lys Val Ile Val Ser Val Gln Arg Lys Arg Gln Glu Ala Glu
        200                 205                 210

GGT GAG GCC ACA GTC ATT GAG GCC CTG CAG GCC CCT CCG GAC GTC ACC       1059
Gly Glu Ala Thr Val Ile Glu Ala Leu Gln Ala Pro Pro Asp Val Thr
    215                 220                 225

ACG GTG GCC GTG GAG GAG ACA ATA CCC TCA TTC ACG GGG AGG AGC CCA       1107
Thr Val Ala Val Glu Glu Thr Ile Pro Ser Phe Thr Gly Arg Ser Pro
230                 235                 240                 245

AAC CAC TGACCCACAG ACTCTGCACC CCGACGCCAG AGATACCTGG AGCGACGGCT        1163
Asn His

GAATGAAAGA GGCTGTCCAC CTGGCGGAAC CACCGGAGCC CGGAGGCTTG GGGGCTCCAC     1223

CCTGGACTGG CTTCCGTCTC CTCCAGTGGA GGGAGAGGTG GCGCCCCTGC TGGGGTAGAG     1283

CTGGGGACGC CACGTGCCAT TCCCATGGGC CAGTGAGGGC CTGGGGCCTC TGTTCTGCTG     1343

TGGCCTGAGC TCCCCAGAGT CCTGAGGAGG AGCGCCAGTT GCCCCTCGCT CACAGACCAC     1403

ACACCCAGCC CTCCTGGGCC AACCCAGAGG GCCTTCAGAC CCCAGCTGTG TGCGCGTCTG     1463

ACTCTTGTGG CCTCAGCAGG ACAGGCCCCG GGCACTGCCT CACAGCCAAG CTGGACTGG      1523

GTTGGCTGCA GTGTGGTGTT TAGTGGATAC CACATCGGAA GTGATTTTCT AAATTGGATT     1583

TGAATTCGGC TCCTGTTTTC TATTTGTCAT GAAACAGTGT ATTTGGGGAG ATGCTGTGGG     1643

AGGATGTAAA TATCTTGTTT CTCCTCAAAA AAAAAAAAA AAAAAAAAA AAAAAAAA         1703
A                                                                     1704

(2) INFORMATION FOR SEQ ID NO:2:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Pro Pro Gly Asp Trp Gly Pro Pro Trp Arg Ser Thr Pro
-36 -35                 -30                 -25

Lys Thr Asp Val Leu Arg Leu Val Leu Tyr Leu Thr Phe Leu Gly Ala
-20                 -15                 -10                 -5

Pro Cys Tyr Ala Pro Ala Leu Pro Ser Cys Lys Glu Asp Glu Tyr Pro
                1                   5                   10

Val Gly Ser Glu Cys Cys Pro Lys Cys Ser Pro Gly Tyr Arg Val Lys
        15                  20                  25
```

```
Glu Ala Cys Gly Glu Leu Thr Gly Thr Val Cys Glu Pro Cys Pro Pro
         30                  35                  40
Gly Thr Tyr Ile Ala His Leu Asn Gly Leu Ser Lys Cys Leu Gln Cys
 45                  50                  55                  60
Gln Met Cys Asp Pro Ala Met Gly Leu Arg Ala Ser Arg Asn Cys Ser
                 65                  70                  75
Arg Thr Glu Asn Ala Val Cys Gly Cys Ser Pro Gly His Phe Cys Ile
             80                  85                  90
Val Gln Asp Gly Asp His Cys Ala Ala Cys Arg Ala Tyr Ala Thr Ser
         95                 100                 105
Ser Pro Gly Gln Arg Val Gln Lys Gly Gly Thr Glu Ser Gln Asp Thr
    110                 115                 120
Leu Cys Gln Asn Cys Pro Pro Gly Thr Phe Ser Pro Asn Gly Thr Leu
125                 130                 135                 140
Glu Glu Cys Gln His Gln Thr Lys Cys Ser Trp Leu Val Thr Lys Ala
                145                 150                 155
Gly Ala Gly Thr Ser Ser Ser His Trp Val Trp Trp Phe Leu Ser Gly
            160                 165                 170
Ser Leu Val Ile Val Ile Val Cys Ser Thr Val Gly Leu Ile Ile Cys
        175                 180                 185
Val Lys Arg Arg Lys Pro Arg Gly Asp Val Val Lys Val Ile Val Ser
    190                 195                 200
Val Gln Arg Lys Arg Gln Glu Ala Glu Gly Glu Ala Thr Val Ile Glu
205                 210                 215                 220
Ala Leu Gln Ala Pro Pro Asp Val Thr Thr Val Ala Val Glu Glu Thr
                225                 230                 235
Ile Pro Ser Phe Thr Gly Arg Ser Pro Asn His
            240                 245

(2) INFORMATION FOR SEQ ID NO:3:

(i) SEQUENCE CHARACTERISTICS:
        (A) LENGTH: 281 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

Met Val Ser Leu Pro Arg Leu Cys Ala Leu Trp Gly Cys Leu Leu Thr
  1                 5                  10                  15
Ala Val His Leu Gly Gln Cys Val Thr Cys Ser Asp Lys Gln Tyr Leu
                20                  25                  30
His Asp Gly Gln Cys Cys Asp Leu Cys Gln Pro Gly Ser Arg Leu Thr
            35                  40                  45
Ser His Cys Thr Ala Leu Glu Lys Thr Gln Cys His Pro Cys Asp Ser
        50                  55                  60
Gly Glu Phe Ser Ala Gln Trp Asn Arg Glu Ile Arg Cys His Gln His
 65                  70                  75                  80
Arg His Cys Glu Pro Asn Gln Gly Leu Arg Val Lys Lys Glu Gly Thr
                 85                  90                  95
Ala Glu Ser Asp Thr Val Cys Thr Cys Lys Glu Gly Gln His Cys Thr
            100                 105                 110
Ser Lys Asp Cys Glu Ala Cys Ala Gln His Thr Pro Cys Ile Pro Gly
        115                 120                 125
```

```
Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
    210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp
        275                 280

(2) INFORMATION FOR SEQ ID NO:4:

(i) SEQUENCE CHARACTERISTICS:
        (A) LENGTH: 2692 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 373..927

(ix) FEATURE:
        (A) NAME/KEY: sig_peptide
        (B) LOCATION: 373..480

(ix) FEATURE:
        (A) NAME/KEY: mat_peptide
        (B) LOCATION: 481..927

(xi) SEQUENCE DESCRIPTION: SEQ ID NO:4:

CCCCCTTCTA CAGGAAACCC GGAGTGGACT GGAACGGTGC AGGGGGAGAA CTCGCCCCTC      60

CCATCGGGCG CCTCCTTCAT ACCGGCCCTT CCCCTCGGCT TTGCCTGGAC AGCTCCTGCC     120

TCAGGCAGCG CCACCTGTGT CGCCCAGCGC CGCTCCACCC AGCAGGCCTG AGCCCCTCTC     180

TGCTGCCAGA CACCCCCTGC TGCCCACTAC TCCTGCTGCT CGGGTTCTGA GGCACAGCTT     240

GTCACACCGA GGCGGATTCT CTTTCTCTTT CTCTTTCTCT TCTGGCCCAC AGCCGCAGCA     300

ATGGCGCTGA GTTCCTCTGC TGGAGTTCAT CCTGCTAGCT GGGTTCCCGA GCTGCCGGTC     360

TGAGCCTGAG TC ATG GAG CCT CCT GGA GAC TGG GGG CCT CCT CCC TGG         408
              Met Glu Pro Pro Gly Asp Trp Gly Pro Pro Pro Trp
              -36 -35                 -30                 -25

AGA TCC ACC CCC AGA ACC GAC GTC TTG AGG CTG GTG CTG TAT CTC ACC       456
Arg Ser Thr Pro Arg Thr Asp Val Leu Arg Leu Val Leu Tyr Leu Thr
            -20                 -15                 -10

TTC CTG GGA GCC CCC TGC TAC GCC CCA GCT CTG CCG TCC TGC AAG GAG       504
Phe Leu Gly Ala Pro Cys Tyr Ala Pro Ala Leu Pro Ser Cys Lys Glu
        -5                   1                   5
```

-continued

```
GAC GAG TAC CCA GTG GGC TCC GAG TGC TGC CCC AAG TGC AGT CCA GGT    552
Asp Glu Tyr Pro Val Gly Ser Glu Cys Cys Pro Lys Cys Ser Pro Gly
     10              15                  20

TAT CGT GTG AAG GAG GCC TGC GGG GAG CTG ACG GGC ACA GTG TGT GAA    600
Tyr Arg Val Lys Glu Ala Cys Gly Glu Leu Thr Gly Thr Val Cys Glu
 25              30                  35                  40

CCC TGC CCT CCA GGC ACC TAC ATT GCC CAC CTC AAT GGC CTA AGC AAG    648
Pro Cys Pro Pro Gly Thr Tyr Ile Ala His Leu Asn Gly Leu Ser Lys
             45                  50                  55

TGT CTG CAG TGC CAA ATG TGT GAC CCA GAT ATT GGT TCC CCC TGT GAC    696
Cys Leu Gln Cys Gln Met Cys Asp Pro Asp Ile Gly Ser Pro Cys Asp
                 60                  65                  70

CTC AGG GGA AGA GGT CAC CTG GAG GCT GGT GCC CAC CTG AGT CCA GGC    744
Leu Arg Gly Arg Gly His Leu Glu Ala Gly Ala His Leu Ser Pro Gly
             75                  80                  85

AGA CAG AAA GGG GAA CCA GAC CCA GAG GTG GCC TTT GAG TCA CTG AGC    792
Arg Gln Lys Gly Glu Pro Asp Pro Glu Val Ala Phe Glu Ser Leu Ser
         90                  95                 100

GCA GAG CCT GTC CAT GCG GCC AAC GGC TCT GTC CCC TTG GAG CCT CAT    840
Ala Glu Pro Val His Ala Ala Asn Gly Ser Val Pro Leu Glu Pro His
105                 110                 115                 120

GCC AGG CTC AGC ATG GCC AGT GCT CCC TGC GGC CAG GCA GGA CTG CAC    888
Ala Arg Leu Ser Met Ala Ser Ala Pro Cys Gly Gln Ala Gly Leu His
                125                 130                 135

CTG CGG GAC AGG GCT GAC GGC ACA CCT GGG GGC AGG GCC TGAGCCTACA     937
Leu Arg Asp Arg Ala Asp Gly Thr Pro Gly Gly Arg Ala
            140                 145

GGGAGGCACA GGGCAGGTGG GCTAGCCATG AACAGAAGAG GAAGCTGGAG TGCTTTGGGG    997
GTTCATGCAT GTAGGCTGGG ATTTGGGGCT CACACCTCAA CCTGCATGCC CAGTTCCATG   1057
CCCCTCCCCT CTTGTGAAAG CACCTGTCTA CTTGGGCTGA GGATGTGGGG GCACAGGTGG   1117
CAGGTGAGGC TGCCCTCAGG AGGGGCCCAG GCCCAGCTTG TACCCCACCT CCACCAGTAC   1177
CTGAAGAAGT GGGGCTCTCA CCCTACCTGC CTCTGCCATT GGAATGGCCT GGTTTGCACA   1237
GATGGGAAAC CCGTTTGAGG GGTGGGTGTC TGGGTGGGCA CGTGGGGCGA GGACCTGCCT   1297
GAGGGACCCT GCCCTGGAAC TGACAGTGCA AGCTCGGCGT CCTGCCCATC TGGGCAGAAG   1357
GCTGGTTTCT CCCATCAACG AAGCCCTCCC AGGACCTTCC TGCAAGCCCT CGTCCCACAC   1417
GCAGCTCTGC CGTCCCTTGG TGTCCCTCCC GGCCTCAGGT CCTCCATGCT GGGTACCTCT   1477
GGGCACCTCG TTTGGCTGAG CCAGGGGTTC AGCCTGGCAG GGCGCCCTGG CAGCAGTCCT   1537
TGGCCTGTGG ATGCTGTCCT GGCCTGTGGA TGGTGTCCCG CCCTCCACGT ACCCCTCTCA   1597
CCCCCTCCTC TTGGACTCCA GCCATGGGCC TGCGCGCGAG CCGGAACTGC TCCAGGACAG   1657
AGAACGCCGT GTGTGGCTGC AGCCCAGGCC ACTTCTGCAT CGTCCAGGAC GGGGACCACT   1717
GCGCCGCGTG CCGCGCTTAC GCCACCTCCA GCCCGGGCCA GAGGGTGCAG AAGGGAGGCA   1777
CCGAGAGTCA GGACACCCTG TGTCAGAACT GCCCCCCGGG GACCTTCTCT CCCAATGGGA   1837
CCCTGGAGGA ATGTCAGCAC CAGACCAATT GGCCTAATCA TATGTGTGAA AAGAAGAAAG   1897
CCAAGGGGTG AGCACACGGT GGCCCCATCA GGGTTCATGT CCCCAGCCGT CACCTCTTGG   1957
AGCTCTGTCA CCCCAAGCCT GGGAGGTGGC CCCAGAGCTT TTCCAGGATC CGCGGCTCCT   2017
CCCAGGGCAG CCACTGCAGG CTGGGCAGG TGTATGTAGT CAAGGTGATC GTCTCCGTCC   2077
AGCGGTAAAA GACAGGAGGC AGAAGGTGAG GCCACAGTCA TTGAGCCCTG CAGGCCCCTC   2137
CGGACGTCAC CACGGTGGCC GTGGAGGAGA CAATACCCTC ATTCACGGGG AGGAGCCCAA   2197
```

```
ACCACTGACC CACAGACTCT GCACCCCGAC GCCAGAGATA CCTGGAGAGA CGGCTGCTGA    2257

TAGAGGCTGT CCACCTGGCG AAACCACCGG AGCCCGGAGG CTTGGGGGCT CCGCCCTGGG    2317

CTGGTTTCCG TCTCCTCCAG TGGAGGGAGA GGTGGTGCCC CTGCTGGTGG TAGAGCTGGG    2377

GACGCCACGT GCCATTCCCA TGGTTCAGTG AGGGGCTGGT GGCCTCTGTT CTGCTGTGGC    2437

CTGAGCTCCC CAGAGTCCTG AGGAGGAGCC CCAGTTGCCC CTCGCTCACA GACCACACAC    2497

CCAGCCCTCC TGGGCCAACC CAGAGGCCCC TTCAGACCCC AGCTGTCTGC GCGTCTGACT    2557

CTTGTGGCCT CAGCAGGACA GGCCCCGGGC ACTGCCTCAC AGCCAAGGCT GGAATGGGTT    2617

GGCTGCAGTG TGGTGTTTAG TGGATACCAC ATCGGAAGTG ATTTTCTAAA AATTGGATTT    2677

GAATTCGGAA AAAAA                                                    2692
```

(2) INFORMATION FOR SEQ ID NO:5:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Pro Pro Gly Asp Trp Gly Pro Pro Trp Arg Ser Thr Pro
-36 -35             -30                 -25

Arg Thr Asp Val Leu Arg Leu Val Leu Tyr Leu Thr Phe Leu Gly Ala
-20             -15              -10                  -5

Pro Cys Tyr Ala Pro Ala Leu Pro Ser Cys Lys Glu Asp Glu Tyr Pro
                 1               5                  10

Val Gly Ser Glu Cys Cys Pro Lys Cys Ser Pro Gly Tyr Arg Val Lys
             15                  20                  25

Glu Ala Cys Gly Glu Leu Thr Gly Thr Val Cys Glu Pro Cys Pro Pro
             30                  35                  40

Gly Thr Tyr Ile Ala His Leu Asn Gly Leu Ser Lys Cys Leu Gln Cys
             45              50                  55              60

Gln Met Cys Asp Pro Asp Ile Gly Ser Pro Cys Asp Leu Arg Gly Arg
                 65                  70                  75

Gly His Leu Glu Ala Gly Ala His Leu Ser Pro Gly Arg Gln Lys Gly
             80                  85                  90

Glu Pro Asp Pro Glu Val Ala Phe Glu Ser Leu Ser Ala Glu Pro Val
             95                 100                 105

His Ala Ala Asn Gly Ser Val Pro Leu Glu Pro His Ala Arg Leu Ser
            110                 115                 120

Met Ala Ser Ala Pro Cys Gly Gln Ala Gly Leu His Leu Arg Asp Arg
125                 130                 135                 140

Ala Asp Gly Thr Pro Gly Gly Arg Ala
                145
```

(2) INFORMATION FOR SEQ ID NO:6:

(i) SEQUENCE CHARACTERISTICS:
        (A) LENGTH: 248 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:6:

```
Met Ala Pro Val Ala Val Trp Ala Ala Leu Ala Val Gly Leu Glu Leu
1               5                  10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser
                245

(2) INFORMATION FOR SEQ ID NO:7:

(i) SEQUENCE CHARACTERISTICS:
        (A) LENGTH: 2637 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 247..654

(xi) SEQUENCE DESCRIPTION: SEQ ID NO:7:

AAAGCTCGGG CTCCACCGGG GACGACCGCT CCTAGAAACT GAGTGGTATC CCCCGGGCCT      60

GCAGGAATTC CAACCTGCCT GAAGGGACCC TGCCCTGGAA CTGACAGTGC AAGCTCGGCG     120

TCCTGCCCAT CTGGGAAGAA GGCTGGTTTC TCCCATCAAC GAAGCCCTCC CAGGACCTTC     180

CTGCAAGCCC TCGTCCCACA CGCAGCTCTG CCGTCCCTTG GTGTCCCTCC CGGCCTCAGG     240

TCCTCC ATG CTG GGT ACC TCT GGG CAC CTC GTT TGG CTG AGC CAG GGG        288
       Met Leu Gly Thr Ser Gly His Leu Val Trp Leu Ser Gln Gly
           150             155                 160

TTC AGC CTG GCA GGG CGC CCT GGC AGC AGT CCT TGG CCT GTG GAT GCT       336
Phe Ser Leu Ala Gly Arg Pro Gly Ser Ser Pro Trp Pro Val Asp Ala
```

-continued

```
            165                 170                 175
GTC CTG GCC TGT GGA TGG TGT CCC GGC CTC CAC GTA CCC CCT CTC AGC      384
Val Leu Ala Cys Gly Trp Cys Pro Gly Leu His Val Pro Pro Leu Ser
180                 185                 190                 195

CCC TCC TCT TGG ACT CCA GCC ATG GGC CTG CGC GCG AGC CGG AAC TGC      432
Pro Ser Ser Trp Thr Pro Ala Met Gly Leu Arg Ala Ser Arg Asn Cys
                200                 205                 210

TCC AGG ACA GAG AAC GCC GTG TGT GGC TGC AGC CCA GGC CAC TTC TGC      480
Ser Arg Thr Glu Asn Ala Val Cys Gly Cys Ser Pro Gly His Phe Cys
            215                 220                 225

ATC GTC CAG GAC GGG GAC CAC TGC GCC GCG TGC CGC GCT TAC GCC ACC      528
Ile Val Gln Asp Gly Asp His Cys Ala Ala Cys Arg Ala Tyr Ala Thr
            230                 235                 240

TCC AGC CCG GGC CAG AGG GTG CAG AAG GGA GGC ACC GAG AGT CAG GAC      576
Ser Ser Pro Gly Gln Arg Val Gln Lys Gly Gly Thr Glu Ser Gln Asp
245                 250                 255

ACC CTG TGT CAG AAC TGC CCC CGG GGA CCT TCT CTC CCA ATG GGA CCC      624
Thr Leu Cys Gln Asn Cys Pro Arg Gly Pro Ser Leu Pro Met Gly Pro
260                 265                 270                 275

TGG AGG AAT GTC AGC ACC AGA CCA AGT AAG TGAACCCGGG GGAGGCCAGC        674
Trp Arg Asn Val Ser Thr Arg Pro Ser Lys
                280                 285

TCTGTGCCCT GGGGAGGGGG CTCCACGTTG CTTCCCTGGG AGATGACCGT CTTCTCCAGC    734
AGAAAGGTTG AAGGTCCCAC CCTGAGCGGC ACCCTGGTCA CATGCCTGCG TCCAGGAGAG    794
CTGCAGGGTG AAGCCTGTGT GCCCCAGATA ACCCCTTCCA TGGGCCCAGA CAAAGCCTCA    854
TCAGATCTGA GCTTCCTGGA GGCTCAGGAT GGGCCTTCCC AGAAGCAGGC CCAGAGGGAG    914
GCTGCCTCCA GATCCCTGT CCCCTGGGGC TGTGGGTGTC CCTGAATGTC AGGGCCATGG     974
GAGGGCCCCT GGGCTTCAGG GGTTGGGGAA AGTGAACACT CTGCTCTTTG TCCACCTTCG   1034
GGAGGACAAC CTTCAAATGC TGACCCTGGG CCCCTAACTG ACCTGAGACT TCAGAGCTTC   1094
TTGGGAGGAG CTGGGGTCCC CCAGCGGAGC CTGGGATGGA GCAGGGATGG CTGCCCCAGG   1154
GAGGGGGCGG TGGGGCCTTC CATCCTGCTC TGCCCTCCTC GTCCTCTGGC CCAGCTCAG    1214
TCCTGTCCAT CTCCAGCTCT AACCATTTGT GGCCCGACAC TGGCTCTCCC TCTACCTTCT   1274
GTCCTTGTCT GACACTGGTC TCCCGTGCTC TGGGGTCTCT GCACTGATGG CTGCCTCCG    1334
CTTCTCTCCC CTCTCCCTCT GCCGTCCTGT CTCCTGTGGC CAGTCTCTCC TTGTTTCTCT   1394
TCTCCTCCTT CCTTCTCTCC ACCTCCCCAT AGCCGAGCTT GGAAAAGTCA GACAGACCTC   1454
TGAGGTCTCA TCCTGGAGCT GCCACCAGCC CAGCCTCCCT GGGACCTGTC TTCACTGCCT   1514
GGGGCCCTGG GAGCCAGGGA GGCTCCCTGA GGCTGAGTGA ACACTGGGCG CTGCACCTGC   1574
CTCTCCCACG TCCTCGGCCC CACTCCCGCA GGTGCAGCTG GCTGGTGACG AAGCCCGGAG   1634
CTGGGACCAG CAGCTCCCAC TGGGTATGGT GGTTTCTCTC AGGGAGCCTC GTCATCGTCA   1694
TTGTTTGCTC CACAGTTGGC CTAATCATAT GTGTGAAAAG AAGAAAGCCA AGGGGTGATG   1754
TAGTCAAGGT GATCGTCTCC GTCCAGGTAT TGATCCTCCT CCCCCTCTCC CTCCCCCCTC   1814
CACCTTCCCA CCTCCCCTCT CCCCGCTGGG GCTGGTGTTT CTGGTGTACA TGGTGGGGGC   1874
TCCCAGTTCT CTGAGGGTCC TGAGTCTTTC AAGTACAGCC ACGGTAGCTC AGGAAAGAAC   1934
CCACCCCCTC AAACTGAAAG CAGTAAAATG AACCCGAGAA CCTGGAGTCC CAGGGGGGCC   1994
TGAGCAGGCA GGGTCTCCAC GATTCGTGTG CTCACAGCGG GAAAAGACAG GAGGCAGAAG   2054
GTGAGGCCAC AGTCATTGAG GCCCTGCAGG CCCCTCCGGA CGTCACCACG GTGGCCGTGG   2114
AGGAGACAAT ACCCTCATTC ACGGGGGAGG AGCCCAAACC ACTGACCCAC AGACTCTGCA   2174
```

```
CCCCGACGCC AGAGATACCT GGAGCGACGG CTGCTGAAAG AGGCTGTCCA CCTGGCGAAA    2234

CCACCGGAGC CCGGAGGTTT GGGGGCTCCG CCCTGGGCTG GTTTCCGTCT CCTCCAGTGG    2294

AGGGAGAGGT GGGGCCCCTG CTGGGGTAGA GCTGGGACG CCACGTGCCA TTCCCATGGG    2354

CCAGTGAGGG CCTGGGGCCT CTGTTCTGCT GTGGCCTGAG CTCCCCAGAG TCCTGAGGAG    2414

GAGCGCCAGT TGCCCCTCGC TCACAGACCA CACACCCAGC CCTCCTGGGT CCAGCCCAGA    2474

GGGCCCTTCA GACCCCAGCT GTCTGCGCGT CTGACTCTTG TGGCCTCAGC AGGACAGGCC    2534

CCGGGCACTG CCTTCAAGCC AAGGCTGGAC TGGGTTGGCT GCAGTGTGGT GTTTAGTGGA    2594

TACCACATCG GAAGTGATTT TCTAAATTGG ATTTGAAAAA AAA                      2637
```

(2) INFORMATION FOR SEQ ID NO:8:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:8:

```
Met Leu Gly Thr Ser Gly His Leu Val Trp Leu Ser Gln Gly Phe Ser
  1               5                  10                  15

Leu Ala Gly Arg Pro Gly Ser Ser Pro Trp Pro Val Asp Ala Val Leu
             20                  25                  30

Ala Cys Gly Trp Cys Pro Gly Leu His Val Pro Leu Ser Pro Ser
         35                  40                  45

Ser Trp Thr Pro Ala Met Gly Leu Arg Ala Ser Arg Asn Cys Ser Arg
     50                  55                  60

Thr Glu Asn Ala Val Cys Gly Cys Ser Pro Gly His Phe Cys Ile Val
 65                  70                  75                  80

Gln Asp Gly Asp His Cys Ala Ala Cys Arg Ala Tyr Ala Thr Ser Ser
                 85                  90                  95

Pro Gly Gln Arg Val Gln Lys Gly Gly Thr Glu Ser Gln Asp Thr Leu
            100                 105                 110

Cys Gln Asn Cys Pro Arg Gly Pro Ser Leu Pro Met Gly Pro Trp Arg
        115                 120                 125

Asn Val Ser Thr Arg Pro Ser Lys
        130                 135
```

(2) INFORMATION FOR SEQ ID NO:9:

(i) SEQUENCE CHARACTERISTICS:
        (A) LENGTH: 198 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

```
Met Ala Pro Val Ala Val Trp Ala Ala Leu Ala Val Gly Leu Glu Leu
  1               5                  10                  15

Trp Ala Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
         35                  40                  45

Thr Ala Gln Met Cys Cys Ser Lys Cys Ser Pro Gly Gln His Ala Lys
```

-continued

```
                50                  55                  60
Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                     85                  90                  95

Gly Ser Arg Cys Ser Ser Asp Gln Val Glu Thr Gln Ala Cys Thr Arg
                    100                 105                 110

Glu Gln Asn Arg Ile Cys Thr Cys Arg Pro Gly Trp Tyr Cys Ala Leu
                115                 120                 125

Ser Lys Gln Glu Gly Cys Arg Leu Cys Ala Pro Leu Arg Lys Cys Arg
            130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                    165                 170                 175

Asp Ile Cys Arg Pro His Gln Ile Cys Asn Val Val Ala Ile Pro Gly
                180                 185                 190

Asn Ala Ser Met Asp Ala
            195
```

(2) INFORMATION FOR SEQ ID NO:10:

(i) SEQUENCE CHARACTERISTICS:
    (A) LENGTH: 154 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:10:

```
Val Cys Pro Gln Gly Lys Tyr Ile His Pro Gln Asn Asn Ser Ile Cys
 1                   5                  10                  15

Cys Thr Lys Cys His Lys Gly Thr Tyr Leu Tyr Asn Asp Cys Pro Gly
                     20                  25                  30

Pro Gly Gln Asp Thr Asp Cys Arg Glu Cys Glu Ser Gly Ser Phe Thr
                 35                  40                  45

Ala Ser Glu Asn His Leu Arg His Cys Leu Ser Cys Ser Lys Cys Arg
             50                  55                  60

Lys Glu Met Gly Gln Val Glu Ile Ser Ser Cys Thr Val Asp Arg Asp
 65                  70                  75                  80

Thr Val Cys Gly Cys Arg Lys Asn Gln Tyr Arg His Tyr Trp Ser Glu
                     85                  90                  95

Asn Leu Phe Gln Cys Phe Asn Cys Ser Leu Cys Leu Asn Gly Thr Val
                    100                 105                 110

His Leu Ser Cys Gln Glu Lys Gln Asn Thr Val Cys Thr Cys His Ala
                115                 120                 125

Gly Phe Phe Leu Arg Glu Asn Glu Cys Val Ser Cys Ser Asn Cys Lys
            130                 135                 140

Lys Ser Leu Glu Cys Thr Lys Leu Cys Leu
145                 150
```

(2) INFORMATION FOR SEQ ID NO:11:

(i) SEQUENCE CHARACTERISTICS:
    (A) LENGTH: 163 amino acids
    (B) TYPE: amino acid
    (C) STRANDEDNESS: Not Relevant (D) TOPOLOGY: Not Relevant (ii) MOLECULE TYPE: protein (xi) SEQUENCE DESCRIPTION: SEQ ID NO:11:

```
Thr Cys Arg Leu Arg Glu Tyr Tyr Asp Gln Thr Ala Gln Met Cys Cys
1               5                   10                  15

Ser Lys Cys Ser Pro Gly Gln His Ala Lys Val Phe Cys Thr Lys Thr
            20                  25                  30

Ser Asp Thr Val Cys Asp Ser Cys Glu Asp Ser Thr Tyr Thr Gln Leu
        35                  40                  45

Trp Asn Trp Val Pro Glu Cys Leu Ser Cys Gly Ser Arg Cys Ser Ser
    50                  55                  60

Asp Gln Val Glu Thr Gln Ala Cys Thr Arg Glu Gln Asn Arg Ile Cys
65                  70                  75                  80

Thr Cys Arg Pro Gly Trp Tyr Cys Ala Leu Ser Lys Gln Glu Gly Cys
                85                  90                  95

Arg Leu Cys Ala Pro Leu Arg Lys Cys Arg Pro Gly Phe Gly Val Ala
            100                 105                 110

Arg Pro Gly Thr Glu Thr Ser Asp Val Val Cys Lys Pro Cys Ala Pro
        115                 120                 125

Gly Thr Phe Ser Asn Thr Thr Ser Ser Thr Asp Ile Cys Arg Pro His
130                 135                 140

Gln Ile Cys Asn Val Val Ala Ile Pro Gly Asn Ala Ser Met Asp Ala
145                 150                 155                 160

Val Cys Thr
```

(2) INFORMATION FOR SEQ ID NO:12:

(i) SEQUENCE CHARACTERISTICS:
    (A) LENGTH: 163 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:12:

```
Ala Cys Arg Glu Lys Gln Tyr Leu Ile Asn Ser Gln Cys Cys Ser Leu
1               5                   10                  15

Cys Gln Pro Gly Gln Lys Leu Val Ser Asp Cys Thr Glu Pro Thr Glu
            20                  25                  30

Thr Glu Cys Leu Pro Cys Gly Glu Ser Glu Phe Leu Asp Thr Trp Asn
        35                  40                  45

Arg Glu Thr His Cys His Gln His Lys Tyr Cys Asp Pro Asn Leu Gly
    50                  55                  60

Leu Arg Val Gln Gln Lys Gly Thr Ser Glu Thr Asp Thr Ile Cys Thr
65                  70                  75                  80

Cys Glu Glu Gly Trp His Cys Thr Ser Glu Ala Cys Glu Ser Cys Val
                85                  90                  95

Leu His Arg Ser Cys Ser Pro Gly Phe Gly Val Lys Gln Ile Ala Thr
            100                 105                 110

Gly Val Ser Asp Thr Ile Cys Glu Pro Cys Pro Val Gly Phe Phe Ser
        115                 120                 125

Asn Val Ser Ser Ala Phe Glu Lys Cys His Pro Trp Thr Ser Cys Glu
130                 135                 140

Thr Lys Asp Leu Val Val Gln Gln Ala Gly Thr Asn Lys Thr Asp Val
```

```
145                 150                 155                 160
Val Cys Gly (2) INFORMATION FOR SEQ ID NO:13:

(i) SEQUENCE CHARACTERISTICS:
        (A) LENGTH: 132 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Cys Ser Asn Cys Pro Ala Gly Thr Phe Cys Asp Asn Asn Arg Asn Gln
1               5                   10                  15

Ile Cys Ser Pro Cys Pro Pro Asn Ser Phe Ser Ser Ala Gly Gly Gln
            20                  25                  30

Arg Thr Cys Asp Ile Cys Arg Gln Cys Lys Gly Val Phe Arg Thr Arg
        35                  40                  45

Lys Glu Cys Ser Ser Thr Ser Asn Ala Glu Cys Asp Cys Thr Pro Gly
    50                  55                  60

Phe His Cys Leu Gly Ala Gly Cys Ser Met Cys Glu Gln Asp Cys Lys
65                  70                  75                  80

Gln Gly Gln Glu Leu Thr Lys Lys Gly Cys Lys Asp Cys Cys Phe Gly
                85                  90                  95

Thr Phe Asn Lys Gln Lys Arg Gly Ile Cys Arg Pro Trp Thr Asn Cys
            100                 105                 110

Ser Leu Asp Gly Lys Ser Val Leu Val Asn Gly Thr Lys Glu Arg Asp
        115                 120                 125

Val Val Cys Gly
        130

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGCCCATGGC CCCAGCTCTG CCGTCCT                                          27

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGCAAGCTTA TTGTGGGAGC TGCTGGTCCC                                       30

(2) INFORMATION FOR SEQ ID NO:16:

(i) SEQUENCE CHARACTERISTICS:
        (A) LENGTH: 25 base pairs
```

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CGCGGATCCC GGAGCCCCCT GCTAC                                     25

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CGCGGTACCA TTGTGGGAGC TGCTGGTCCC                                30

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GCGCGGATCC ACCATGGAGC CTCCTGGAGA CTGG                           34

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GCGCGGTACC TCTACCCCAG CAGGGGCGCC A                              31

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GCGCGGATCC ACCATGGAGC CTCCTGGAGA CTGG                           34

(2) INFORMATION FOR SEQ ID NO:21:

(i) SEQUENCE CHARACTERISTICS:
        (A) LENGTH: 58 base pairs
        (B) TYPE: nucleic acid
        (C) STRANDEDNESS: single
        (D) TOPOLOGY: linear
```

```
          (ii) MOLECULE TYPE: cDNA (xi) SEQUENCE DESCRIPTION: SEQ ID NO:21:

GCGCTCTAGA TCAAGCGTAG TCTGGGACGT CGTATGGGTA GTGGTTTGGG CTCCTCCC              58

(2) INFORMATION FOR SEQ ID NO:22:

(i) SEQUENCE CHARACTERISTICS:
              (A) LENGTH: 34 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:22:

GCGCGGATCC ACCATGGAGC CTCCTGGAGA CTGG                                       34

(2) INFORMATION FOR SEQ ID NO:23:

(i) SEQUENCE CHARACTERISTICS:
              (A) LENGTH: 35 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:23:

CAGGAATTCG CAGCCATGGA GCCTCCTGGA GACTG                                      35

(2) INFORMATION FOR SEQ ID NO:24:

(i) SEQUENCE CHARACTERISTICS:
              (A) LENGTH: 53 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:24:

CCATACCCAG GTACCCCTTC CCTCGATAGA TCTTGCCTTC GTCACCAGCC AGC                  53

(2) INFORMATION FOR SEQ ID NO:25:

(i) SEQUENCE CHARACTERISTICS:
              (A) LENGTH: 881 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS
              (B) LOCATION: 9..857

(ix) FEATURE:
              (A) NAME/KEY: sig_peptide
              (B) LOCATION: 9..122

(ix) FEATURE:
              (A) NAME/KEY: mat_peptide
              (B) LOCATION: 123..857

(xi) SEQUENCE DESCRIPTION: SEQ ID NO:25:

CCTGAGGC ATG GAG CCT CCT GGA GAC TGG GGG CCT CCT CCC TGG AGA TCC            50
         Met Glu Pro Pro Gly Asp Trp Gly Pro Pro Pro Trp Arg Ser
         -38         -35                 -30                 -25
```

```
ACC CCC AGA ACC GAC GTC TTG AGG CTG GTG CTG TAT CTC ACC TTC CTG        98
Thr Pro Arg Thr Asp Val Leu Arg Leu Val Leu Tyr Leu Thr Phe Leu
            -20                 -15                 -10

GGA GCC CCC TGC TAC GCC CCA GCT CTG CCG TCC TGC AAG GAG GAC GAG        146
Gly Ala Pro Cys Tyr Ala Pro Ala Leu Pro Ser Cys Lys Glu Asp Glu
        -5                   1                   5

TAC CCA GTG GGC TCC GAG TGC TGC CCC AAG TGC AGT CCA GGT TAT CGT        194
Tyr Pro Val Gly Ser Glu Cys Cys Pro Lys Cys Ser Pro Gly Tyr Arg
        10                  15                  20

GTG AAG GAG GCC TGC GGG GAG CTG ACG GGC ACA GTG TGT GAA CCC TGC        242
Val Lys Glu Ala Cys Gly Glu Leu Thr Gly Thr Val Cys Glu Pro Cys
    25                  30                  35                  40

CCT CCA GGC ACC TAC ATT GCC CAC CTC AAT GGC CTA AGC AAG TGT CTG        290
Pro Pro Gly Thr Tyr Ile Ala His Leu Asn Gly Leu Ser Lys Cys Leu
                    45                  50                  55

CAG TGC CAA ATG TGT GAC CCA GCC ATG GGC CTG CGC GCG AGC CGG AAC        338
Gln Cys Gln Met Cys Asp Pro Ala Met Gly Leu Arg Ala Ser Arg Asn
                60                  65                  70

TGC TCC AGG ACA GAG AAC GCC GTG TGT GGT TGC AGC CCA GGC CAC TTC        386
Cys Ser Arg Thr Glu Asn Ala Val Cys Gly Cys Ser Pro Gly His Phe
            75                  80                  85

TGC ATC GTC CAG GAC GGG GAC CAC TGC GCC GCG TGC CGC GCT TAC GCC        434
Cys Ile Val Gln Asp Gly Asp His Cys Ala Ala Cys Arg Ala Tyr Ala
        90                  95                  100

ACC TCC AGC CCG GGC CAG AGG GTG CAG AAG GGA GGC ACC GAG AGT CAG        482
Thr Ser Ser Pro Gly Gln Arg Val Gln Lys Gly Gly Thr Glu Ser Gln
105                 110                 115                 120

GAC ACC CTG TGT CAG AAC TGC CCC CCG GGG ACC TTC TCT CCC AAT GGG        530
Asp Thr Leu Cys Gln Asn Cys Pro Pro Gly Thr Phe Ser Pro Asn Gly
                125                 130                 135

ACC CTG GAG GAA TGT CAG CAC CAG ACC AAG TGC AGC TGG CTG GTG ACG        578
Thr Leu Glu Glu Cys Gln His Gln Thr Lys Cys Ser Trp Leu Val Thr
                140                 145                 150

AAG GCC GGA GCT GGG ACC AGC AGC TCC CAC TGG GTA TGG TGG TTT CTC        626
Lys Ala Gly Ala Gly Thr Ser Ser Ser His Trp Val Trp Trp Phe Leu
            155                 160                 165

TCA GGG AGC CTC GTC ATC GTC ATT GTT TGC TCC ACA GTT GGC CTA ATC        674
Ser Gly Ser Leu Val Ile Val Ile Val Cys Ser Thr Val Gly Leu Ile
        170                 175                 180

ATA TGT GTG AAA AGA AGA AAG CCA AGG GGT GAT GTA GTC AAG GTG ATC        722
Ile Cys Val Lys Arg Arg Lys Pro Arg Gly Asp Val Val Lys Val Ile
185                 190                 195                 200

GTC TCC GTC CAG CGG AAA AGA CAG GAG GCA GAA GGT GAG GCC ACA GTC        770
Val Ser Val Gln Arg Lys Arg Gln Glu Ala Glu Gly Glu Ala Thr Val
                205                 210                 215

ATT GAG GCC CTG CAG GCC CCT CCG GAC GTC ACC ACG GTG GCC GTG GAG        818
Ile Glu Ala Leu Gln Ala Pro Pro Asp Val Thr Thr Val Ala Val Glu
                220                 225                 230

GAG ACA ATA CCC TCA TTC ACG GGG AGG AGC CCA AAC CAC TGACCCACAG         867
Glu Thr Ile Pro Ser Phe Thr Gly Arg Ser Pro Asn His
                235                 240                 245

ACTCTGCACC CCGA                                                        881
```

(2) INFORMATION FOR SEQ ID NO:26:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:26:

```
Met Glu Pro Pro Gly Asp Trp Gly Pro Pro Trp Arg Ser Thr Pro
-38         -35             -30             -25

Lys Thr Asp Val Leu Arg Leu Val Leu Tyr Leu Thr Phe Leu Gly Ala
        -20             -15             -10

Pro Cys Tyr Ala Pro Ala Leu Pro Ser Cys Lys Glu Asp Glu Tyr Pro
    -5                   1               5                   10

Val Gly Ser Glu Cys Cys Pro Lys Cys Ser Pro Gly Tyr Arg Val Lys
                15              20              25

Glu Ala Cys Gly Glu Leu Thr Gly Thr Val Cys Glu Pro Cys Pro Pro
            30              35              40

Gly Thr Tyr Ile Ala His Leu Asn Gly Leu Ser Lys Cys Leu Gln Cys
            45              50              55

Gln Met Cys Asp Pro Ala Met Gly Leu Arg Ala Ser Arg Asn Cys Ser
        60              65              70

Arg Thr Glu Asn Ala Val Cys Gly Cys Ser Pro Gly His Phe Cys Ile
75              80              85              90

Val Gln Asp Gly Asp His Cys Ala Ala Cys Arg Ala Tyr Ala Thr Ser
                95              100             105

Ser Pro Gly Gln Arg Val Gln Lys Gly Gly Thr Glu Ser Gln Asp Thr
            110             115             120

Leu Cys Gln Asn Cys Pro Pro Gly Thr Phe Ser Pro Asn Gly Thr Leu
        125             130             135

Glu Glu Cys Gln His Gln Thr Lys Cys Ser Trp Leu Val Thr Lys Ala
    140             145             150

Gly Ala Gly Thr Ser Ser Ser His Trp Val Trp Trp Phe Leu Ser Gly
155             160             165             170

Ser Leu Val Ile Val Ile Val Cys Ser Thr Val Gly Leu Ile Ile Cys
                175             180             185

Val Lys Arg Arg Lys Pro Arg Gly Asp Val Val Lys Val Ile Val Ser
            190             195             200

Val Gln Arg Lys Arg Gln Glu Ala Glu Gly Glu Ala Thr Val Ile Glu
        205             210             215

Ala Leu Gln Ala Pro Pro Asp Val Thr Thr Val Ala Val Glu Glu Thr
    220             225             230

Ile Pro Ser Phe Thr Gly Arg Ser Pro Asn His
235             240             245
```

HUMAN TUMOR NECROSIS FACTOR RECEPTOR-LIKE 2

CROSS-REFERENCE TO RELATED APPLICATIONS

The present application is a divisional of U.S. application Ser. No. 08/741,095, filed Oct. 30, 1996, which is incorporated herein by reference; said U.S. application Ser. No. 08/741,095 is a continuation-in-part of U.S. application Ser. No. 08/464,595, U.S. application Ser. No. 08/462,962, and U.S. application Ser. No. 08/462,315, each of which was filed Jun. 5, 1995 and are incorporated herein by reference; said U.S. application Ser. Nos. 08/464,595, 08/462,962 and 08/462,315 are each continuations-in-part of PCT/US95/05058, filed Apr. 27, 1995, which is incorporated herein by reference.

BACKGROUND OF THE INVENTION

1. Field of the Invention

The present invention relates to novel members of the Tumor Necrosis Factor (TNF) receptor family. More specifically, isolated nucleic acid molecules are provided encoding a human TNF receptor-related protein, referred to herein as the TR2 receptor of FIGS. 1A-1B, having considerable homology to murine CD40. Two different TR2 splice variants, referred to as TR2-SV1 and TR2-SV2, are also provided. TR2 polypeptides are also provided with homology to human type 2 TNF receptor (TNF-RII). Further provided are vectors, host cells and recombinant methods for producing the same. The invention also relates to both the inhibition and enhancement of the activity of TR2 receptor polypeptides and diagnostic methods for detecting TR2 receptor gene expression.

2. Related Art

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., *Annu. Rev. Immunol.*, 7:625-655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are ten known members of the TNF-related cytokine family, TNF-α, TNF-β (lymphotoxin-α) LT-β, TRAIL and ligands for the Fas receptor, CD30, CD27, CD40, OX40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominantly by activated macrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136(7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

TNF-β has many activities, including induction of an antiviral state and tumor necrosis, activation of polymorphonuclear leukocytes, induction of class I major histocompatibility complex antigens on endothelial cells, induction of adhesion molecules on endothelium and growth hormone stimulation (Ruddle, N. and Homer, R., *Prog. Allergy* 40:162-182 (1988)).

Both TNF-α and TNF-β are involved in growth regulation and interact with hemopoietic cells at several stages of differentiation, inhibiting proliferation of various types of precursor cells, and inducing proliferation of immature myelomonocytic cells. Porter, A., *Tibtech* 9:158-162 (1991).

Recent studies with "knockout" mice have shown that mice deficient in TNF-β production show abnormal development of the peripheral lymphoid organs and morphological changes in spleen architecture (reviewed in Aggarwal et al., *Eur Cytokine Netw*, 7(2):93-124 (1996)). With respect to the lymphoid organs, the popliteal, inguinal, para-aortic, mesenteric, axillary and cervical lymph nodes failed to develop in TNF-β −/− mice. In addition, peripheral blood from TNF-β −/− mice contained a three fold reduction in white blood cells as compared to normal mice. Peripheral blood from TNF-β −/− mice, however, contained four fold more B cells as compared to their normal counterparts. Further, TNF-β, in contrast to TNF-α has been shown to induce proliferation of EBV-infected B cells. These results indicate that TNF-β is involved in lymphocyte development.

The first step in the induction of the various cellular responses mediated by TNF-α or TNF-β is their binding to specific cell surface or soluble receptors. Two distinct TNF receptors of approximately 55-KDa (TNF-RI) and 75-KDa (TNF-RII) have been identified (Hohman et al., *J. Biol. Chem.*, 264:14927-14934 (1989)), and human and mouse cDNAs corresponding to both receptor types have been isolated and characterized (Loetscher et al., *Cell*, 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar et al., *EMBO Journal*, 9 (10):3269-76 (1990)) and otherwise intact receptors wherein the transmembrane domain is lacking. The extracellular domains of TNF-RI and TNF-RII share 28% identity and are characterized by four repeated cysteine-rich motifs with significant intersubunit sequence homology. The majority of cell types and tissues appear to express both TNF receptors and both receptors are active in single transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase $A_2$, protein-kinase C, phosphatidylcholine-specific phospholipase C and sphingomyelinase Pfeffer, K. et al., *Cell*, 73: 457-467 (1993)).

Several interferons and other agents have been shown to regulate the expression of TNF receptors. Retinoic acid, for example, has been shown to induce the production of TNF receptors in some cells type while down regulating production in other cells. In addition, TNF-α has been shown effect the localization of both types of receptor. TNF-α induces internalization of TNF-RI and secretion of TNF-RII (reviewed in Aggarwal et al., supra). Thus, the production and localization of both TNF-Rs are regulated by a variety of agents.

Both the yeast two hybrid system and co-precipitation and purification have been used to identify ligands which associate with both types of the TNF-Rs (reviewed in Aggarwal et al., supra and Vandenbeele et al., *Trends in Cell Biol.* 5:392-399 (1995)). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

SUMMARY OF THE INVENTION

The present invention provides isolated nucleic acid molecules comprising polynucleotides encoding a TR2 receptor and splice variants thereof having the amino acid sequences shown in FIGS. 1A-1B (SEQ ID NO:2), FIGS. 4A-4C (SEQ ID NO:5) and FIGS. 7A-7C (SEQ ID NO:8) or the amino acid sequence encoded by the cDNA clone encoding the TR2 receptors deposited in bacterial hosts as ATCC Deposit Numbers 97059, 97058 and 97057 on Feb. 13, 1995. The present invention also relates to recombinant vectors, which include the isolated nucleic acid molecules of the present invention, and to host cells containing the recombinant vectors, as well as to methods of making such vectors and host cells and for using them for production of TR2 polypeptides or peptides by recombinant techniques.

The invention further provides isolated TR2 polypeptides having amino acid sequences encoded by the polynucleotides described herein.

The present invention also provides a screening method for identifying compounds capable of enhancing or inhibiting a cellular response induced by TR2 receptors, which involves contacting cells which express TR2 receptors with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on the binding of cellular ligands to TR2 receptors. In particular, the method involves contacting TR2 receptors with a ligand polypeptide and a candidate compound and determining whether ligand binding to the TR2 receptors is increased or decreased due to the presence of the candidate compound.

The invention further provides a diagnostic method useful during diagnosis or prognosis of a disease states resulting from aberrant cell proliferation due to alterations in TR2 receptor expression.

An additional aspect of the invention is related to a method for treating an individual in need of an increased level of a TR2 receptor activity in the body comprising administering to such an individual a composition comprising a therapeutically effective amount of isolated TR2 polypeptides of the invention or an agonist thereof.

A still further aspect of the invention is related to a method for treating an individual in need of a decreased level of a TR2 receptor activity in the body comprising, administering to such an individual a composition comprising a therapeutically effective amount of a TR2 receptor antagonist.

The invention additionally provides soluble forms of the polypeptides of the present invention. Soluble peptides are defined by amino acid sequences wherein the sequence comprises the polypeptide sequences lacking a transmembrane domain. Such soluble forms of the TR2 receptors are useful as antagonists of the membrane bound forms of the receptors.

BRIEF DESCRIPTION OF THE FIGURES

FIGS. 1A-1B shows the nucleotide (SEQ ID NO:1) and deduced amino acid (SEQ ID NO:2) sequences of a TR2 receptor. The protein has a predicted leader sequence of about 36 amino acid residues (underlined) (amino acid residues −36 to −1 in SEQ ID NO:2) and a deduced molecular weight of about 30,417 kDa. It is further predicted that amino acid residues from about 37 to about 200 (amino acid residues 1 to 164 in SEQ ID NO:2) constitute the extracellular domain; from about 201 to about 225 (amino acid residues 165 to 189 in SEQ ID NO:2) the transmembrane domain (underlined); and from about 226 to about 283 (amino acid residues 190 to 247 in SEQ ID NO:2) the intracellular domain. Two potential aspargine-linked glycosylation sites are located at amino acid positions 110 and 173 (amino acid residues 74 to 137 in SEQ ID NO:2).

FIG. 2 shows the regions of similarity between the amino acid sequences of the TR2 receptor protein of FIGS. 1A-1B and a murine CD40 protein (SEQ ID NO:3) (percent similarity: 46.591; percent identity: 28.788).

FIGS. 4A-4C shows the nucleotide (SEQ ID NO:4) and deduced amino acid (SEQ ID NO:5) sequences of the TR2-SV1 receptor. The protein has a predicted leader sequence of about 36 amino acid residues (underlined) (amino acid residues −36 to −1 in SEQ ID NO:5) and a deduced molecular weight of about 19.5 kDa.

FIG. 5 shows the regions of similarity between the amino acid sequences of the full-length TR2-SV1 receptor protein and a human type 2 TNF receptor (SEQ ID NO:6) (percent similarity is 47.541; percent identity: 24.590).

FIGS. 7A-7C shows the nucleotide (SEQ ID NO:7) and deduced amino acid (SEQ ID NO:8) sequences of the TR2-SV2 receptor. This protein lacks a putative leader sequence and has a deduced molecular weight of about 14 kDa.

FIG. 8 shows the regions of similarity between the amino acid sequences of the TR2-SV2 receptor protein and a human type 2 TNF receptor (SEQ ID NO:9) (percent similarity: 45.522; percent identity: 26.866).

FIG. 10 shows the regions of similarity between the amino acid sequences of the TR2 receptor protein of FIGS. 1A-1B and the TR2-SV1 receptor protein of FIGS. 4A-4C (percent similarity: 73.370; percent identity: 9.783).

FIG. 11 shows the regions of similarity between the amino acid sequences of the TR2 receptor protein of FIGS. 1A-1B and the TR2-SV2 receptor protein of FIGS. 7A-7C (percent similarity: 70.588; percent identity is 60.294).

FIG. 12 shows the regions of similarity between the amino acid sequences of the TR2-SV1 and the TR2-SV2 receptor proteins (percent similarity: 37.984; percent identity: 20.155).

FIGS. 13A-13D shows the regions of similarity between the nucleotide sequences encoding the TR2 receptor protein of FIGS. 1A-1B and TR2-SV1 receptor protein of FIGS. 4A-4C (percent similarity: 92.168; percent identity: 92.168).

FIGS. 14A-14D shows the regions of similarity between the nucleotide sequences encoding the TR2 receptor protein of FIGS. 1A-1B and the TR2-SV2 receptor protein of FIGS. 7A-7C.

FIGS. 15A-15F shows the regions of similarity between the nucleotide sequences encoding the TR2-SV1 and the TR2-SV2 receptor proteins (percent similarity: 53.479; percent identity: 53.479).

FIG. 16 shows an alignment of the amino acid sequence of the TR2 receptor of FIGS. 1A-1B (SEQ ID NO:2) with other TNFR family members. The amino acid sequence of TR2 was aligned with those of TNFR-I (SEQ ID NO:10), TNFR-II (SEQ ID NO:11), CD40 (SEQ ID NO:12) and 4-1BB (SEQ ID NO:13) on the basis of sequence homology and conserved cysteine residues.

DETAILED DESCRIPTION OF THE PREFERRED EMBODIMENTS

Figure 3:
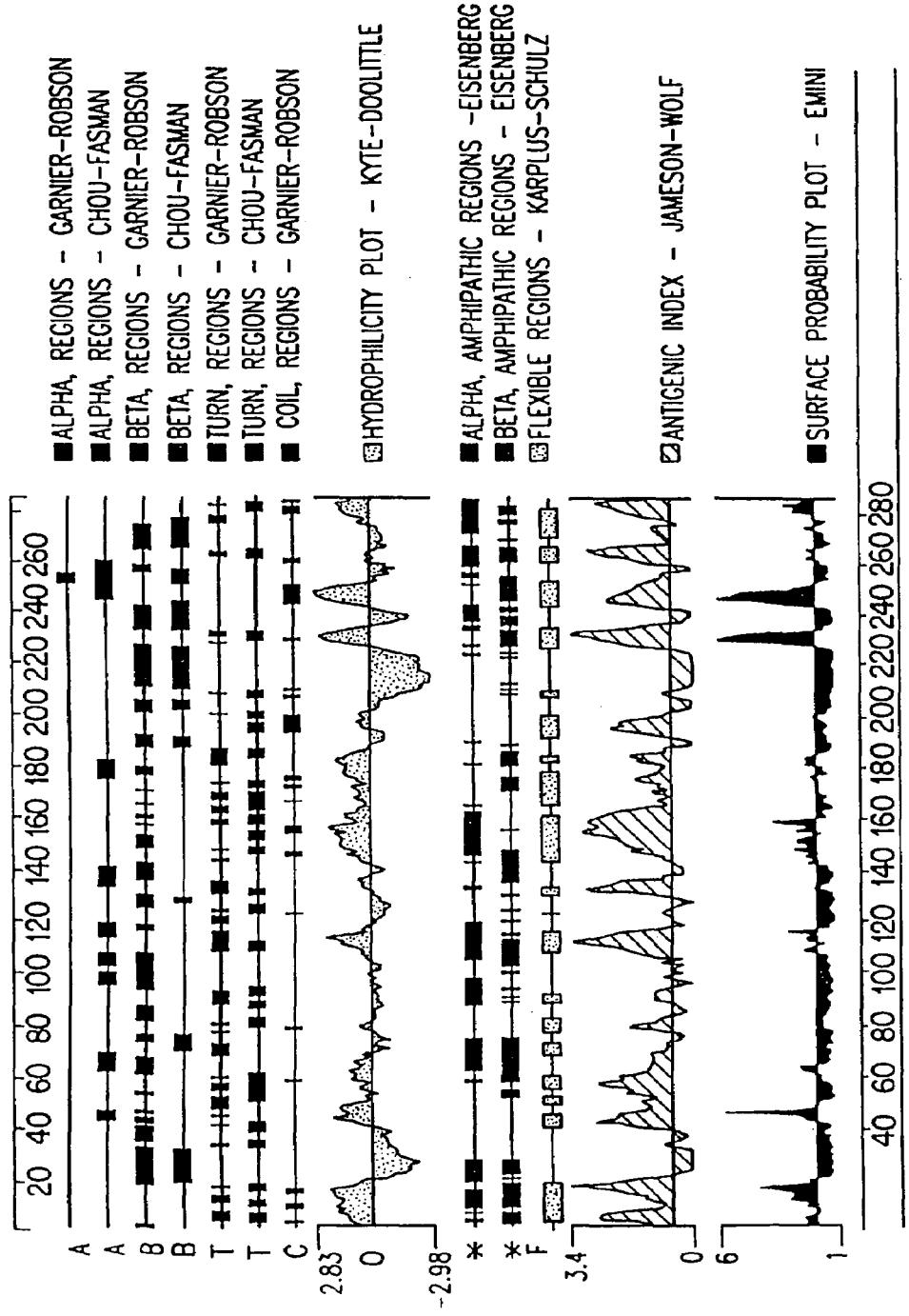
FIG. 3 shows an analysis of the TR2 receptor amino acid sequence of FIGS. 1A-1B. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 39 to 70, 106 to 120, 142 to 189 and 276 to 283 in FIGS. 1A-1B (amino acid residues 3 to 34, 70 to 84, 106 to 153 and 240 to 247 in SEQ ID NO:2) correspond to the shown highly antigenic regions of the TR2 receptor protein.
Figure 6:
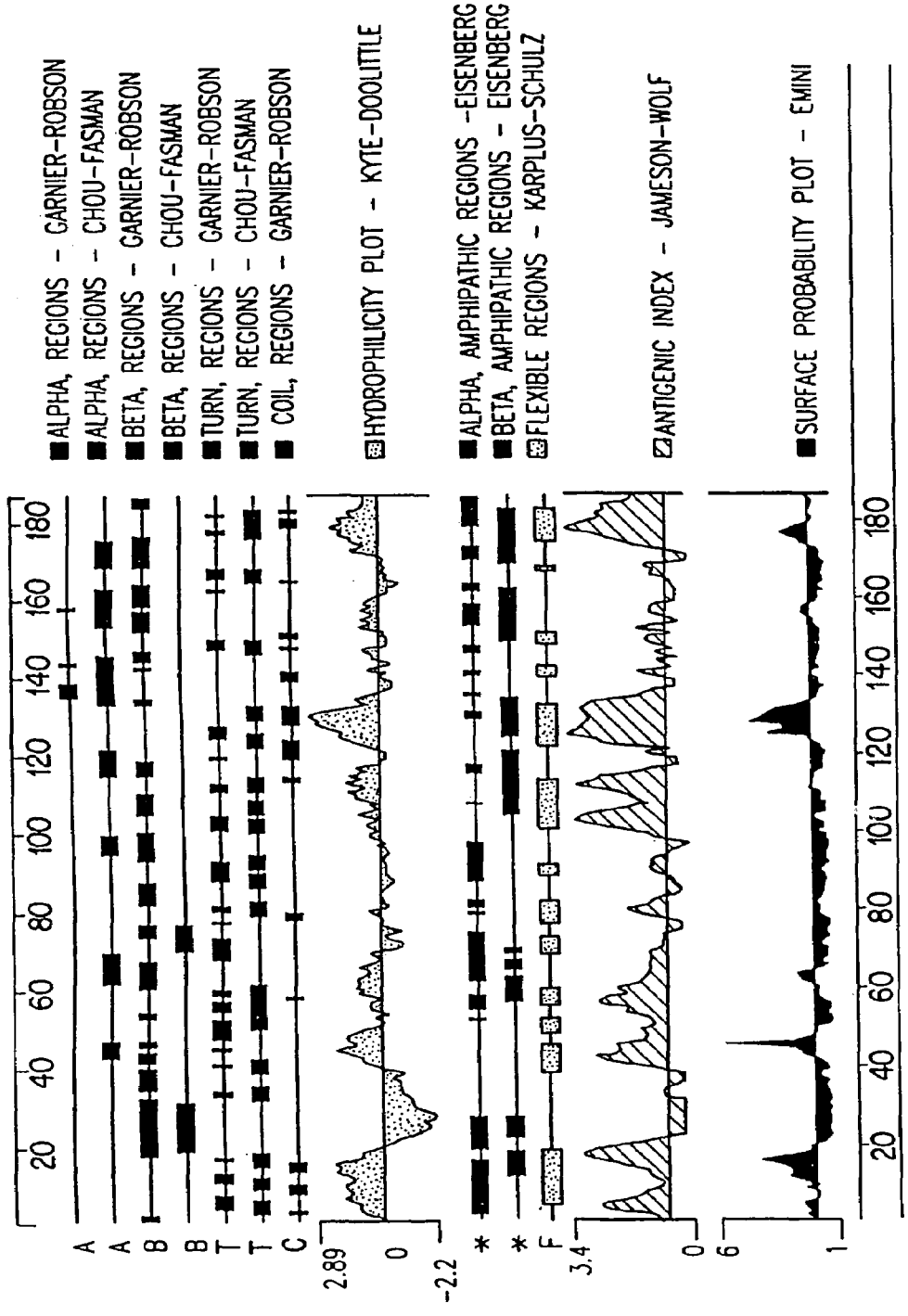
FIG. 6 shows an analysis of the TR2-SV1 receptor amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 39 to 70, 99 to 136 and 171 to 185 in FIGS. 4A-4C (amino acid residues 3 to 34, 63 to 100 and 135 to 149 in SEQ ID NO:5) correspond to the shown highly antigenic regions of the TR2-SV1 receptor protein.
Figure 9:
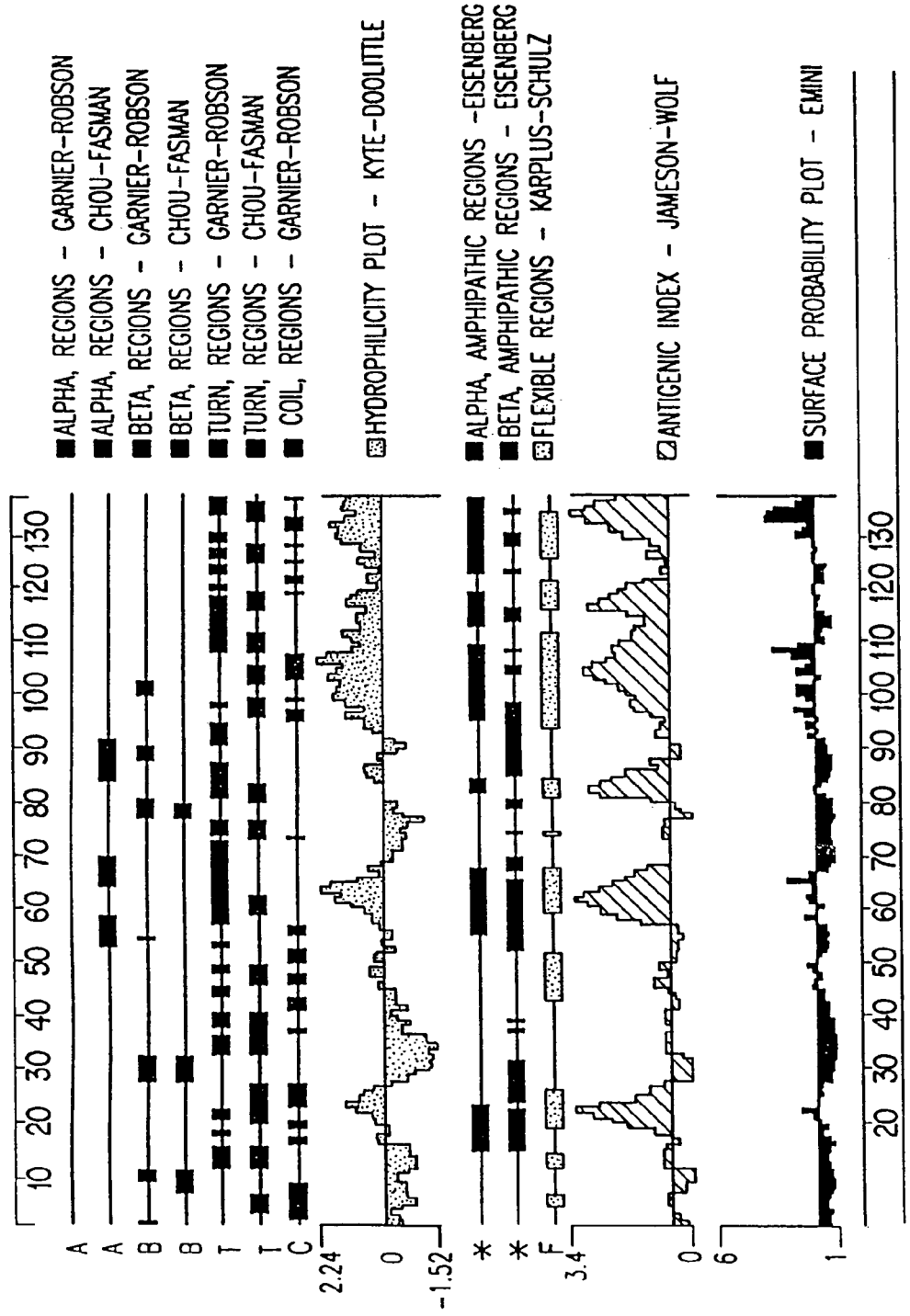
FIG. 9 shows an analysis of the TR2-SV2 receptor amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 56 to 68 and 93 to 136 in FIGS. 7A-7C (SEQ ID NO:8) correspond to the shown highly antigenic regions of the TR2-SV2 receptor protein.

The present invention provides isolated nucleic acid molecules comprising polynucleotides encoding a TR2 polypeptide (FIGS. 1A-1B (SEQ ID NO:2)) and splice variants thereof, TR2-SV1 (FIGS. 4A-4C (SEQ ID NO:5)) and TR2-SV2 (FIGS. 7A-7C (SEQ ID NO:8)), the amino acid sequences of which were determined by sequencing cloned cDNAs. The TR2 proteins shown in FIGS. 1A-1B shares sequence homology with the murine CD40 receptor (FIG. 2 (SEQ ID NO:3)). On Feb. 13, 1995 a deposit was made at the American Type Culture Collection, 12301 Parklawn Drive, Rockville, Md. 20852, and given accession number 97059. The nucleotide sequence shown in FIGS. 1A-1B (SEQ ID NO:1) was obtained by sequencing a cDNA clone (Clone ID HLHAB49) containing the same amino acid coding sequences as the clone in ATCC Accession No. 97059 with minor deviation. The cDNA sequence shown in FIGS. 1A-1B (SEQ ID NO:1) differs from that of the ATCC deposit in the 5' and 3' noncoding nucleotide sequences and three nucleotides.

The clone deposited in ATCC Accession No. 97059 contains 8 nucleotides 5' to the TR2 initiation codon and 21 nucleotides 3' to the TR2 stop codon. In contrast, the TR2 cDNA sequence of HLHAB49, shown in FIGS. 1A-1B (SEQ ID NO.1), contains considerably longer non-coding nucleotides sequence on both the 5' and 3' ends of the TR2 coding sequences. Further, the TR2 receptor nucleotide sequence shown in FIGS. 1A-1B (SEQ ID NO:1) contains an adenine at nucleotide 314, a cytosine at nucleotide 386, and a cytosine at nucleotide 627. In contrast, the clone of ATCC Accession No. 97059 contains a guanine at nucleotide 314, a thymine at nucleotide 386, and a thymine at nucleotide 627.

The TR2 receptors of the present invention include several allelic variants containing alterations in at least these three nucleotides and two amino acids. Nucleotide sequence variants which have been identified include either guanine or adenine at nucleotide 314, thymine or cytosine at nucleotide 386, and thymine or cytosine at nucleotide 627 shown in FIGS. 1A-1B (SEQ ID NO:1). While the identified alteration at nucleotide 627 is silent, the alteration at nucleotide 386 results in the codon at nucleotides 385 to 387 encoding either serine or phenylalanine and the alteration at nucleotide 314 results in the codon at nucleotides 313 to 315 encoding either lysine or arginine.

The nucleotide sequences shown in FIGS. 4A-4C (SEQ ID NO:4) and FIGS. 7A-7C (SEQ ID NO:7) were also obtained by sequencing cDNA clones deposited on Feb. 13, 1995 at the American Type Culture Collection and given accession numbers 97058 (TR2-SV1) and 97057 (TR2-SV2), respectively. The deposited clones are contained in the pBluescript SK(−) plasmid (Stratagene, LaJolla, Calif.).

As used herein the phrase "splice variant" refers to cDNA molecules produced from a RNA molecules initially transcribed from the same genomic DNA sequence which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

As used herein, "TR2 proteins", "TR2 receptors", "TR2 receptor proteins" and "TR2 polypeptides" refer to all proteins resulting from the alternate splicing of the genomic DNA sequences encoding proteins having regions of amino acid sequence identity and receptor activity which correspond to the proteins shown in FIGS. 1A-1B (SEQ ID NO:2), FIGS. 4A-4C (SEQ ID NO:5) or FIGS. 7A-7C (SEQ ID NO:8). The TR2 protein shown in FIGS. 1A-1B, the TR2-SV1 protein shown FIGS. 4A-4C and the TR2-SV2 protein shown in FIGS. 7A-7C are examples of such receptor proteins.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-1B, FIGS. 4A-4C or FIGS. 7A-7C, nucleic acid molecules of the present invention encoding TR2 polypeptides may be obtained using standard cloning and screening procedures, such as those used for cloning cDNAs using mRNA as starting material. Illustrative of the invention, the nucleic acid molecule described in FIGS. 1A-1B (SEQ ID NO:1) was discovered in a cDNA library derived from activated human T-lymphocytes. The nucleic acid molecules described in FIGS. 4A-4C (SEQ ID NO:4) and FIGS. 7A-7C (SEQ ID NO:7) were discovered in cDNAs library derived from human fetal heart and human stimulated monocytes, respectively.

As described in Example 6, TR2 mRNA was detected in numerous tissues including lung, spleen and thymus and may be ubiquitously expressed in human cells. TR2 RNA was also found to be expressed in B lymphocytes (CD19$^+$), both CD4$^+$ ($T_{H1}$ and $T_{h2}$ clones) and CD8$^+$ T lymphocytes, monocytes and endothelial cells.

As also noted in Example 6, the production of TR2 mRNA was inducible in MG 63 cells by TNFα. Further, the accumulation of TR2 mRNA was observed in HL60, U937 and THP1 cells upon PMA or DMSO treatment. PMA and DMSO are agents known to induce differentiation of these three cell types.

The determined nucleotide sequence of the TR2 cDNA of FIGS. 1A-1B (SEQ ID NO:1) contains an open reading frame encoding a protein of about 283 amino acid residues, with a predicted leader sequence of about 36 amino acid residues, and a deduced molecular weight of about 30,417 kDa. The amino acid sequence of the predicted mature TR2 receptor is shown in FIGS. 1A-1B from amino acid residue about 37 to residue about 283 (amino acid residues 1 to 247 in SEQ ID NO:2). As noted in Example 6, the location of the leader sequence cleavage site was confirmed for a TR2-Fc fusion protein and found to be between amino acids 36 and 37 shown in FIGS. 1A-1B (amino acid residues −1 to 1 in SEQ ID NO:2). The TR2 protein shown in FIGS. 1A-1B (SEQ ID NO:2) is about 29% identical and about 47% similar to the murine CD40 protein shown in SEQ ID NO:3 (see FIG. 2).

Similarly, the determined cDNA nucleotide sequences of the TR2-SV1 splice variant of TR2 (FIGS. 4A-4C (SEQ ID NO:4)) contains an open reading frame encoding a protein of about 185 amino acid residues, with a predicted leader sequence of about 36 amino acid residues, and a deduced molecular weight of about 19.5 kDa. The amino acid sequence of the predicted mature TR2-SV1 receptor is shown in FIGS. 4A-4C (SEQ ID NO:5) from amino acid residue about 37 to residue about 185 (amino acid residues 1 to 149 in (SEQ ID NO:5). The TR2-SV1 protein shown in FIGS. 4A-4C (SEQ ID NO:5) is about 25% identical and about 48% similar to the human type 2 TNF receptor protein shown in SEQ ID NO:6 (see FIG. 5).

The determined cDNA nucleotide sequences of the TR2-SV2 splice variant of TR2 (FIGS. 7A-7C (SEQ ID NO:7)) contains an open reading frame encoding a protein of about 136 amino acid residues, without a predicted leader sequence, and a deduced molecular weight of about 14 kDa. The amino acid sequence of the predicted TR2-SV2 receptor is shown in FIGS. 7A-7C (SEQ ID NO:8) from amino acid residue about 1 to residue about 136. The TR2-SV2 protein shown in FIGS. 7A-7C (SEQ ID NO:8) is about 27% identical and about 45% similar to the human type 2 TNF receptor protein shown in SEQ ID NO: 9 (see FIG. 8).

A comparison of both the nucleotide and amino acid sequences of the TR2, TR2-SV1 and TR2-SV2 receptor proteins shown in FIGS. 1A-1B, FIGS. 4A-4C and FIGS. 7A-7C shows several regions of near identity. While the amino acid sequence of the TR2 receptor protein, shown in FIGS. 1A-1B (SEQ ID NO:2), is about 60% identical and about 73% similar to the amino acid sequence of the TR2-SV1 receptor protein, shown in FIGS. 4A-4C (SEQ ID NO:5), in approximately the first one hundred amino acids of their respective sequences the two protein differ in one location (FIG. 10).

Similarly, the amino acid sequence of the TR2 receptor protein of FIGS. 1A-1B (SEQ ID NO:2) is about 60% identical and about 71% similar to the amino acid sequence of the TR2-SV2 receptor protein, shown in FIGS. 7A-7C (SEQ ID NO:8); however, the two proteins are almost identical over a 60 amino acid stretch in the central portion of the TR2-SV2 protein (FIG. 11).

In contrast, the TR2-SV1 and TR2-SV2 proteins are only about 20% identical and about 38% similar at the amino acid level to each other. Unlike the comparisons of either of these proteins to the TR2 protein shown in FIGS. 1A-1B (SEQ ID NO:2), these proteins share their homology over the entire 136 amino acid sequence of the TR2-SV2 protein (FIG. 12).

With respect to their nucleotide sequences of the cDNAs encoding the disclosed TR2 proteins, a comparison of these sequences indicates that the TR2 cDNAs share large regions of near identity at the nucleic acid level (FIGS. 13A-13D, FIGS. 14A-14D and FIGS. 15A-15F). The cDNA sequences encoding the TR2 and TR2-SV1 proteins, for example, share large regions of near identity in their nucleotide sequences which encode both the N termini of the respective proteins and their 5' and 3' noncoding regions (FIGS. 13A-13D). Further, the nucleotide sequences of the cDNAs encoding the TR2-SV1 and TR2-SV2 proteins share considerable homology but this identity is limited to their 3' regions well beyond their respective coding sequences (FIGS. 15A-15F).

Such regions of near identity between two different cDNA sequences, when maintained over an extended stretch of sequence, indicates to one skilled in the art that the respective molecules were originally transcribed from the same genomic DNA sequence. One skilled in the art would further recognize that, since more than one codon can encode the same amino acid, identity between two proteins at the amino acid level does not necessarily mean that the DNA sequences encoding those proteins will share similar regions of identity. The above data indicates that the TR2 receptors of the present invention are transcribed from a single genomic DNA sequence and represent multiple splice variants of one initial RNA transcript.

Related proteins which are produced from alternately spliced RNA, referred to as splice variants, are known in the art. The transcript of the src gene, for example, undergoes alternate RNA splicing to produce cell type specific products. In most cells the Src protein consists of 533 amino acids while in nerve cells an additional short exon is included in the mRNA resulting in a protein of 539 amino acids. See Alberts, B. et al., MOLECULAR BIOLOGY OF THE CELL (3rd Edition, Garland Publishing, Inc., 1994), 455. Similarly, sex specific mRNA transcripts have been identified in *Drosophila* where alternate mRNA splicing results in a protein named Dsx which is approximately 550 amino acids in length in males and 430 amino acids in length in females. These two splice variant proteins share a common core sequence of about 400 amino acids. See id. at 457.

In the present instance, the TR2 receptor protein shown in FIGS. 1A-1B (SEQ ID NO:2) is believed to be the full-length polypeptide encoded by the RNA from which the TR2 receptor proteins are translated. The RNA encoding the TR2-SV1 splice variant is shown in FIGS. 4A-4C (SEQ ID NO:5) is believed to contain an insertion in the region encoding amino acid residue 102 of the amino acid sequence shown in FIGS 1A-1B and a deletion in the region encoding amino acid residue 184 of the amino acid sequence shown in FIGS. 1A-1B. The RNA encoding the TR2-SV2 splice variant shown in FIGS. 7A-7C is believed to begin with the nucleotide sequence encoding amino acid residue 102 of the amino acid sequence shown in FIGS. 1A-1B and contain insertions in the regions encoding amino acid residues 184 and 243 of the amino acid sequence shown in FIGS. 1A-1B.

As indicated, the present invention also provides the mature forms of the TR2 receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides nucleotide sequences encoding mature TR2 polypeptides having the amino acid sequences encoded by the cDNA clones contained in the host identified as ATCC Deposit Numbers 97059 and 97058 and as shown in FIGS. 1A-1B (SEQ ID NO:2) and FIGS. 4A-4C (SEQ ID NO:5). By the mature TR2 polypeptides having the amino acid sequences encoded by the cDNA clones contained in the host identified as ATCC Deposit Numbers 97059 and 97058 is meant the mature form(s) of the TR2 receptors produced by expression in a mammalian cell (e.g., COS cells, as described below) of the complete open reading frame encoded by the human DNA sequence of the clone contained in the vector in the deposited host.

The invention also provides nucleic acid sequences encoding the TR2-SV2 receptor protein of FIGS. 7A-7C (SEQ ID NO:8), having the amino acid sequence encoded by the cDNA clone contained in ATCC Deposit Number 97057, which does not contain a secretory leader sequence.

Methods for predicting whether a protein has a secretory leader as well as the cleavage point for that leader sequence are available. For instance, the methods of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80% von Heinje, supra. However, the two methods do not always produce the same predicted cleavage point(s) for a given protein.

In the present case, the predicted amino acid sequences of the complete TR2 polypeptides shown in FIGS. 1A-1B (SEQ ID NO:2), FIGS. 4A-4C (SEQ ID NO:5) and FIGS. 7A-7C (SEQ ID NO:8) were analyzed by a computer program ("PSORT") (K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids −1 and 1 in SEQ ID NO:2 and SEQ ID NO:5. Thereafter, the complete amino acid sequences were further analyzed by visual inspection, applying a simple form of the (−1, −3) rule of von Heine. von Heinje, supra. Thus, the leader sequences for the TR2 protein shown in SEQ ID NO:2 and the TR2-SV1 protein are predicted to consist of amino acid residues 31 36 to −1 in both SEQ ID NO:2 and SEQ ID NO:5, while the predicted mature TR2 proteins consist of amino acid residues 1 to 247 to the TR2 protein shown in SEQ ID NO:2 and residues 1 to 149 for the TR2-SV1 protein shown in SEQ ID NO:5.

As noted in Example 6, the cleavage site of the leader sequence of a TR2-Fc Fusion protein was confirmed using amino acid analysis of the expressed fusion protein. This fusion protein was found to begin at amino acid 37, which corresponds to amino acid 1 in SEQ ID NO:2 and SEQ ID NO:5, indicating that the cleavage site of the leader sequence is between amino acids 36 and 37 in this protein (corresponding to amino acid residues −1 to 1 in SEQ ID NO:2 and SEQ ID NO:5).

As one of ordinary skill would appreciate, however, due to the possibilities of sequencing errors, as well as the variability of cleavage sites for leaders in different known proteins, the TR2 receptor polypeptide encoded by the cDNA of ATCC Deposit Number 97059 comprises about 283 amino acids, but may be anywhere in the range of 250 to 316 amino acids; and the leader sequence of this protein is about 36 amino acids, but may be anywhere in the range of about 30 to about 42 amino acids. Similarly, the TR2-SV1 receptor polypeptide encoded by the cDNA of ATCC Deposit Number 97058 comprises about 185 amino acids, but may be anywhere in the range of 163-207 amino acids; and the leader sequence of this protein is about 36 amino acids, but may be anywhere in the range of about 30 to about 42 amino acids. Further, the TR2-SV2 receptor polypeptide encoded by the cDNA of ATCC Deposit number 97057 comprises about 136 amino acids, but may be anywhere in the range of 120-152 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A-1B (SEQ ID NO:1); DNA molecules comprising the coding sequence for the mature TR2 receptor shown in FIGS. 1A-1B (SEQ ID NO:2) (last 247 amino acids); and DNA molecules which comprise a sequence substantially different from those described above but which, due to the degeneracy of the genetic code, still encode the TR2 receptor protein shown in FIGS. 1A-1B (SEQ ID NO:2). Of course, the genetic code is well known in the art. Thus, it would be routine for one skilled in the art to generate such degenerate variants.

Similarly, isolated nucleic acid molecules of the present invention include DNA molecules comprising an open reading frame (ORF) shown in FIGS. 4A-4C (SEQ ID NO:4); DNA molecules comprising the coding sequence for the mature TR2-SR1 receptor shown in FIGS. 4A-4C (SEQ ID NO:5) (last 149 amino acids); and DNA molecules which comprise a sequence substantially different from those described above but which, due to the degeneracy of the genetic code, still encode the TR2-SV1 receptor.

Further, isolated nucleic acid molecules of the present invention include DNA molecules comprising an open reading frame (ORF) shown in FIGS. 7A-7C (SEQ ID NO:7) and DNA molecules which comprise a sequence substantially different from those described above but which, due to the degeneracy of the genetic code, still encode the TR2-SV2 receptor.

In another aspect, the invention provides isolated nucleic acid molecules encoding the TR2, TR2-SV1 and TR2-SV2 polypeptides having the amino acid sequences encoded by the cDNA clones contained in the plasmid deposited as ATCC Deposit No. 97059, 97058 and 97057, respectively, on Feb. 13, 1995. In a further embodiment, these nucleic acid molecules will encode a mature polypeptide or the full-length polypeptide lacking the N-terminal methionine. The invention further provides isolated nucleic acid molecules having the nucleotide sequences shown in FIGS. 1A-1B (SEQ ID NO:1), FIGS. 4A-4C (SEQ ID NO:4), and FIGS. 7A-7C (SEQ ID NO:7); the nucleotide sequences of the cDNAs contained in the above-described deposited clones; or nucleic acid molecules having a sequence complementary to one of the above sequences. Such isolated molecules, particularly DNA molecules, are useful as probes for gene mapping, by in situ hybridization with chromosomes, and for detecting expression of the TR2 receptor genes of the present invention in human tissue, for instance by Northern blot analysis.

The present invention is further directed to fragments of the isolated nucleic acid molecules described herein. By a fragment of an isolated nucleic acid molecule having the nucleotide sequence of the deposited cDNAs or the nucleotide sequence shown in FIGS. 1A-1B (SEQ ID NO:1), FIGS. 4A-4C (SEQ ID NO:4), or FIGS. 7A-7C (SEQ ID NO:7) is intended fragments at least about 15 nt, and more preferably at least about 20 nt, still more preferably at least about 30 nt, and even more preferably, at least about 40 in length which are useful as diagnostic probes and primers as discussed herein. Of course, larger fragments 50-400 nt in length are also useful according to the present invention as are fragments corresponding to most, if not all, of the nucleotide sequences of the deposited cDNAs or as shown in FIGS. 1A-1B (SEQ ID NO:1), FIGS. 4A-4C (SEQ ID NO:4), or FIGS. 7A-7C (SEQ ID NO:7). By a fragment at least 20 nt in length, for example, is intended fragments which include 20 or more contiguous bases from the nucleotide sequences of the deposited cDNAs or the nucleotide sequences as shown in FIGS. 1A-1B (SEQ ID NO:1), FIGS. 4A-4C (SEQ ID NO:4), or FIGS. 7A-7C (SEQ ID NO:7).

Preferred nucleic acid fragments of the present invention include nucleic acid molecules encoding: a polypeptide comprising the TR2 receptor protein of FIGS. 1A-1B (SEQ ID NO:2) extracellular domain (predicted to constitute amino acid residues from about 37 to about 200 in FIGS. 1A-1B (amino acid residues 1 to 164 in SEQ ID NO:2)); a polypeptide comprising the TR2 receptor transmembrane domain (amino acid residues 201 to 225 in FIGS. 1A-1B (amino acid residues 165 to 189 in SEQ ID NO:2)); a polypeptide comprising the TR2 receptor intracellular domain (predicted to constitute amino acid residues from about 226 to about 283 in FIGS. 1A-1B (amino acid residues 190 to 247 in SEQ ID NO:2)); and a polypeptide comprising the TR2 receptor protein of FIGS. 1A-1B (SEQ ID NO:2) extracellular and intracellular domains with all or part of the transmembrane domain deleted.

Preferred nucleic acid fragments of the present invention also include nucleic acid molecules encoding polypeptides comprising the mature TR2-SV1 receptor (predicted to constitute amino acid residues from about 37 to about 185 in FIGS. 4A-4C (amino acid residues 1 to 149 in SEQ ID NO:5)) and the complete TR2-SV2 receptor (predicted to constitute amino acid residues from about 1 to about 136 in FIGS. 7A-7C (SEQ ID NO:8)).

As above with the leader sequence, the amino acid residues constituting the extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the TR2 receptor proteins. In particular, such nucleic acid fragments of the present invention include nucleic acid molecules encoding: a polypeptide comprising amino acid residues from about 39 to about 70 in FIGS. 1A-1B (amino acid residues 3 to 34 in SEQ ID NO:2); a polypeptide comprising amino acid residues from about 106 to about 120 in FIG. 1 (amino acid residues 70 to 84 in SEQ ID NO:2); a polypeptide comprising amino acid residues from about 142 to about 189 in FIGS. 1A-1B (amino acid residues 106 to 153 in SEQ ID NO:2); a polypeptide comprising amino acid residues from about 276 to about 283 in FIGS. 1A-1B (amino acid residues 240 to 247 in SEQ ID NO:2); a polypeptide comprising amino acid residues from about 39 to about 70 in FIGS. 4A-4C (amino acid residues 3 to 34 in SEQ ID NO:5); amino acid residues from about 99 to about 136 in FIGS. 4A-4C (amino acid residues 63 to 100 in SEQ ID NO:5); amino acid residues from about 171 to about 185 in FIGS. 4A-4C (amino acid residues 135 to 149 in SEQ ID NO:5); amino acid residues from about 56 to about 68 in FIGS. 7A-7C (SEQ ID NO:8); amino acid residues from about 93 to about 136 in FIGS. 7A-7C (SEQ ID NO:8). The inventors have determined that the above polypeptide fragments are antigenic regions of the TR2 receptors. Methods for determining other such epitope-bearing portions of the TR2 proteins are described in detail below.

In another aspect, the invention provides isolated nucleic acid molecules comprising polynucleotides which hybridizes under stringent hybridization conditions to a portion of the polynucleotide of one of the nucleic acid molecules of the invention described above, for instance, the cDNA clones contained in ATCC Deposits 97059, 97058 and 97057. By "stringent hybridization conditions" is intended overnight incubation at 42° C. in a solution comprising: 50% formamide, 5x SSC (750 mM NaCl, 75 mM trisodium citrate), 50 mM sodium phosphate (pH 7.6), 5x Denhardt's solution, 10% dextran sulfate, and 20 ug/ml denatured, sheared salmon sperm DNA, followed by washing the filters in 0.1x SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequences as shown in FIGS. 1A-1B (SEQ ID NO:1), FIGS. 4A-4C (SEQ ID NO:4), or FIGS. 7A-7C (SEQ ID NO:7)).

Of course, a polynucleotide which hybridizes only to a poly A sequence (such as the 3' terminal poly(A) tract of the TR2 receptor cDNA sequences shown in FIGS. 1A-1B (SEQ ID NO:1), FIGS. 4A-4C (SEQ ID NO:4), or FIGS. 7A-7C (SEQ ID NO:7)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode TR2 polypeptides may include, but are not limited to those encoding the amino acid sequences of the mature polypeptides, by itself, the coding sequence for the mature polypeptides and additional sequences, such as those encoding the about 36 amino acid leader or secretory sequences, such as pre-, or pro- or prepro-protein sequences; the coding sequence of the mature polypeptides, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the TR2 receptors fused to IgG—Fc at the N- or C-terminus.

The present invention further relates to variants of the nucleic acid molecules of the present invention, which encode portions, analogs or derivatives of the TR2 receptors. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR2 receptors or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the TR2 polypeptide having the complete amino acid sequence shown in FIGS. 1A-1B (amino acid residues −36 to 247 in SEQ ID NO:2), FIGS. 4A-4C (amino acid residues −36 to 149 in SEQ ID NO:5), or FIGS. 7A-7C (amino acid residues 1 to 136 in SEQ ID NO:8); (b) a nucleotide encoding the complete amino sequence shown in FIGS. 1A-1B (amino acid residues −35 to 247 in SEQ ID NO:2), FIGS. 4A-4C (amino acid residues −35 to 149 in SEQ ID NO:5), or FIGS. 7A-7C (amino acid residues 2 to 136 in SEQ ID NO:8) but lacking the N-terminal methionine; (c) a nucleotide sequence encoding the mature TR2 receptors (full-length polypeptide with any attending leader sequence removed) having the amino acid sequence at positions from about 37 to about 283 in FIGS. 1A-1B (amino acid residues 1 to 247 in SEQ ID NO:2) or the amino acid sequence at positions from about 37 to about 185 in FIGS. 4A-4C (amino acid residues 1 to 149 in SEQ ID NO:5), or the amino acid sequence at positions from about 1 to about 136 in FIGS. 7A-7C (SEQ ID NO:8); (d) a nucleotide sequence encoding the TR2, TR2-SV1 or TR2-SV2 polypeptides having the complete amino acid sequence including the leader encoded by the cDNA clones contained in ATCC Deposit Numbers 97059, 97058, and 97057, respectively; (e) a nucleotide sequence encoding the mature TR2 and TR2-SV1 receptors having the amino acid sequences encoded by the cDNA clones contained in ATCC Deposit Numbers 97059 and 97058, respectively; (f) a nucleotide sequence encoding the TR2 or TR2-SV1 receptor extracellular domain; (g) a nucleotide sequence encoding the TR2 receptor transmembrane domain; (h) a nucleotide sequence encoding the TR2 receptor intracellular domain; (i) a nucleotide sequence encoding the TR2 receptor extracellular and intracellular domains with all or part of the transmembrane domain deleted; and (j) a nucleotide sequence complementary to any of the nucleotide sequences in (a), (b), (c), (d), (e), (f), (g), (h), or (i).

By a polynucleotide having a nucleotide sequence at least, for example, 95% "identical" to a reference nucleotide sequence encoding a TR2 polypeptide is intended that the nucleotide sequence of the polynucleotide is identical to the reference sequence except that the polynucleotide sequence may include up to five point mutations per each 100 nucleotides of the reference nucleotide sequence encoding the TR2 receptors. In other words, to obtain a polynucleotide having a nucleotide sequence at least 95% identical to a reference nucleotide sequence. up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A-1B (SEQ ID NO:1) or to the nucleotides sequence of the deposited cDNA clone encoding that protein can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequences shown in FIGS. 1A-1B (SEQ ID NO:1), FIGS. 4A-4C (SEQ ID NO:4), or FIGS. 7A-7C (SEQ ID NO:7) or to the nucleic acid sequence of the deposited cDNAs, irrespective of whether they encode a polypeptide having TR2 receptor activity. This is because even where a particular nucleic acid molecule does not encode a polypeptide having TR2 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR2 receptor activity include, inter alia, (1) isolating a TR2 receptor gene or allelic or splice variants thereof in a cDNA library; (2) in situ hybridization (e.g., "FISH") to metaphase chromosomal spreads to provide precise chromosomal location of a TR2 receptor gene, as described in Verma et al., *Human Chromosomes: A Manual of Basic Techniques*, Pergamon Press, New York (1988); and (3) Northern Blot analysis for detecting TR2 receptor mRNA expression in specific tissues.

Preferred, however, are nucleic acid molecules having sequences at least 90%, 95%, 96%, 97%, 98%, or 99% identical to the nucleic acid sequence shown in FIGS. 1A-1B (SEQ ID NO:1), FIGS. 4A-4C (SEQ ID NO:4), or FIGS. 7A-7C (SEQ ID NO:7) or to the nucleic acid sequence of the deposited cDNAs which do, in fact, encode a polypeptide having TR2 receptor activity. By "a polypeptide having TR2 receptor activity" is intended polypeptides exhibiting activity similar, but not necessarily identical, to an activity of the TR2 receptors of the present invention (either the full-length protein, the splice variants, or, preferably, the mature protein), as measured in a particular biological assay. For example, TR2 receptor activity can be measured by determining the ability of a polypeptide-Fc fusion protein to inhibit lymphocyte proliferation as described below in Example 6. TR2 receptor activity may also be measured by determining the ability of a polypeptide, such as cognate ligand which is free or expressed on a cell surface, to confer proliferatory activity in intact cells expressing the receptor.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNAs or the nucleic acid sequences shown in FIGS. 1A-1B (SEQ ID NO:1), FIGS. 4A-4C (SEQ ID NO:4), or FIGS. 7A-7C (SEQ ID NO:7) will encode polypeptides "having TR2 receptor activity." In fact, since degenerate variants of any of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of TR2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicilin resistance genes for culturing in *E. coli* and other bacteria. Representative examples of appropriate heterologous hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods, Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunization. In drug discovery, for example, human proteins, such as, human hIL-5 receptor has been fused with Fc portions for the purpose of high-throughput screening assays to identify antagonists of hIL-5, See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

TR2 receptors can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

TR2 Polypeptides and Fragments

The invention further provides isolated TR2 polypeptides having the amino acid sequence encoded by the deposited cDNAs, or the amino acid sequence in FIGS. 1A-1B (SEQ ID NO:2), FIGS. 4A-4C (SEQ ID NO:5), or FIGS. 7A-7C (SEQ ID NO:8), or a peptide or polypeptide comprising a portion of the above polypeptides.

The polypeptides of this invention may be membrane bound or may be in a soluble circulating form. Soluble peptides are defined by amino acid sequence wherein the sequence comprises the polypeptide sequence lacking the transmembrane domain. One example of such a soluble form of the TR2 receptor is the TR2-SV1 splice variant which has a secretory leader sequence but lacks both the intracellular and transmembrane domains. Thus, the TR2-SV1 receptor protein appears to be secreted in a soluble form from cells which express this protein.

The polypeptides of the present invention may exist as a membrane bound receptor having a transmembrane region and an intra- and extracellular region or they may exist in soluble form wherein the transmembrane domain is lacking. One example of such a form of the TR2 receptor is the TR2 receptor shown in FIGS. 1A-1B (SEQ ID NO:2) which contains, in addition to a leader sequence, transmembrane, intracellular and extracellular domains. Thus, this form of the TR2 receptor appears to be localized in the cytoplasmic membrane of cells which express this protein.

It will be recognized in the art that some amino acid sequences of the TR2 receptors can be varied without significant effect to the structure or function of the protein. If such differences in sequence are contemplated, it should be remembered that there will be critical areas on the protein which determine activity. Thus, the invention further includes variations of the TR2 receptors which show substantial TR2 receptor activity or which include regions of TR2 proteins such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptides of FIGS. 1A-1B (SEQ ID NO:2), FIGS. 4A-4C (SEQ ID NO:5), and FIGS. 7A-7C (SEQ ID NO:8), or that encoded by the deposited cDNAs, may be (i) one in which one or more of the amino acid residues are substituted with a conserved or non-conserved amino acid residue (preferably a conserved amino acid residue (and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR2 proteins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the TR2 receptors of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

CONSERVATIVE AMINO ACID SUBSTITUTIONS.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TR2 proteins of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the TR2 receptors can be substantially purified by the one-step method described in Smith and Johnson, *Gene* 67:31-40 (1988).

The polypeptides of the present invention also include the polypeptide encoded by the deposited cDNAs including the leader; the polypeptide encoded by the deposited the cDNAs minus the leader (i.e., the mature protein); the polypeptides of FIGS. 1A-1B (SEQ ID NO:2) or FIGS. 4A-4C (SEQ ID NO:5) including the leader; the polypeptides of FIGS. 1A-1B (SEQ ID NO:2) or FIGS. 4A-4C (SEQ ID NO:5) including the leader but minus the N-terminal methionine; the polypeptides of FIGS. 1A-1B (SEQ ID NO:2) or FIGS. 4A-4C (SEQ ID NO:5) minus the leader; the polypeptide of FIGS. 7A-7C (SEQ ID NO:8); the extracellular domain, the transmembrane domain, and the intracellular domain of the TR2 receptor shown in FIGS. 1A-1B (SEQ ID NO:2); and polypeptides which are at least 80% identical, more preferably at least 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR2 polypeptide is intended that the amino acid sequence of the polypeptide is identical to the reference sequence except that the polypeptide sequence may include up to five amino acid alterations per each 100 amino acids of the reference amino acid of a TR2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A-1B (SEQ ID NO:2), FIGS. 4A-4C (SEQ ID NO:5), or FIGS. 7A-7C (SEQ ID NO:8) or to the amino acid sequence encoded by one of the deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention could be used as a molecular weight marker on SDS-PAGE gels or on molecular sieve gel filtration columns using methods well known to those of skill in the art.

In another aspect, the invention provides peptides or polypeptides comprising epitope-bearing portions of the polypeptides of the invention. The epitopes of these polypeptide portions are an immunogenic or antigenic epitopes of the polypeptides described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate TR2 receptor-specific antibodies include: a polypeptide comprising amino acid residues from about 39 to about 70 in FIG. 1 (amino acid residues 3 to 34 in SEQ ID NO:2); a polypeptide comprising amino acid residues from about 106 to about 120 in FIGS. 1A-1B (amino acid residues 70 to 84 in SEQ ID NO:2); a polypeptide comprising amino acid residues from about 142 to about 189 in FIGS. 1A-1B (amino acid residues 106 to 153 in SEQ ID NO:2); a polypeptide comprising amino acid residues from about 276 to about 283 in FIG. 1 (amino acid residues 240 to 247 in SEQ ID NO:2); a polypeptide comprising amino acid residues from about 39 to about 70 in FIGS. 4A-4C (amino acid residues 3 to 34 in SEQ ID NO:5); a polypeptide comprising amino acid residues from about 99 to about 136 in FIGS. 4A-4C (amino acid residues 63 to 100 in SEQ ID NO:5); a polypeptide comprising amino acid residues from about 171 to about 185 in FIGS. 4A-4C (amino acid residues 135 to 149 in SEQ ID NO:5); a polypeptide comprising amino acid residues from about 56 to about 68 in FIGS. 7A-7C (SEQ ID NO:8); and a polypeptide comprising amino acid residues from about 93 to about 136 in FIGS. 7A-7C (SEQ ID NO:8). As indicated above, the inventors have determined that the above polypeptide fragments are antigenic regions of the TR2 receptor proteins.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 92:5131-5135. This "Simultaneous Multiple Peptide Synthesis (SMPS)" process is further described in U.S. Pat. No. 4,631,211 to Houghten et al. (1986).

As one of skill in the art will appreciate, TR2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric TR2 receptor proteins or protein fragments alone (Fountoulakis et al., *J. Biochem* 270:3958-3964 (1995)).

Detection of Disease States

The TNF-family ligands induce various cellular responses by binding to TNF-family receptors, including the TR2 receptors of the present invention. TNF-β, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Homer, *Prog. Allergy*, 40:162-182 (1988)). TNF-α, also a ligand of the TNF receptor proteins, has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al, *J. Immunol.* 136(7):2483 (1987); Porter, *Tibtech* 9:158-162 (1991)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

Cells which express the TR2 polypeptides and are believed to have a potent cellular response to TR2 receptor ligands include B lymphocytes (CD19$^+$), both CD4$^+$ and CD8$^+$ T lymphocytes, monocytes, endothelial cells and other cell types shown in Tables 2 and 3. By "a cellular response to a TNF-family ligand" is intended any genotypic, phenotypic, and/or morphologic change to a cell, cell line, tissue, tissue culture of patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis. Apoptosis-programmed cell death—is a physiological mechanism involved in the deletion of peripheral T lymphocytes of the immune system, and its dysregulation can lead to a number of different pathogenic processes (Ameisen, J. C., *AIDS* 8:1197-1213 (1994); Krammer, P. H. et al., *Curr. Opin. Immunol.* 6:279-289 (1994)).

It is believed that certain tissues in mammals with specific disease states associated with aberrant cell survival express significantly altered levels of the TR2 receptor protein and mRNA encoding the TR2 receptor protein when compared to a corresponding "standard" mammal, i.e., a mammal of the same species not having the disease state. Further, since some forms of this protein are secreted, it is believed that enhanced levels of the TR2 receptor protein can be detected in certain body fluids (e.g., sera, plasma, urine, and spinal fluid) from mammals with the disease state when compared to sera from mammals of the same species not having the disease state. Thus, the invention provides a diagnostic method useful during diagnosis of disease states, which involves assaying the expression level of the gene encoding the TR2 receptor protein in mammalian cells or body fluid and comparing the gene expression level with a standard TR2 receptor gene expression level, whereby an increase or decrease in the gene expression level over the standard is indicative of certain disease states associated with aberrant cell survival.

Where diagnosis of a disease state involving the TR2 receptors of the present invention has already been made according to conventional methods, the present invention is useful as a prognostic indicator, whereby patients exhibiting significantly aberrant TR2 receptor gene expression will experience a worse clinical outcome relative to patients expressing the gene at a lower level.

By "assaying the expression level of the gene encoding the TR2 receptor protein" is intended qualitatively or quantitatively measuring or estimating the level of the TR2 receptor protein or the level of the mRNA encoding the TR2 receptor protein in a first biological sample either directly (e.g., by determining or estimating absolute protein level or mRNA level) or relatively (e.g., by comparing to the TR2 receptor protein level or mRNA level in a second biological sample).

Preferably, the TR2 receptor protein level or mRNA level in the first biological sample is measured or estimated and compared to a standard TR2 receptor protein level or mRNA level, the standard being taken from a second biological sample obtained from an individual not having the disease state. As will be appreciated in the art, once a standard TR2 receptor protein level or mRNA level is known, it can be used repeatedly as a standard for comparison.

By "biological sample" is intended any biological sample obtained from an individual, cell line, tissue culture, or other source which contains TR2 receptor protein or mRNA. Biological samples include mammalian body fluids (such as sera, plasma, urine, synovial fluid and spinal fluid) which contain secreted mature TR2 receptor protein, and thymus, prostate, heart, placenta, muscle, liver, spleen, lung, kidney and other tissues. Methods for obtaining tissue biopsies and body fluids from mammals are well known in the art. Where the biological sample is to include mRNA, a tissue biopsy is the preferred source.

Diseases associated with increased cell survival, or the inhibition of apoptosis, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, or increased apoptosis, include AIDS, neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Assays available to detect levels of soluble receptors are well known to those of skill in the art, for example, radioimmunoassays, competitive-binding assays, Western blot analysis, and preferably an ELISA assay may be employed.

TR2 receptor-protein specific antibodies can be raised against the intact TR2 receptor protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (mAb) is meant to include intact molecules as well as antibody fragments (such as, for example, Fab and F(ab')$_2$ fragments) which are capable of specifically binding to TR2 receptor protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the TR2 receptor protein or an antigenic fragment thereof can be administered to an animal in order to induce the production of sera containing polyclonal antibodies. In a preferred method, a preparation of TR2 receptor protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TR2 receptor protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563-681). In general, such procedures involve immunizing an animal (preferably a mouse) with a TR2 receptor protein antigen or, more preferably, with a TR2 receptor protein-expressing cell. Suitable cells can be recognized by their capacity to bind anti-TR2 receptor protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas Va. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the TR2 receptor protein antigen.

Agonists and Antagonists of TR2 Receptor Function

In one aspect, the present invention is directed to a method for inhibiting an activity of TR2 induced by a TNF-family ligand (e.g., cell proliferation, hematopoietic development), which involves administering to a cell which expresses a TR2 polypeptide an effective amount of a TR2 receptor ligand, analog or an antagonist capable of decreasing TR2, receptor mediated signaling. Preferably, TR2 receptor mediated signaling is increased to treat a disease wherein increased cell proliferation is exhibited. An antagonist can include soluble forms of the TR2 receptors and antibodies directed against the TR2 polypeptides which block TR2 receptor mediated signaling. Preferably, TR2 receptor mediated signaling is decreased to treat a disease.

In a further aspect, the present invention is directed to a method for increasing cell proliferation induced by a TNF-family ligand, which involves administering to a cell which expresses a TR2 polypeptide an effective amount of an agonist capable of increasing TR2 receptor mediated signaling. Preferably, TR2 receptor mediated signaling is increased to treat a disease wherein decreased cell proliferation is exhibited. Agonists of the present invention include monoclonal antibodies directed against the TR2 polypeptides which stimulate TR2 receptor mediated signaling. Preferably, TR2 receptor mediated signaling is increased to treat a disease.

By "agonist" is intended naturally occurring and synthetic compounds capable of enhancing cell proliferation and differentiation mediated by TR2 polypeptides. Such agonists include agents which increase expression of TR2 receptors or increase the sensitivity of the expressed receptor. By "antagonist" is intended naturally occurring and synthetic compounds capable of inhibiting TR2 mediated cell proliferation and differentiation. Such antagonists include agents which decrease expression of TR2 receptors or decrease the sensitivity of the expressed receptor. Whether any candidate "agonist" or "antagonist" of the present invention can enhance or inhibit cell proliferation and differentiation can be determined using art-known TNF-family ligand/receptor cellular response assays, including those described in more detail below.

One such screening technique involves the use of cells which express the receptor (for example, transfected CHO cells) in a system which measures extracellular pH changes caused by receptor activation, for example, as described in *Science* 246:181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR2 receptors are contacted with ligands in the extracellular medium after they are secreted. A determination is then made as to whether the secreted protein will bind to TR2 receptor ligands.

Further screening assays for agonist and antagonist of the present invention are described in Tartaglia, L. A., and Goeddel, D. V., *J. Biol. Chem.* 267(7):4304-4307 (1992).

Thus, in a further aspect, a screening method is provided for determining whether a candidate agonist or antagonist is capable of enhancing or inhibiting a cellular response to a TNF-family ligand. The method involves contacting cells which express TR2 polypeptides with a candidate compound and a TNF-family ligand, assaying a cellular response, and comparing the cellular response to a standard cellular response, the standard being assayed when contact is made with the ligand in absence of the candidate compound, wherein an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritated thymidine labeling). By the invention, a cell expressing a TR2 polypeptide can be contacted with either an endogenous or exogenously administered TNF-family ligand.

In an additional aspect, a thymocyte proliferation assay may be employed to identify both ligands and potential drug candidates. For example, thymus cells are disaggregated from tissue and grown in culture medium. Incorporation of DNA precursors such as $^3$H-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up as above and TNF-β or cognate ligand is added to all wells while soluble receptor polypeptides of the present invention are added individually to the second control wells, with the experimental well containing a compound to be screened. The ability of the compound to be screened to stimulate or inhibit the above interaction may then be quantified.

Agonists according to the present invention include compounds such as, for example, TNF-family ligand peptide fragments, transforming growth factor β, and neurotransmitters (such as glutamate, dopamine, N-methyl-D-aspartate). Preferred agonist include polyclonal and monoclonal antibodies raised against TR2 polypeptide, or a fragment thereof. Such agonist antibodies raised against a TNF-family receptor are disclosed in Tartaglia, L. A., et al., *Proc. Natl. Acad. Sci. USA* 88:9292-9296 (1991); and Tartaglia, L. A., and Goeddel, D. V., *J. Biol. Chem.* 267 (7):4304-4307 (1992). See, also, PCT Application WO 94/09137. Further preferred agonists include chemotherapeutic drugs such as, for example, cisplatin, doxorubicin, bleomycin, cytosine arabinoside, nitrogen mustard, methotrexate and vincristine. Others include ethanol and β-amyloid peptide. (*Science* 267:1457-1458 (1995)).

Antagonist according to the present invention include soluble forms of the TR2 receptors (e.g., fragments of the TR2 receptor shown in FIGS. 1A-1B that include the ligand binding domain from the extracellular region of the full length receptor). Such soluble forms of the receptor, which may be naturally occurring or synthetic, antagonize TR2, TR2-SV1 or TR2-SV2 mediated signaling by competing with the cell surface bound forms of the receptor for binding to TNF-family ligands. Antagonists of the present invention also include antibodies specific for TNF-family ligands and TR2-Fc fusion proteins such as the one described below in Examples 5 and 6.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, TNF-α, lymphotoxin-α (LT-α, also known as TNF-β), LT-β (found in complex heterotrimer LT-α2-β). FasL, CD40L, CD27L, CD30L, 4-1BBL, OX40L and nerve growth factor (NGF).

The experiments set forth in Example 6 demonstrate that the TR2 receptors of the present invention are capable of inducing the proliferation of lymphocytes. Further, such proliferation can be inhibited by a TR2 protein fragment fused to an Fc antibody fragment.

TNFα has been shown to protect mice from infection with herpes simplex virus type 1 (HSV-1). Rossol-Voth, R. et al., *J. Gen. Virol.* 72:143-147 (1991). The mechanism of the protective effect of TNFα is unknown but appears to involve neither interferons not NK cell killing. One member of the TNFR family has been shown to mediate HSV-1 entry into cells. Montgomery, R. et al., *Eur. Cytokine Newt.* 7:159 (1996). Further, antibodies specific for the extracellular domain of this TNFR block HSV-1 entry into cells. Thus, TR2 receptors of the present invention include both TR2 amino acid sequences and antibodies capable of preventing TNFR mediated viral entry into cells. Such sequences and antibodies can function by either competing with cell surface localized TNFR for binding to virus or by directly blocking binding of virus to cell surface receptors.

Antibodies according to the present invention may be prepared by any of a variety of methods using TR2 receptor immunogens of the present invention. Such TR2 receptor immunogens include the TR2 receptor protein shown in FIGS. 1A-1B (SEQ ID NO:2) and the TR2-SV1 (FIGS. 4A-4C (SEQ ID NO:5)) and TR2-SV2 (FIGS. 7A-7C (SEQ ID NO:8)) polypeptides (any of which may or may not include a leader sequence) and polypeptide fragments of the receptors comprising the ligand binding, extracellular, transmembrane, the intracellular domains of the TR2 receptors, or any combination thereof.

Polyclonal and monoclonal antibody agonist or antagonist according to the present invention can be raised accordingly to the methods disclosed in Tartaglia and Goeddel, *J. Biol. Chem.* 267(7):4304-4307(1992)); Tartaglia et al., *Cell* 73:213-216 (1993)), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies: A Laboratory Manual*, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the TR2 receptor domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al., *Cell* 72:223-232 (1993)). Preferably, the yeast two-hybrid system is used according to the present invention to capture compounds which bind to the ligand binding, extracellular, intracellular, and transmembrane domains of the TR2 receptors. Such compounds are good candidate agonist and antagonist of the present invention.

Using the two-hybrid assay described above, the intracellular domain of the TR2 receptor, or a portion thereof, may be used to identify cellular proteins which interact with the receptor in vivo. Such an assay may also be used to identify ligands with potential agonistic or antagonistic activity of TR2 receptor function. This screening assay has previously been used to identify protein which interact with the cytoplasmic domain of the murine TNF-RII and led to the identification of two receptor associated proteins. Rothe, M. et al., *Cell* 78:681 (1994). Such proteins and amino acid sequences which bind to the cytoplasmic domain of the TR2 receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science*, 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

The TR2 receptor agonists may be employed to stimulate ligand activities, such as inhibitors of tumor growth and necrosis of certain transplantable tumors. The agonists may also be employed to stimulate cellular differentiation, for example, T-cell, fibroblasts and hemopoietic cell differentiation. Agonists to the TR2 receptor may also augment TR2's role in the host's defense against microorganisms and prevent related diseases (infections such as that from *Listeria monocytogenes*) and Chlamidiae. The agonists may also be employed to protect against the deleterious effects of ionizing radiation produced during a course of radiotherapy, such as denaturation of enzymes, lipid peroxidation, and DNA damage.

Agonists to the receptor polypeptides of the present invention may be used to augment TNF's role in host defenses against microorganisms and prevent related diseases. The agonists may also be employed to protect against the deleterious effects of ionizing radiation produced during a course of radiotherapy, such as denaturation of enzymes, lipid peroxidation, and DNA damage.

The agonists may also be employed to mediate an anti-viral response, to regulate growth, to mediate the immune response and to treat immunodeficiencies related to diseases such as HIV by increasing the rate of lymphocyte proliferation and differentiation.

The antagonists to the polypeptides of the present invention may be employed to inhibit ligand activities, such as stimulation of tumor growth and necrosis of certain transplantable tumors. The antagonists may also be employed to inhibit cellular differentiation, for example, T-cell, fibroblasts and hemopoietic cell differentiation. Antagonists may also be employed to treat autoimmune diseases, for example, graft versus host rejection and allograft rejection, and T-cell mediated autoimmune diseases such as AIDS. It has been shown that T-cell proliferation is stimulated via a type 2 TNF receptor. Accordingly, antagonizing the receptor may prevent the proliferation of T-cells and treat T-cell mediated autoimmune diseases.

The state of immunodeficiency that defines AIDS is secondary to a decrease in the number and function of CD4$^+$ T-lymphocytes. Recent reports estimate the daily loss of CD4+ T cells to be between 3.5×10$^7$ and 2×10$^9$ cells (Wei X., et al., *Nature* 373:117-122 (1995)). One cause of CD4+ T cell depletion in the setting of HIV infection is believed to be HIV-induced apoptosis. Indeed, HIV-induced apoptopic cell death has been demonstrated not only in vitro but also, more importantly, in infected individuals (Ameisen, J. C., *AIDS* 8:1197-1213 (1994); Finkel, T. H., and Banda, N. K., *Curr. Opin. Immunol.* 6:605-615 (1995); Muro-Cacho, C. A. et al., *J. Immunol.* 154:5555-5566 (1995)). Furthermore, apoptosis and CD4+ T-lymphocyte depletion is tightly correlated in different animal models of AIDS (Brunner, T., et al., *Nature* 373:441-444 (1995); Gougeon, M. L., et al., *AIDS Res. Hum. Retroviruses* 9:553-563 (1993)) and, apoptosis is not observed in those animal models in which viral replication does not result in AIDS (Gougeon, M. L. et al., *AIDS Res. Hum. Retroviruses* 9:553-563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199-206 (1996)). Further the TNF-family ligand was detectable in uninfected macrophages and its expression was unregulated following HIV infection resulting in selective killing of uninfected CD4+ T-lymphocytes (Badley, A. D et al., *J. Virol.* 70:199-206 (1996)).

As shown in Example 6, the TR2 receptor shown in FIGS. 1A-1B is expressed in CD4+ T-lymphocytes and is capable of inducing lymphocyte proliferation. Thus, by the invention, a method for treating HIV+ individuals is provided which involves administering an agonist of the present invention to increase the rate of proliferation and differentiation of CD4+ T-lymphocytes. Such agonists include agents capable of inducing the expression of TR2 receptors (e.g., TNFα, PMA and DMSO) or enhancing the signal of such receptors which induces lymphocyte proliferation and differentiation. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antagonists of the present invention are able to suppress the immune response to both allografts and xenografts by decreasing the rate of TR2 mediated lymphocyte proliferation and differentiation. Such antagonists include the TR-2-Fc fusion protein described in Examples 5 and 6. Thus, the present invention further provides a method for suppression of immune responses.

In addition, TNFα has been shown to prevent diabetes in strains of animals which are prone to this affliction resulting from autoimmunity. See Porter, A., *Tibtech* 9:158-162 (1991). Thus, agonists and antagonists of the present invention may be useful in the treatment of autoimmune diseases such as type 1 diabetes.

In addition, the role played by the TR2 receptors in cell proliferation and differentiation indicates that agonist or antagonist of the present invention may be used to treat disease states involving aberrant cellular expression of these receptors. TR2 receptors may in some circumstances induce an inflammatory response, and antagonists may be useful reagents for blocking this response. Thus TR2 receptor antagonists (e.g., soluble forms of the TR2 receptors; neutralizing antibodies) may be useful for treating inflammatory diseases, such as rheumatoid arthritis, osteoarthritis, psoriasis, septicemia, and inflammatory bowel disease.

Antagonists to the TR2 receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that antagonists to the TR2 receptor will block the actions of TNF and treat/prevent septic shock. These antagonists may also be employed to treat meningococcemia in children which correlates with high serum levels of TNF.

Among other disorders which may be treated by the antagonists to TR2 receptors, there are included, inflammation which is mediated by TNF receptor ligands, and the bacterial infections cachexia and cerebral malaria. The TR2 receptor antagonists may also be employed to treat inflammation mediated by ligands to the receptor such as TNF.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR2 receptor mediated activity. Of course, where cell proliferation and/or differentiation is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or pro-drug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of a TR2 polypeptide administered parentally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR2 polypeptide is typically administered at a dose rate of about 1 μg/kg/hour to about 50

μg/kg/hour, either by 1-4 injections per day or by continuous subcutaneous infusions, for example, using a mini-pump. An intravenous bag solution may also be employed.

Pharmaceutical compositions containing the TR2 receptor polypeptides of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Having generally described the invention, the same will be more readily understood by reference to the following examples, which are provided by way of illustration and are not intended as limiting.

EXAMPLE 1

Expression and Purification of TR2 in *E. Coli*

The bacterial expression vector pQE60 is used for bacterial expression in this example. (QIAGEN, Inc., 9259 Eton Avenue, Chatsworth, Calif., 91311). pQE60 encodes ampicilin antibiotic resistance ("Amp") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6 X His tag") covalently linked to the carboxyl terminus of that polypeptide. However, in this example, the polypeptide coding sequence is inserted such that translation of the six His codons is prevented and, therefore, the polypeptide is produced with no 6 X His tag.

The DNA sequence encoding the desired portion of the TR2 protein lacking the hydrophobic leader sequence is amplified from the deposited cDNA clone using PCR oligonucleotide primers which anneal to the amino terminal sequences of the desired portion of the TR2 protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence: 5' CGCCCATGGCCCCAGCTCTGCCGTCCT 3' (SEQ ID NO:14) containing the underlined NcoI restriction site followed by 18 nucleotides complementary to the amino terminal coding sequence of the mature TR2 sequence in FIGS. 1A-1B. One of ordinary skill in the art would appreciate, of course, that the point in the protein coding sequence where the 5' primer begins may be varied to amplify a desired portion of the complete protein shorter or longer than the mature form. The 3' primer has the sequence:

5' CGCAAGCTTATTGTGGGAGCTGCTGGTCCC 3' (SEQ ID NO:15) containing the underlined HindIII restriction site followed by 18 nucleotides complementary to the 3' end of the nucleotide sequence shown in FIGS. 1A-1B (SEQ ID NO:1) encoding the extracellular domain of the TR2 receptor.

The amplified TR2 DNA fragments and the vector pQE60 are digested with NcoI and HindIII and the digested DNAs are then ligated together. Insertion of the TR2 DNA into the restricted pQE60 vector places the TR2 protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual*, 2nd Ed; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing TR2 protein, is available commercially from QIAGEN, Inc., supra. Transformants are identified by their ability to grow on LB plates in the presence of ampicilin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicilin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3-4 hours at 4° C. in 6 M guanidine-HCl, pH 8. The cell debris is removed by centrifugation, and the supernatant containing the TR2 is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as in antibody column can be used to obtain pure TR2 protein. The purified protein is stored at 4° C. or frozen at −80° C.

EXAMPLE 2

Example 2(a)

Cloning and Expression of a Soluble Fragment of TR2 Protein in a Baculovirus Expression System In this example, the plasmid shuttle vector pA2 GP was used to insert the cloned DNA encoding the mature extracellular domain of the TR2 receptor protein shown in FIGS. 1A-1B, lacking its naturally associated secretory signal (leader) sequence, into a baculovirus. This protein was expressed using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39.

The cDNA sequence encoding essentially the mature extracellular domain (amino acids 37 to 200 shown in FIGS. 1A-1B) of the TR2 receptor protein in the deposited clone (ATCC Deposit Number 97059) was amplified using PCR oligonucleotide primers corresponding to the relevant 5' and 3' sequences of the gene. The 5' primer for each of the above has the sequence:

5' CGCGGATCCCGGAGCCCCCTGCTAC 3' (SEQ ID NO:16) containing the underlined BamHI restriction enzyme site, an efficient signal for initiation of transaction in eukaryotic cells, as described by Kozak, M., *J. Mol. Biol.* 196:947-950 (1987), followed by 15 bases of the coding sequence of the TR2 protein shown in FIGS. 1A-1B, beginning with the nucleotide 354. The 3' primer has the sequence:

5' CGCGGTACCATTGTGGGAGCTGCTGGTCCC 3' (SEQ ID NO:17) containing the underlined, Asp718 restriction sites followed by 17 nucleotides complementary to the coding sequences in FIGS. 1A-1B.

The amplified fragment was isolated from a 1% agarose gel using a commercially available kit ("Geneclean," BIO 101 Inc., La Jolla, Calif.). The fragment was then digested with BamHI and Asp718 and purified on a 1% agarose gel. This fragment is designated herein "F1".

The plasmid was digested with the restriction enzymes BamHI and Asp718 dephosphorylated using calf intestinal phosphatase. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 cells were transformed with the ligation mixture and spread on culture plates. Other suitable *E. coli* hosts such as XL-1 Blue (Stratagene Cloning systems, La Jolla, Calif.) may also be used. Bacteria were identified that contain the plasmid with the human TR2 sequences using the PCR method, in which one of the primers that was used to amplify the gene and the second primer was from well within the vector so that only those bacterial colonies containing TR2 gene fragments show amplification of the DNA. The sequence of the cloned fragment was confirmed by DNA sequencing. The plasmid was designated herein pBacTR2-T.

Five µg of pBacTR2-T was co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413-7417 (1987). 1 µg of BaculoGold™ virus DNA and 5 µg of plasmid pBacTR2-T were mixed in a sterile well of a microtiter plate containing 50 µl of serum-free Grace's medium (Life Technologies Inc., Gaithersburg, Md.). Afterwards, 10 µl Lipofectin plus 90 µl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation was continued at 27° C. for four days.

After four days the supernatant was collected and a plaque assay was performed, as described by Summers and Smith, supra. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Page 9-10). After appropriate incubation, blue stained plaques were picked with the tip of a micropipettor (e.g., Eppendorf). The agar containing the recombinant viruses was then resuspended in a microcentrifuge tube containing 200 µl of Grace's medium and the suspension containing the recombinant baculovirus was used to infect Sf9 cells seeded in 35 mm dishes. Four days later the supernatants of these culture dishes were harvested and then they were stored at 4° C. The recombinant virus is called V-TR2-T.

To verify the expression of the gene used, Sf9 cells were grown in Grace's medium supplemented with 10% heat inactivated FBS. The cells were infected with the recombinant baculovirus V-TR2-T at a multiplicity of infection ("MOI") of about 2. Six hours later the medium was removed and replaced with SF900 II medium minus methionine and cysteine (available from Life Technologies Inc., Rockville, Md.). Forty-two hours later, 5 µCi of $^{35}$S-methionine and 5 µCi $^{35}$S-cysteine (available from Amersham) were added to radio-label proteins. The cells were further incubated for 16 hours and then they were harvested by centrifugation. The proteins in the supernatant as well as the intracellular proteins were analyzed by SDS-PAGE followed by autoradiography. Microsequencing of the amino acid sequence of the amino terminus of purified protein was used to determine the amino terminal sequence of the mature protein and thus the cleavage point and length of the secretory signal peptide.

EXAMPLE 2(b)

Cloning and Expression of TR2 Protein in a Baculovirus Expression System

Similarly to the cloning and expression of the truncated version of the TR2 receptor described in Example 2(a), recombinant baculoviruses were generated which express the full length TR2 receptor protein shown in FIGS. 1A-1B (SEQ ID NO:2).

In this example, the plasmid shuttle vector pA2 was used to insert the cloned DNA encoding the complete protein, including its naturally associated secretary signal (leader) sequence, into a baculovirus to express the mature TR2 protein. Other attributes of the pA2 vector are as described for the pA2 GP vector used in Example 2(a).

The cDNA sequence encoding the full length TR2 protein in the deposited clone, including the AUG initiation codon and the naturally associated leader sequence shown in FIGS.

1A-1B (SEQ ID NO:2), was amplified using PCR oligonucleotide primers corresponding to the 5' and 3' sequences of the gene. The 5' primer has the sequence:

5' GCGCGGATCCACCATGGAGCCTCCTG-GAGACTGG3' (SEQ ID NO:18) containing the underlined BamHI restriction enzyme site, an efficient signal for initiation of translation in eukaryotic cells, as described by Kozak, M., *J. Mol. Biol.* 196:947-950 (1987), followed by 21 bases of the sequence of the complete TR2 protein shown in FIGS. 1A-1B, beginning with the AUG initiation codon. The 3' primer has the sequence:

5' GCGCGGTACCCTCTACCCCAGCAGGGGCGCCA 3' (SEQ ID NO:19) containing the underlined, Asp718 restriction site followed by 21 nucleotides complementary to the 3' noncoding sequence in FIGS. 1A-1B.

The amplified fragment was isolated and digested with restriction enzymes as described in Example 2(a) to produce plasmid pBacTR2

5 µg of pBacTR2 was co-transfected with 1 µg of BaculoGold™ (Pharmingen) viral DNA and 10 µl of Lipofectin™ (Life Technologies, Inc.) in a total volume of 200 µl serum free media. The primary viruses were harvested at 4-5 days post-infection (pi), and used in plaque assays. Plaque purified viruses were subsequently amplified and frozen, as described in Example 2(a).

For radiolabeling of expressed proteins, Sf9 cells were seeded in 12 well dishes with 2.0 ml of a cell suspension containing $0.5 \times 10^6$ cells/ml and allowed to attach for 4 hours. Recombinant baculoviruses were used to infect the cells at an MOI of 1-2. After 4 hours, the media was replaced with 1.0 ml of serum free media depleted for methionine and cysteine (—Met/—Cys). At 3 days pi, the culture media was replaced with 0.5 ml —Met/—Cys containing 2 µCi each [$^{35}$S]-Met and [$^{35}$S]-Cys. Cells were labeled for 16 hours after which the culture media was removed and clarified by centrifugation (Supernatant). The cells were lysed in the dish by addition of 0.2 ml lysis buffer (20 mM HEPES, pH 7.9; 130 mM NaCl; 0.2 mM EDTA; 0.5 mM DTT and 0.5% vol/vol NP-40) and then diluted up to 1.0 ml with dH$_2$O (Cell Extract). 30 µl of each supernatant and cell extract were resolved by 15% SDS-PAGE. Protein gels were stained, destained, amplified, dried and autoradiographed. Labeled bands corresponding to the recombinant proteins were visible after 16-72 hours exposure.

EXAMPLE 3

Cloning and Expression of TR2 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human HeLa 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 3(a)

Cloning and Expression in COS Cells

The expression plasmid, pTR2 HA, is made by cloning a cDNA encoding TR2 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicilin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope pcDNAIII contains, in addition, the selectable neomycin marker.

A DNA fragment encoding a TR2 is cloned into the polylinker region of the vector so that recombinant protein expression is directed by the CMV promoter. The plasmid construction strategy is as follows. The TR2 cDNA of the deposited clone is amplified using primers that contain convenient restriction sites, much as described above for construction of vectors for expression of TR2 in *E. coli*. Suitable primers include the following, which are used in this example. The 5' primer, containing the underlined BamHI site, a Kozak sequence, an AUG start codon and 6 additional codons of the 5' coding region of the complete TR2 has the following sequence:

5' GCGCGGATCCACCATGGAGCCTCCTGGAGACTGG 3' (SEQ ID NO:20). The 3' primer, containing the underlined XbaI site, a stop codon, HA tag, and 19 bp of 3' coding sequence has the following sequence (at the 3' end):

5' GCGCTCTAGATCAAGCGTAGTCTGGGACGTCGT ATGGGTAGTGGTTTGGGCTCCTCCC 3' (SEQ ID NO:21).

The PCR amplified DNA fragment and the vector, pcD-NAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR2-encoding fragment.

For expression of recombinant TR2, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR2 by the vector.

Expression of the TR2-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 3(b)

Cloning and Expression in CHO Cells

The vector pC4 is used for the expression of TR2 protein. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A., 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology,* March 1985:438-447) plus a fragment isolated from the enhancer of the immediate early gene of human cytomegalovirus (CMV) (Boshart et al., *Cell* 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeaters from other retroviruses, e.g., HIV and HTLVI. Clontech's Tet-Off and Tet-On gene expression systems and similar systems can be used to express the TR2 protein in a regulated way in mammalian cells (Gossen, M., & Bujard, H. 1992, *Proc. Natl. Acad. Sci. USA* 89: 5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete TR2 protein including its leader sequence is amplified using PCR oligonucleotide primers corresponding to the 5' and 3' sequences of the gene. The 5' primer has the sequence:

5' GCGCGGATCCACCATGGAGCCTCCTGGAGACTGG 3' (SEQ ID NO:22) containing the underlined BamHI restriction enzyme site followed by an efficient signal for initiation of translation in eukaryotes, as described by Kozak, M., *J. Mol. Biol.* 196:947-950 (1987), and 21 bases of the coding sequence of TR2 protein shown in FIGS. 1A-1B (SEQ ID NO:1). The 3' primer has the sequence:

5' GCGCGGTACCTCTACCCCAGCAGGGGCGCCA 3' (SEQ ID NO:19) containing the underlined Asp718 restriction site followed by 21 nucleotides complementary to the non-translated region of the TR2 gene shown in FIGS. 1A-1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. E. coli HB101 or XL-1 Blue cells are then transformed and bacterial are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100-200 µM. Expression of the desired gene product is analyzed, for instance, by SDS-PAGE and Western blot or by reverse phase HPLC analysis.

EXAMPLE 4

Tissue Distribution of TR2 mRNA Expression

Northern blot analysis is carried out to examine TR2 gene expression in human tissues, using methods described by, among others, Sambrook et al., cited above. A cDNA probe containing the entire nucleotide sequence of the TR2 protein (SEQ ID NO:1) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for TR2 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at –70° C. overnight, and films developed according to standard procedures.

EXAMPLE 5

Example 5(a)

Expression and Purification of TR2-Fc(TR2-Ig Fusion Protein) and Cleaved TR2

The putative transmembrane domain of translated TR2 receptor was determined by hydrophobicity using the method of Goldman et al. (*Ann. Rev. of Biophys. Biophys. Chem.* 15:321-353 (1986)) for identifying nonpolar transbilayer helices. The region upstream of this transmembrane domain, encoding the putative leader peptide and extracellular domain, was chosen for the production of an Fc fusion protein. Primers were designed to PCR the corresponding coding region from HTXBS40 with the addition of a BglII site (single underlined), a Factor Xa protease site and an Asp718I site (double underlined) at the 3' end. PCR with this primer pair (forward 35-mer:

5'CAGGAATTCGCAGCCATGGAGCCTCCTG-GAGACTG3'(SEQ ID NO:23), and reverse primer 53-mer:

5' CCATACCCAGGTACCCCTTCCCTCGATAGATCT TGCCTTCGTCACCAGCCAGC 3' (SEQ ID NO:24)), which contains 18 nucleotides of the TR2 coding sequence, resulted in one band of the expected size. This was cloned into COSFclink to give the TR2-Fclink plasmid. The PCR product was digested with EcoRI and Asp718I and ligated into the COSFclink plasmid (Johansen, et al., *J. Biol. Chem.* 270: 9459-9471 (1995)) to produce TR2-Fclink.

COS cells were transiently transfected with TR2-Fclink and the resulting supernatant was immunoprecipitated with protein A agarose. Western blot analysis of the immunoprecipitate using goat anti-human FC antibodies revealed a strong band consistent with the expected size for glycosylated TR2-Fc (greater than 47.5 kD). A 15 L transient COS transfection was performed and the resulting supernatant was purified (see below). The purified protein was used to immunize mice following DNA injection for the production of mAbs.

CHO cells were transfected with TR2-Fclink to produce stable cell lines. Five lines were chosen by dot blot analysis for expansion and were adapted to shaker flasks. The line with the highest level of TR2-Fc protein expression was identified by Western blot analysis. TR2-Fc protein purified from the supernatant of this line was used for cell binding studies by flow cytometry, either as intact protein or after factor Xa cleavage and biotinylation (see below).

Clone HTXBS40 is an allelic variant of TR2 which differs from the sequence shown in FIGS. 1A-1B (SEQ ID NO:1) in that HTXBS40 contains guanine at nucleotide 314, thymine at nucleotide 386 and cytosine at nucleotide 627.

A plasmid suitable for expression of the extracellular domain of TR2 was constructed as follows to immunize mice for the production of anti-TR2 mAbs. The Fc fragment was removed from TR2-Fclink by a BglII/XbaI digestion, Klenow was used to fill in the overhangs, and the blunt ends of the plasmid were religated. The resulting frame shift introduced a stop codon immediately following the amino acids which had originally been introduced into TR2-Fclink by the addition of the BglII site. Thus, the C terminus of the extracellular domain of TR2 is followed by only 2 amino acids (RS) in this constructed (TR2exlink).

EXAMPLE 5(b)

Purification of TR2-Fc from CHO E1A Conditioned Media Followed by Cleavage and Biotinylation of TR2

Assays

Product purity through the purification was monitored on 15% Laemmli SDS-PAGE gels run under reducing and non-reducing conditions. Protein concentration was monitored by $A_{280}$ assuming an extinction coefficient of 0.7 for the receptor and 1.28 for the chimera, both calculated from the sequence. Extinction coefficients were confirmed by AAA.

Protein G Chromatography of the TR2-Fc Fusion Protein

All steps described below were carried out at 4° C. 15 L of CHO conditioned media (CM) (0.2 µ filtered following harvest in cell culture) was applied to a 5×10 cm column of Protein G at a linear flow rate of 199 cm/h. The column has been washed with 100 mM glycine, pH 2.5 and equilibrated in 20 mM sodium phosphate, 150 mM sodium chloride, pH 7 prior to sample application. After the CM was loaded the column was washed with 5 column volumes of 20 mM sodium phosphate, 150 mM sodium chloride, pH 7 and eluted with 100 mM glycine, pH 2.5 . 435 ml of eluate was immediately neutralized with 3 M Tris, pH 8.5 and 0.2 µ filtered. Based on $A_{280}$, extinction coefficient 1.28, 65 mg of protein was recovered at 0.15 mg/ml.

Concentration/Dialysis 385 ml of Protein G eluate was concentrated in an Amicon stirred cell fitted with a 30K membrane to 34 ml at a final concentration of 1.7. The concentrate was dialyzed against buffer.

Factor Xa Cleavage and Purification to Generate Free Receptor

Six ml (10.2 mg) of TR2-Fc was added to 50 µg of Factor Xa resulting in a 1:200, e:s ratio. The mixture was incubated overnight at 4° C.

Protein G Chromatography of the Free TR2 receptor

A 1 ml column of Protein G was equilibrated in 20 mM sodium phosphate, 150 mM sodium chloride, pH 6.5 in a disposable column using gravity flow. The cleaved receptor was passed over the column 3 times after which the column was washed with 20 mM sodium phosphate, 150 mM sodium chloride, pH 6.5 until no $A_{280}$ absorbance was seen. The column was eluted with 2.5 ml of 100 mM glycine, pH 2.5 neutralized with 83 µl of 3 M Tris, pH 8.5. TR2 eluted in the nonbound fraction.

Concentration

The nonbound fraction from the Protein G column, about 12 ml, was concentrated in a Centricon 10K cell (Amicon) to about 1 ml to a final concentration of 3.5 mg/ml estimated by $A_{280}$, extinction coefficient 0.7.

Mono S Chromatography

The concentrated sample was diluted to 5 ml with 20 mM sodium phosphate, pH 6 and applied to a 0.5×5 cm Mono S column equilibrated in 20 mM sodium phosphate, pH 6 at a linear flow rate of 300 cm/h. The column was washed with 20 mM sodium phosphate, pH 6 and eluted with a 20 column volume linear gradient of 20 mM sodium phosphate, pH 6 to 20 mM sodium phosphate, 1 M sodium chloride, pH6. TR2 protein eluted in the nonbound fraction.

Concentration/Dialysis

The 3 ml nonbound fraction from the Mono S column was concentrated to 1 ml as above using a Centricon 10K cell and dialyzed against 20 mM sodium phosphate, 150 mM sodium chloride, pH 7. The concentration following dialysis was 2.1 mg/ml.

Biotinylation 0.5 mg of TR2 at 2.1 mg/ml was dialyzed against 100 mM borate, pH 8.5. A 20-fold molar excess of NHS-LC Biotin was added and the mixture was left on a rotator overnight at 4° C. The biotinylated TR2 was dialyzed against 20 mM sodium phosphate, 150 mM sodium chloride, pH 7, sterile filtered and stored at −70° C. Biotinylated was demonstrated on a Western blot probed with streptavidin HRP and subsequently developed with ECL reagent.

EXAMPLE 6

The Membrane Bound Form of the TR2 Receptor is a TNFR which Induces Lymphocytes Proliferation and Differentiation The members of the tumor necrosis factor (TNFR)/nerve growth factor receptor (NGFR) superfamily are characterized by the presence of three to six repeats of a cysteine-rich motif that consists of approximately 30 to 40 amino acids in the extracellular part of the molecule (Mallett, S. and Barclay, A. N., *Immunol. Today* 12:220 (1991)). The crystal structure of TNFR-I showed that the cysteine-rich motif (TNFR domain) was composed of three elongated strands of residues held together by a twisted ladder of disulfide bonds (Banner, D. W. et al., *Cell* 73:431 (1993). These receptors contain a hinge-like region immediately adjacent to the transmembrane domain, characterized by a lack of cysteine residues and a high proportion of serine, threonine, and proline, which are likely to be glycosylated with O-linked sugars. A cytoplasmic part of these molecules shows limited sequence similarities—a finding which may be the basis for diverse cellular signaling. At present, the members identified from human cells include CD40 (Stamenkovic, I. et al., *EMBO J.* 8:1403 (1989)), 4-IBB (Kwon, B. S. and Weissman, S. M., *Proc. Natl. Acad. Sci. USA* 86:1963(1989)), OX-40 (Mallett, S. et al., *EMBO J.* 9:1063 (1990)), TNFR-I (Loetscher, H. et al., *Cell* 61:351 (1990); Schall, T. J. et al., *Cell* 61:361 (1990)), TNFR-II (Smith, C. A. et al., *Science* 248:1019 (1990)), CD27 (Van Lier, R. A. et al., *J. Immunol.* 139:1589 (1987)), Fas (Itoh, N. et al., *Cell* 66:233 (1991)), NGFR (Johnson, D. et al., *Cell* 47:545 (1986), CD30 (Durkop, H. et al., *Cell* 68:421 (1992)) and LTBR (Baens, M. et al., *Genomics* 16:214 (1993)). Viral open reading frames encoding soluble TNFRs have also been identified, such as SFV-T2 (Smith, C. A. et al., *Science* 248:1019 (1990)), Va53 (Howard, S. T. et al., *Virology* 180:633 (1991)), G4RG (Hu, F. -Q. et al., *Virology* 204: 343 (1994)) and crmB (Smith, G. L., *J. Gen. Viol.* 74:1725 (1993)).

Recent intensive studies have shown that these molecules are involved in diverse biological activities such as immunoregulation (Armitage, R. J., *Curr. Opin. Immunol.* 6:407 (1994); Smith, C. A. et al., *Cell* 75:959 (1994)), by regulating cell proliferation (Banchereau, J. et al., *Science* 251:70 (1991); Pollok, K. E. et al., *J. Immunol.* 150:771 (1993); Baum, P. R. et al., *EMBO J.* 13:3992 (1994)), cell survival (Grass, H. -J. et al., *Blood* 83:2045 (1994); Torcia, M. et al., *Cell* 85:345-356 (1996)), and cell death (Tartaglia, L. A. et al., *Cell* 74:845 (1993); Gillette-Ferguson, I. and Sidman, C. L., *Eur. J. Immunol.* 24:1181 (1994); Krammer, P. H. et al., *Curr. Opin. Immunol.* 6:279 (1994)).

Because of their biological significance and the diverse membership of this superfamily, we predicted that there would be further members of the superfamily. By searching an EST-data base, we have identified a new member of the TNFR superfamily. We report here the initial characterization of the molecule called TR2.

MATERIAL AND METHODS

Identification and Cloning of New Members of the TNFR Superfamily

An expressed sequence tag (EST) cDNA data base, obtained over 500 different cDNA libraries (Adams, M. D. et al., *Science* 252:1651 (1991); Adams, M. D., et al., *Nature* 355:632 (1992)), was screened for sequence similarity with cysteine-rich motif of the TNFR superfamily, using the blastn and tblastn algorithms (Altschul, S. F. et al., *J. Mol. Biol.* 215:403 (1990)). One EST (HT1SB52-ATCC Accession No. 97059) was identified in a human T cell line library which showed significant identity to TNFR-II at the amino acid level. This sequence was used to clone the missing 5' end by RACE (rapid amplification of cDNA ends) using a 5'-RACE-ready cDNA of human leukocytes (Clontech, PT1155-1. Cat. #7301-1). This sequence matched four further ESTs (HTOBH42, HTOAU65, HLHA49 and HTXBS40). Complete sequencing of these and other cDNAs indicated that they contained an identical open reading frame homologous to the TNFR superfamily and was named TR2. Analysis of several other ESTs and cDNAs indicated that some cDNAs had additional sequences inserted in the open reading frame identified above, and might represent various partially-spliced mRNAs.

Cells

The myeloid and B-cell lines studied represent cell types at different stages of the differentiation pathway. KG1a and PLB 985 (Koeffler, H. et al., *Blood* 56:265 (1980); Tucker, K. et al., *Blood* 70:372 (1987)) were obtained from Phillip Koeffler (UCLA School of Medicine), BJA-B was from Z. Jonak (SmithKline Beecham), and TF 274, a stromal cell line exhibiting osteoblastic features, was generated from the bone marrow of a healthy male donor (Tan & Jonak, unpublished). All of the other cell lines were obtained from the American Type Culture Collection (Manassas, Va.). Monocytes were prepared by differential centrifugation of peripheral blood mononuclear cells (PBMC) and adhesion to tissue culture dish. $CD19^+$, $CD4^+$ and $CD8^+$ were isolated from PBMC by immunomagnetic beads (Dynal, Lake Success, N.Y.). Endothelial cells from human coronary artery were purchased from clonetics (Clonetics, Calif.).

RNA and DNA Hybridization

Total RNA of adult tissues was purchases from Clontech (Palo Alto, Calif.), or extracted from primary cells and cell lines with TriReagent (Molecular Research Center, Inc., Cincinnati, Ohio) 5 to 7.5 µg of total RNA was fractionated in a 1% agarose gel containing formaldehyde, as described (Sambrook et al., *Molecular Cloning*, Cold Springs Harbor (1989)) and transferred quantitatively to Zeta-probe nylon membrane (Biorad, Hercules, Calif.) by vacuum-blotting. The blots were prehybridized, hybridized with $^{32}$P-labeled XhoI/EcoRI fragment of TR2 or OX-40 probe, washed under stringent conditions and exposed to X-ray films.

High molecular weight human DNA was digested with various restriction enzymes and fractionated in 0.8% agarose gel. The DNA was denatured, neutralized and transferred to nylon membrane and hybridized to $^{32}$P-labeled TR-2 or its variant cDNA.

In Situ Hybridization and FISH Detection

The in situ hybridization and FISH detection of TR2 location in human chromosome were performed as previously described (Heng, H. H. Q. et al., *Proc. Natl. Acad. Sci. USA* 89:9509 (1992); Heng, H. H. Q. et al., *Human Molecular Genetics* 3:61 (1994)). FISH signals and the DAPI banding pattern were recorded separately by taking photographs, and the assignment of the FISH mapping data with chromosomal bands was achieved by superimposing FISH signals with DAPI banded chromosome (Heng, H. H. Q. and Tsui, L. -C. *Chromosoma*. 102:325 (1993)).

Production of Recombination TR2-Fc Fusion Proteins

The 5' portion of the TR2 containing the entire putative open reading frame of extracellular domain was amplified by polymerase chain reaction (Saiki, R. K. et al., *Science* 239: 487 (1988)). For correctly oriented cloning, a HindIII site on the 5' end of the forward primer and a BglII site on the 5' end of the reverse primer were created. The Fc portion of human $IgG_1$ was PCR-amplified from ARH-77 (ATCC) cell RNA and cloned in SmaI site of pGem7 vector (Promega). The Fc fragment including hinge, $CH_2$, and $CH_3$ domain sequences containing a BglII site at its 5' and an XhoI site at its 3' end. The HindIII-BG1II fragment of TR2 cDNA was inserted into the upstream of human $IgG_1$Fc and an in frame fusion was confirmed by sequencing. The TR2-Fc fragment was released by digesting the plasmid with HindIII-XhoI and cloned it into pcDNA3 expression plasmid.

The TR2-Fc plasmid, linearized with PvuI, was transferred into NIH 3T3 by the calcium phosphate co-precipitation method. After selection in 400 µg/ml G418, neomycin-resistant colonies were picked and expanded. ELISA with anti-human $IgG_1$ and Northern analysis with $^{32}$P-labeled TR2 probe were used to select clones that produce high levels of TR2-Fc in the supernatant. In some experiments, a slightly different engineered TR2-Fc produced in Chinese hamster ovary (CHO) cells was used. The TR2-Fc was purified by protein G chromatography, and the amino acid sequence of N-terminus of the TR2-Fc fusion protein was determined by automatic peptide sequencer (ABI). TR2-Fc was used to produce polyclonal rabbit and anti-TR2 antibodies.

Blocking MLR-Mediated PBMC Proliferation

PBMC were isolated from three healthy adult volunteers by FicoII gradient centrifugation at 400×g for 30 minutes. PBMCs were recovered, washed in RPMI 1640 (GIBCO-BRL) supplemented with 10% FBS, 300 µg/ml L-glutamine and 50 µg/ml genetomycin, and adjusted to $1 \times 10^6$ cells/ml for two donors and to $2 \times 10^5$ cells/ml for the third donor.

Fifty µl of each cell suspension was added to 96-well (round bottom) plates (Falcon, Franklin Lakes, NS) together with 50 µl of TR2-Fc, IL-5R-Fc, anti-CD4 mAb or control mAb. Plates were incubated at 37° C. in 5% $CO_2$ for 96 hours. One µCi of [$^3$H]-methylthymidine (ICN Biomedicals, Costa Mesa, Calif.) was then added for an additional 16 hours. Cells were harvested and radioactivity was counted.

RESULTS AND DISCUSSION

TR2 is a New Member of the TNFR Superfamily

FIGS. 1A-1B (SEQ ID NO:2) shows the amino acid sequence of TR2 deduced from the longest open reading frame of one of the isolated cDNAs (HLHAB49). Comparison with other sequenced cDNAs and ESTs in the database indicated potential allelic variants which resulted in amino acid changes at positions 17 (either Arg or Lys) and 41 (either Ser or Phe) of the protein sequence shown in FIGS. 1A-1B (amino acid residues −20 and 5 in SEQ ID NO:2).

The open reading frame encodes 283 amino acids with a calculated molecular weight of 30,417. The TR2 protein was expected to be a receptor. Therefore, the potential signal sequence and transmembrane domain were sought. A hydrophobic stretch of 23 amino acids towards the C terminus (amino acids 201-225) (FIGS. 1A-1B) was assigned as a transmembrane domain because it made a potentially single helical span, but the signal sequence was less obvious. The potential ectodomain TR2 was expressed in NIH 3T3 and CHO cells as a Fc-fusion protein, and the N-terminal amino acid sequence of the recombinant TR2-Fc protein was determined in both cases. The N-terminal sequence of the processed mature TR2 started from amino acid 37, indicating that the first 36 amino acids constituted the signal sequence (FIGS. 1A-1B).

Using a polyclonal rabbit antibody raised to TR2, the molecular size of natural TR2 was determined to be 38 kD by Western analysis. Since the protein backbone of processed TR2 would be composed of 247 amino acids with an Mr of 26,000, the protein must be modified post-translationally. Two potential asparagine-linked glycosylation sites are located at amino acid positions 110 and 173 (FIGS. 1A-1B). Along with the other members of the TNFR family, TR2 contains the characteristic cysteine-rich motifs which have been shown by X-ray crystallography (Banner et al., *Cell* 73:431 (1993)) to represent a repetitive structural unit (Banner, D. W. et al., *Cell* 73:431 (1993)). FIG. 16 shows the potential TNFR domain aligned among TR2 (SEQ ID NO:2), TNFR-I (SEQ ID NO:10), TNFR-II (SEQ ID NO:11), CD40 (SEQ ID NO:12) and 4-1BB (SEQ ID NO:13). TR2 contained two perfect TNFR domain and two imperfect ones.

The TR2 cystoplasmic tail (TR2 cy) appears to be more closely related to those of CD40cy and 4-1BBcy, and does not contain the death domain seen in the Fas and TNFR-I intracellular domains. Although the homology is moderate, the $Thr^{266}$ of TR2 is aligned with $Thr^{233}$ of 4-1BB and $Thr^{254}$ of CD40. This may be significant because Inui et al., (Inui, S. et al., *Eur. J. Immunol.* 20:1747 (1990)) found that $Thr^{254}$ was essential for CD40 signal transduction and when the $Thr^{254}$ of CD40 was mutated, the CD40 bd did not bind to the CD40cy (Hu, H. M. et al., *J. Biol. Chem.* 369:30069 (1994)). Signals through 4-1BB and CD40 have been shown to be costimulatory to T cells and B cells respectively (Banchereau, J. and Rousset, F., *Nature* 353:678 (1991); Hurtaldo, J. et al., *J. Immunol.* 155:3360 (1995)).

TABLE 2

GENE EXPRESSION OF TR2 AND OX40 IN TISSUES AND CELLS

| SOURCE | | GENE | |
|---|---|---|---|
| | | TR2 | OX-40 |
| TISSUES (adult) | | | |
| Brain | | +/− | − |
| Heart | | + | − |
| Lung | | + | − |
| Thymus | | ++ | − |
| Spleen | | +++ | − |
| Liver | | + | − |
| Kidney | | + | − |
| Small Intestine | | +++ | − |
| Prostate | | ++ | − |
| Skeletal Muscle | | +/− | − |
| Ovary | | + | |
| Pancreas | | + | |
| Colon | | + | |
| Thyroid | | + | |
| Spinal Cord | | + | |
| Trachea | | + | |
| Adrenal Gland | | + | |
| Lymph Node | | +++ | |
| PRIMARY CELLS | | | |
| PBL, CD19+ | | ++ | − |
| PBL, CD8+ | | ++ | − |
| PBL, CD8+ (activated) | | ++ | ++ |
| PBL | | +++ | |
| PBL, CD4+ (activated) | | ++ | ++ |
| Bone Marrow | | + | − |
| Monocyte | | ++ | − |
| Endothelial | | + | − |
| HEMATOPOIETIC CELL LINES | | | |
| Erythroid | | | |
| K562 | | − | |
| HEL | | + | |
| Myeloid | | | |
| KG1a | (Promyeloblast) | + | + |
| KG1 | (Myeloblast) | ± | ± |
| PLB985 | (Late myeloblast) | − | |
| HL60 | (Promyelocyte) | ± | − |
| U937 | (Promonocyte) | ± | |
| THP-1 | (Monocle) | + | − |
| B-Lymphocyte | | | |
| REH | (Pre-preB) | ± | |
| BJA-B | (Early B, IgM) | + | − |
| Raji | (Mature B, IgM) | + | |
| IM-9 | (Mature B, IgG) | − | − |
| T-Lymphocyte | | | |
| Sup-T1 | (CD4+) | − | |
| Molt-3 | (CD4+) | ± | − |
| H9 | (CD4+) | + | |
| Jurkat | (CD4+) | + | + | no entry = not tested, − = not detected, ± to ++ = increasing amounts of RNA detected TR2 RNA Expression A human tissue RNA blot was used to determine tissue distribution of TR2 RNA expression. TR2 RNA was detected in several tissues with a relatively high level in the lung, spleen and thymus (Table 2) but was not detected by this method in the brain, liver or skeletal muscle (Table 2). TR-2 was also expressed in monocytes, $CD19^+$ B cells, and resting or PMA plus PHA-treated $CD4^+$ or $CD8^+$ T cells. It was only weakly expressed in bone marrow and endothelial cells (Tables 2 and 3), although expression was observed in the hematopoietic cell line KG1a (Table 2). For comparison, the tissue distribution of OX-40, another member of the TNFR superfamily, was examined (Table 2). Unlike TR2, OX-40 was not detected in any tissues examined, and was detected only in activated T-cells and KG1a. Several cell lines were negative for TR2 expression, including TF 274 (bone marrow stromal), MG 63 and TE 85 (osteosarcoma), RL 95-2 (endometrial sarcoma), MCF-7 and T-47D (breast cancer cells), BE, HT 29 (colon cancer cells), HTB-11 and IMR-32 (neuroblastoma), although TR2 was found in the rhabdosarcoma HTB-82 (data not shown).

Several cell lines were examined for inducible TR2 expression. HL60, U937 and THP1, which belongs to the myelomonogytic lineage, all increased TR2 expression in response to the differentiation agents PMA or DMSO. Increases in expression in response to these agents were observed in KG1a and Jurkat cells. In contrast, PMA did not induce TR2 expression in MG63, but unexpectedly TNF-α did.

In almost all cases, the predominant mRNA was approximately 1.7 kb in size, although several higher molecular weight species could be detected in some tissues. While many cDNAs and ESTs which were sequenced contained insertions in the coding region indicative of partial splicing, we only detected one major protein by Western blot, suggesting that if these encode alternate proteins they are not evident in the cells we examined. The abundance of higher MW mRNAs raises the possibility that TR2 may in part be regulated at the level of mRNA maturation.

TABLE 3

RELATIVE ABUNDANCE (RA) OF TR2 RNA IN VARIOUS TISSUE AND CELL TYPES

| Tissue or Cell Type | RA |
|---|---|
| Activated Macrophage (LPS) | 22 |
| Breast Lymph Node | 5 |
| B Cell Lymphoma | 5 |
| Activated Monocytes | 2 |
| Activated T Cells | 3 |
| Activated Neutrophil | 2 |
| Tonsils | 5 |
| Thymus | 3 |
| Anergic T-cell | 1 |
| Jurkat T-Cell | 3 |
| Raji Cells (Cycloheximide Treated) | 3 |
| Atrophic Endometrium | 1 |
| Bone Marrow | 1 |
| Brain | 1 |
| Breast | 1 |
| CD34 Depleted Buffy Coat (Cord Blood) | 1 |
| Cerebellum | 1 |
| Corpus Colosum | 1 |
| Caco-2 Cells (adenocarcinoma, colon) | 1 |
| Fetal Dura Mater | 1 |
| Fetal Heart | 1 |
| Fetal Lung | 2 |
| Glioblastoma | 1 |
| Hypothalamus, Schizophrenia | 1 |
| Infant Brain | 2 |
| Lung | 2 |
| Osteosarcoma | 1 |
| Pancreas Tumor | 1 |
| Placenta | 2 |
| Small Intestine | 1 |
| Smooth Muscle | 1 |
| Stomach | 2 |
| T-Cell Lymphoma | 1 |
| T-Cells | 1 |
| Testes | 3 |
| Testes Tumor | 2 |
| Tongue | 1 |
| Umbilical Vein Endothelial Cells | 2 |
| White Fat | 3 |

TR2 Maps at 1P36.2-P36.3

The FISH mapping procedure was applied to localize the TR2 gene to a specific human chromosomal region. The assignment of a hybridization signal to the short arm of chromosome 1 was obtained with the aid of DAPI banding. A total of 10 metatic figures, were photographed which indicated that the TR2 gene is located on the chromosome 1 region p36.2-p36.3. The TR2 position is in close proximity with CD30 (Smith, C. A. et al., *Cell* 73:1349-1360 (1993), 4-1BB (Kwon, B. S. et al., *J. Immunol.* 152:2256-2262 (1994); Goodwin, R. G. et al., *Eur. J. Immunol.* 23:2631-2641 (1993), OX-40 (Birkeland, M. L. et al., *Eur. J. Immunol.* 25:926-930 (1995), and TNFR-II (Baker, E. et al., *Cytogenet. & Cell Genet.* 57:117-118 (1991), suggesting that it evolved through a localized gene duplication event. Interestingly, all of these receptors have stimulatory phenotypes in T cells in response to conjugate ligand binding, in contrast to Fas and TNFR-1 which stimulate apoptosis. This prompted us to test if TR2 might be involved in lymphocyte stimulation.

TR2-Fc Interfaces with MLR-Mediated Proliferation of PBMC

To determine the possible involvement of cell surface TR2 with its ligand in lymphocyte proliferation, we examined allogeneic MLR proliferative responses. When TR-2-Fc was added to the culture, a significant reduction of maximal responses was observed ($p<0.05$). The addition of TR2-Fc at 100 µg/ml inhibited the proliferation up to 53%. No significant inhibition of proliferation was observed with the control IL-5R-Fc. Surprisingly, at high concentrations (10-100 µg/ml) IL-5R-Fc was shown to enhance proliferation. An anti-CD4 mAb assayed simultaneously inhibited MLR-mediated proliferation up to 60%, whereas a control anti-IL-5 mAb failed to inhibit the proliferation. It is well known that a major component of the MLR proliferative response is T-cell dependent, hence, it would appear that inhibiting the interaction of TR2 with its ligand prevents optimal T lymphocyte activation and proliferation. The inhibition of MLR proliferation by TR2-Fc at concentrations of 1-100 µg/ml compares favorably with biological effects seen with other TNFR-Fc superfamily members such as CD40-Fc (unpublished results, Jeremy Harrop).

Hence, we have identified an additional member of the TNF receptor superfamily which either plays a direct role in T cell stimulation or binds to a ligand which can stimulate T cell proliferation through one or more receptors which may include TR2. Consistent with a direct role for TR2 is the similarity of the cytoplasmic domain with CD40 and 4-1BB. We are currently trying to identify this ligand to which TR2 binds in order to clarify its role.

EXAMPLE 7

Expression Pattern of TNF Receptor Expression in Human Tissue

Northern blot analysis is carried out to examine the levels of expression of TNF receptor in human tissues. Total cellular RNA samples are isolated with RNAzol™ B system (Biotecx Laboratories, Inc., Houston, Tex.). About 10 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime It kit with 50 ng DNA fragment. The labeled DNA is purified with a Select-G-50 column (5 Prime-3 Prime, Inc. Boulder, Colo.). The filter is then hybridized with radioactive labeled full length TNF receptor gene at 1,000,000 cpm/ml in 0.5 M $NaPO_4$, pH 7.4 and 7% SDS overnight at 65° C. After washing twice at room temperature and twice at 60° C. with 0.5×SSC, 0.1% SDS, the filter is then exposed at −70° C. overnight with an intensifying screen.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated Human Tumor Necrosis Factor Receptor-Like 2 protein comprising amino acids 1 to 245 of SEQ ID NO:26.

2. The isolated protein of claim 1, which comprises amino acids −38 to 245 of SEQ ID NO:26.

3. The isolated protein of claim 1, which is produced by a recombinant host cell.

4. The isolated protein of claim 1, which comprises a heterologous polypeptide.

5. The isolated protein of claim 4, wherein said a heterologous polypeptide comprise the Fc portion of an antibody molecule.

6. A composition comprising the isolated protein of claim 1 and a carrier.

7. An isolated protein comprising 4 contiguous amino acids of the complete amino acid sequence encoded by the cDNA clone contained in ATCC Deposit No. 97059, wherein said 30 contiguous amino acids comprises an antigenic determinant for the polypeptide consisting of the amino acid sequence encoded by the cDNA clone contained in ATCC Deposit No. 97059.

8. The isolated protein of claim 7, which comprises the complete amino acid sequence encoded by the cDNA clone contained in ATCC Deposit No. 97059.

9. The isolated protein of claim 7, which is produced by a recombinant host cell.

10. The isolated protein of claim 7, which comprises a heterologous polypeptide.

11. The isolated protein of claim 10, wherein said a heterologous polypeptide comprises the Fc portion of an antibody molecule.

12. A composition comprising the isolated protein of claim 7 and a carrier.

13. An isolated Human Tumor Necrosis Factor Receptor-Like 2 protein comprising the mature amino acid sequence encoded by the cDNA clone contained in ATCC Deposit No. 97058.

14. The isolated protein of claim 13, which comprises the complete amino acid sequence encoded by the cDNA clone contained in ATCC Deposit No. 97058.

15. The isolated protein of claim 13, which is produced by a recombinant host cell.

16. The isolated protein of claim 13, which comprises a heterologous polypeptide.

17. The isolated protein of claim 16, wherein said a heterologous polypeptide comprises the Fc portion of an antibody molecule.

18. A composition comprising the isolated protein of claim 13 and a carrier.

19. An isolated Human Tumor Necrosis Factor Receptor-Like 2 protein comprising the mature amino acid sequence encoded by the cDNA clone contained in ATCC Deposit No. 97057.

20. The isolated protein of claim 19, which comprises the complete amino acid sequence encoded by the cDNA clone contained in ATCC Deposit No. 97057.

21. The isolated protein of claim 19, which is produced by a recombinant host cell.

22. The isolated protein of claim 19, which comprises a heterologous polypeptide.

23. The isolated protein of claim 22, wherein said a heterologous polypeptide comprises the Fc portion of an antibody molecule.

24. A composition comprising the isolated protein of claim 19 and a carrier.

25. An isolated Human Tumor Necrosis Factor Receptor-Like 2 protein comprising amino acids 1 to 162 of SEQ ID NO:26.

26. The isolated protein of claim 25, which comprises amino acids −38 to 162 of SEQ ID NO:26.

27. The isolated protein of claim 25, which is produced by a recombinant host cell.

28. The isolated protein of claim 25, which comprises a heterologous polypeptide.

29. The isolated protein of claim 28, where said a heterologous polypeptide comprises the Fc portion of an antibody molecule.

30. A composition comprising the isolated protein of claim 25 and a carrier.

31. An isolated protein comprising 30 contiguous amino acids of the complete amino acid sequence encoded by the cDNA clone contained in ATCC Deposit No. 97058, wherein said 30 contiguous amino acids comprises an antigenic determinant for the polypeptide consisting of the amino acid sequence encoded by the cDNA clone contained in ATCC Deposit No. 97058.

32. The isolated protein of claim 31, which comprises the complete amino acid sequence encoded by the cDNA clone contained in ATCC Deposit No. 97058.

33. The isolated protein of claim 31, which is produced by a recombinant host cell.

34. The isolated protein of claim 31, which comprises a heterologous polypeptide.

35. The isolated protein of claim 34, wherein said a heterologous polypeptide comprises the Fc portion of an antibody molecule.

36. A composition comprising the isolated protein of claim 31 and a carrier.

37. An isolated protein comprising 30 contiguous amino acids of the complete amino acid sequence encoded by the cDNA clone contained in ATCC Deposit No. 97057, wherein said 30 contiguous amino acids comprises an antigenic determinant for the polypeptide consisting of the amino acid sequence encoded by the cDNA clone contained in ATCC Deposit No. 97057.

38. The isolated protein of claim 37, which comprises the complete amino acid sequence encoded by the cDNA clone contained in ATCC Deposit No. 97057.

39. The isolated protein of claim 37, which is produced by a recombinant host cell.

40. The isolated protein of claim 37, which comprises a heterologous polypeptide.

41. The isolated protein of claim 40, wherein said a heterologous polypeptide comprises the Fc portion of an antibody molecule.

42. A composition comprising the isolated protein of claim 37 and a carrier.

43. An isolated protein comprising 30 contiguous amino acids of the polypeptide consisting of the amino acid sequence of SEQ ID NO:26, wherein said 30 contiguous amino acids comprises an antigenic determinant for the polypeptide consisting of the amino acid sequence of SEQ ID NO:26.

44. The isolated protein of claim 43, which is produced by a recombinant host cell.

45. The isolated protein of claim 43, which comprises a heterologous polypeptide.

46. The isolated protein of claim 45, wherein said a heterologous polypeptide comprises the Fc portion of an antibody molecule.

47. A composition comprising the isolated protein of claim 43 and a carrier.

48. An isolated protein comprising the mature amino acid sequence encoded by the cDNA clone contained in ATCC Deposit No. 97059.

49. The isolated protein of claim 48, which is produced by a recombinant host cell.

50. The isolated protein of claim 48, which comprises a heterologous polypeptide.

51. The isolated protein of claim 50, wherein said a heterologous polypeptide comprises the Fc portion of an antibody molecule.

52. A composition comprising the isolated protein of claim 48 and a carrier.

* * * * *

UNITED STATES PATENT AND TRADEMARK OFFICE
CERTIFICATE OF CORRECTION

| | |
|---|---|
| PATENT NO. | : 7,446,169 B1 |
| APPLICATION NO. | : 09/340690 |
| DATED | : November 4, 2008 |
| INVENTOR(S) | : Ni et al. |

Page 1 of 1

It is certified that error appears in the above-identified patent and that said Letters Patent is hereby corrected as shown below:

In column 3, line 7 under "SUMMARY OF THE INVENTION," delete "in bacterial hosts";

In column 4, line 19 under "BRIEF DESCRIPTION OF THE FIGURES," delete "46:591; percent identity: 28.788." and insert -- 46.591; percent identity: 28.788. --;

In column 5, lines 10-11 under "DETAILED DESCRIPTION OF THE PREFERRED EMBODIMENTS," delete "12301 Parklawn Drive, Rockville, Md. 20852," and insert -- 10801 University Blvd., Manassas, VA 20110-2209, USA (present address) --;

In column 6, line 25, delete "The deposited clones are contained in the pBluescript SK(-) plasmid (Stratagene, LaJolla, Calif.)." and insert -- All of the deposited clones are contained in the pBluescript SK(-) plasmid (Stratagene, LaJolla, Calif.). --.

Col. 80, Claim 7, delete "An isolated protein comprising 4 contiguous amino acids" and insert -- An isolated protein comprising 30 contiguous amino acids --.

Signed and Sealed this

Sixth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,446,169 B1  
APPLICATION NO. : 09/340690  
DATED : November 4, 2008  
INVENTOR(S) : Ni et al.

Page 1 of 1

It is certified that error appears in the above-identified patent and that said Letters Patent is hereby corrected as shown below:

In column 3, line 7 under "SUMMARY OF THE INVENTION," delete "in bacterial hosts";

In column 4, line 19 under "BRIEF DESCRIPTION OF THE FIGURES," delete "46:591; percent identity: 28.788." and insert -- 46.591; percent identity: 28.788. --;

In column 5, lines 10-11 under "DETAILED DESCRIPTION OF THE PREFERRED EMBODIMENTS," delete "12301 Parklawn Drive, Rockville, Md. 20852," and insert -- 10801 University Blvd., Manassas, VA 20110-2209, USA (present address) --;

In column 6, line 25, delete "The deposited clones are contained in the pBluescript SK(-) plasmid (Stratagene, LaJolla, Calif.)." and insert -- All of the deposited clones are contained in the pBluescript SK(-) plasmid (Stratagene, LaJolla, Calif.). --.

Col. 80, line 66, Claim 7, delete "An isolated protein comprising 4 contiguous amino acids" and insert -- An isolated protein comprising 30 contiguous amino acids --.

This certificate supersedes the Certificate of Correction issued July 6, 2010.

Signed and Sealed this

Third Day of August, 2010

David J. Kappos  
*Director of the United States Patent and Trademark Office*